United States Patent
Markwalder et al.

(10) Patent No.: US 8,791,257 B2
(45) Date of Patent: Jul. 29, 2014

(54) SUBSTITUTED PYRROLOTRIAZINES AS PROTEIN KINASE INHIBITORS

(75) Inventors: Jay A. Markwalder, New London, PA (US); Brian E. Fink, Yardley, PA (US); Ashvinikumar V. Gavai, Princeton Junction, NJ (US); Liqi He, Furlong, PA (US); Soong-Hoon Kim, Titusville, NJ (US); Steven P. Seitz, Swarthmore, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 13/638,210

(22) PCT Filed: Mar. 30, 2011

(86) PCT No.: PCT/US2011/030437
§ 371 (c)(1),
(2), (4) Date: Sep. 28, 2012

(87) PCT Pub. No.: WO2011/123493
PCT Pub. Date: Oct. 6, 2011

(65) Prior Publication Data
US 2013/0023514 A1    Jan. 24, 2013

Related U.S. Application Data

(60) Provisional application No. 61/319,562, filed on Mar. 31, 2010.

(51) Int. Cl.
| C07D 487/04 | (2006.01) |
| --- | --- |
| A61K 31/53 | (2006.01) |
| A61P 19/02 | (2006.01) |
| C07D 401/04 | (2006.01) |
| C07D 401/14 | (2006.01) |
| C07D 403/04 | (2006.01) |
| C07D 403/14 | (2006.01) |
| C07D 407/04 | (2006.01) |
| C07D 407/14 | (2006.01) |
| C07D 409/04 | (2006.01) |
| C07D 409/14 | (2006.01) |
| C07D 417/04 | (2006.01) |
| C07D 417/14 | (2006.01) |

(52) U.S. Cl.
CPC ........... *C07D 487/04* (2013.01); *C07D 401/04* (2013.01); *C07D 401/14* (2013.01); *C07D 403/04* (2013.01); *C07D 403/14* (2013.01); *C07D 407/04* (2013.01); *C07D 407/14* (2013.01); *C07D 409/04* (2013.01); *C07D 409/14* (2013.01); *C07D 417/04* (2013.01); *C07D 417/14* (2013.01)
USPC .......................... 544/183; 514/243

(58) Field of Classification Search
CPC .. C07D 487/04; C07D 401/04; C07D 401/14; C07D 403/04; C07D 403/14; C07D 407/04; C07D 407/14; C07D 409/04; C07D 409/14; A61K 31/53
USPC ........................... 544/183; 514/243
See application file for complete search history.

(56) References Cited

U.S. PATENT DOCUMENTS

| 7,442,700 B2 | 10/2008 | Mastalerz et al. |
| --- | --- | --- |
| 7,514,460 B2 | 4/2009 | Herz et al. |

FOREIGN PATENT DOCUMENTS

| WO | WO 2004/082606 | 9/2004 |
| --- | --- | --- |
| WO | WO 2005/097052 | 10/2005 |
| WO | WO 2007/064931 | 6/2007 |
| WO | WO 2007/087395 | 8/2007 |
| WO | WO 2007/103839 | 9/2007 |
| WO | WO 2008/005956 | 1/2008 |
| WO | WO 2008/057402 | 5/2008 |
| WO | WO 2008/089105 | 7/2008 |
| WO | WO 2008/131050 | 10/2008 |
| WO | WO 2009/117157 | 9/2009 |
| WO | WO 2009/136966 | 11/2009 |
| WO | WO 2010/002877 | 1/2010 |

OTHER PUBLICATIONS

Duncan et al., Biochimica et Biophysica Acta 1784 (2008) 33-47.*
Battistutta et al., Mol Cell Biochem (2011) 356:67-73.*
Cozza et al. Curr Med Chem. 2011;18(19):2867-84.*
Cozza et al. Med Res Rev. May 2010;30(3):419-62.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*

(Continued)

*Primary Examiner* — Venkataraman Balasubramanian
(74) *Attorney, Agent, or Firm* — Hong Liu

(57) ABSTRACT

The invention provides compounds of Formula (I) and pharmaceutically acceptable salts thereof. The Formula (I) pyrrolotriazines inhibit protein kinase activity thereby making them useful as anticancer agents.

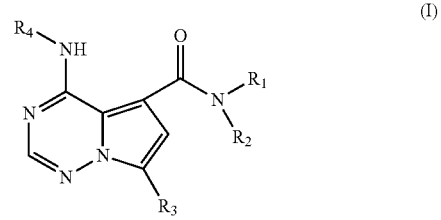

13 Claims, No Drawings

(56) References Cited

OTHER PUBLICATIONS

Dermer et al., Bio/Technology, 1994, 12:320.*

Golub et al., Science, 286, 531-537, 1999.*

Cecil Textbook of Medicine, edited by Bennet, J.C., and Plum F., 20th edition, vol. 1, 1004-1010, 1996.*

Bundgaard, H., Chapter 5: "Design and Application of Prodrugs", Krogsgaard-Larsen, P. et al., eds., A Textbook of Drug Design and Development, pp. 113-191, Harwood Academic Publishers, publ. (1991).

Bundgaard, H., "Prodrugs as a means to improve the delivery of peptide drugs", Advanced Drug Delivery Reviews, vol. 8, pp. 1-38 (1992).

Bundgaard, H., ed., Design of Prodrugs, Elsevier Science Publishers B.V., publ. (1985) (table of contents).

Daya-Makin, M. et al., "Activation of a Tumor-associated Protein Kinase ($p40^{TAK}$) and Casein Kinase 2 in Human Squamous Cell Carcinomas and Adenocarcinomas of the Lung", Cancer Research, vol. 54, pp. 2262-2268 (1994).

Faust, R.A. et al., "Antisense Oligonucleotides Against Protein Kinase CK2-α Inhibit Growth of Squamous Cell Carcinoma of the Head and Neck In Vitro", Head & Neck, vol. 22, pp. 341-346 (2000).

Guari, Y. et al., "Palladium-Catalyzed Amination of Aryl Bromides and Aryl Triflates Using Diphosphane Ligands: a Kinetic Study", Chem. Eur. J., vol. 7, No. 2, pp. 475-482 (2001).

Landesman-Bollag, E. et al., "Protein kinase CK2 in mammary gland tumorigenesis", Oncogene, vol. 20, pp. 3247-3257 (2001).

Nie, Z. et al., "Structure-based design and synthesis of novel macrocyclic pyrazolo[1,5-α] [1,3,5]triazine compounds as potent inhibitors of protein kinase CK2 and their anticancer activities", Bioorganic & Medicinal Chemistry Letters, vol. 18, pp. 619-623 (2008).

Nie, Z. et al., "Structure-based design, synthesis, and study of pyrazolo[1,5-a][1,3,5]triazine derivatives as potent inhibitors of protein kinase CK2", Bioorganic & Medicinal Chemistry Letters, vol. 17, pp. 4191-4195 (2007).

Stalter, G. et al., "Asymmetric Expression of Protein Kinase CK2 Subunits in Human Kidney Tumors", Biochemical and Biophysical Research Communications, vol. 202, No. 1, pp. 141-147 (1994).

Suzuki, K. et al., "A New Hybrid Phosphine Ligand for Palladium-Catalyzed Amination of Aryl Halides", Adv. Synth. Catal., vol. 350, pp. 652-656 (2008).

Wang, G. et al., "Role of Protein Kinase CK2 in the Regulation of Tumor Necrosis Factor-Related Apoptosis Inducing Ligand-Induced Apoptosis in Prostate Cancer Cells", Cancer Res., vol. 66, No. 4, pp. 2242-2249 (2006).

Widder, K.J. et al., eds., Section III: "Prodrugs", Methods in Enzymology, vol. 112, pp. 309-396, Academic Press, Inc., publ. (1985).

* cited by examiner

SUBSTITUTED PYRROLOTRIAZINES AS PROTEIN KINASE INHIBITORS

CROSS-REFERENCE TO RELATED APPLICATIONS

This application claims the benefit of U.S. Provisional Application Ser. No. 61/319,562 filed Mar. 31, 2010.

FIELD OF THE INVENTION

The invention relates to novel substituted pyrrolotriazine compounds useful as protein kinase inhibitors. The invention also relates to methods of using the compounds in the treatment of proliferative and other types of diseases and to pharmaceutical compositions containing the compounds.

BACKGROUND OF THE INVENTION

The invention relates to fused heterocyclic compounds which inhibit protein kinase enzymes, compositions which contain protein kinase inhibiting compounds and methods of using inhibitors of protein kinase enzymes to treat diseases which are characterized by an overexpression or upregulation of protein kinases. Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. An extracellular stimulus may effect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Serine/threonine kinases are a class of protein kinases that are among the most promising drug targets for future small molecule inhibitors. Inhibition of serine/threonine kinases is likely to have relevance to the treatment of cancer, diabetes and a variety of inflammatory disorders. The successful development of GLEEVEC® as a Bcr/Abl protein kinase inhibitor has provided further evidence that protein kinases including protein kinase CK2 are valid drug targets for potential cancer therapies.

Protein kinase CK2 (formerly known as casein kinase II) is a highly conserved serine/threonine kinase. Protein kinase CK2 is ubiquitously distributed and constitutively active in eukaryotes. In mammals, the enzyme exists in two isozymic forms due to variations in the catalytic subunits of the enzyme. The CK2 holoenzyme is a heterotetrameric complex composed of two catalytic α (CK2A1) subunits or α' (CK2A2) subunits and two regulatory β-subunits. The formation of CK2 complexes containing the catalytic subunits requires dimerization of the regulatory β-subunits. CK2 interacts with a variety of cellular proteins and has been implicated in cell replication such as cell proliferation and differentiation, cellular survival, and tumorigenesis. With respect to tumorigenesis, protein kinase CK2 has been implicated in kidney tumors (Stalter et al., "Asymmetric expression of protein kinase CK2 subunits in human kidney tumors", *Biochem. Biophys. Res. Commun.*, 202:141-147 (1994)), mammary gland tumors (Landesman-Bollag et al., "Protein kinase CK2 in mammary gland tumorigenesis", *Oncology*, 20:3247-3257 (2001)), lung carcinoma (Daya-Makin et al., "Activation of a tumor-associated protein kinase (p40TAK) and casein kinase II in human squamous cell carcinomas and adenocarcinomas of the lung", *Cancer Res.*, 54:2262-2268 (1994)), head and neck carcinoma (Faust et al., "Antisense oligonucleotides against protein kinase CK2-α inhibit growth of squamous cell carcinoma of the head and neck in vitro", *Head Neck*, 22:341-346 (2000)), and prostate cancer (Wang et al., "Role of protein kinase CK2 in the regulation of tumor necrosis factor-related apoptosis inducing ligand-induced apoptosis in prostate cancer cells", *Cancer Res.*, 66:2242-2249 (2006)).

Inhibitors of protein kinases are widely sought and small molecule compounds capable of modulating protein kinases have been reported. In particular, pyrrolotriazine derivatives have been described in patent literature such as PCT publications WO 2005/097052, WO 2007/087395, WO 2008/089105, WO 2009/008992, WO 2009/009016, WO 2009/023179, WO2009/136966, and European patents EP 1674467 and EP 1149583. In addition, PCT publications WO 2000/71129 and WO 2004/013145, which are assigned to the present assignee, disclose pyrrolotriazine compounds useful as VEGF receptor inhibitors. The present invention relates to a new class of pyrrolotriazines found to be effective inhibitors of protein kinases, particularly the CK2 kinase. These novel compounds are provided to be useful as pharmaceuticals with desirable stability, bioavailability, therapeutic index and toxicity values that are important to their drugability.

SUMMARY OF THE INVENTION

The invention is directed to fused heterocyclic compounds of Formula (I) or stereoisomers, tautomers, pharmaceutically acceptable salts, solvates or prodrugs thereof, which inhibit protein kinase enzymes, especially protein kinase CK2 for the treatment of cancer.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides methods for inhibiting the activity of protein kinase CK2 comprising administering to a host in need of such treatment a therapeutically effective amount of at least one of the compounds of the present invention or stereoisomers, tautomers, pharmaceutically acceptable salts, solvates, or prodrugs thereof.

The present invention also provides methods for inhibiting angiogenesis or treating cancers comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, in preparing a medicament for the treatment of cancer in a human patient, particularly a cancer receptive to treatment via inhibition of the CK2 enzyme.

These and other features of the invention will be set forth in the expanded form as the disclosure continues.

DETAILED DESCRIPTION OF THE INVENTION

The invention provides for novel pyrrolotriazine compounds useful as therapeutic agents, pharmaceutical compositions employing such novel compounds and for methods of using such compounds.

In accordance with the invention, there are disclosed compounds of Formula (I) including enantiomers, diastereomers, tautomers, pharmaceutically-acceptable salts, prodrugs, hydrates, or solvates thereof,

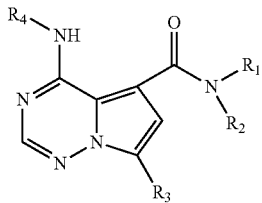

(I)

wherein $R_1$ is selected from H, $NR_aR_a$, $C_{1-6}$alkyl substituted with 0-5 $R_{1a}$, $C_{2-6}$alkenyl substituted with 0-5 $R_{1a}$, $C_{2-6}$alkynyl substituted with 0-5 $R_{1a}$, —(CHR)$_r$-carbocyclyl substituted with 0-5 $R_{1a}$, —(CHR)$_r$-heterocyclyl substituted with 0-5 $R_{1a}$;

$R_{1a}$, at each occurrence, is independently selected from $C_{1-6}$alkyl substituted with 0-5 $R_e$, $C_{2-6}$alkenyl substituted with 0-5 $R_e$, $C_{2-6}$alkynyl substituted with 0-5 $R_e$, $C_{1-6}$haloalkyl, F, Cl, Br, $NO_2$, CN, =O, —(CHR)$_r$OH, —(CHR)$_r$SH, (CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$NR$_a$R$_a$, —(CHR)$_r$NR$_a$C(O)R$_d$, —(CHR)$_r$NR$_a$C(O)OR$_b$, —(CHR)$_r$NR$_a$C(O)(CRR)$_r$OC(O)NR$_a$R$_a$, —(CHR)$_r$NR$_a$C(O)(CRR)$_r$NR$_a$R$_a$, —(CHR)$_r$NR$_a$C(O)(CRR)$_r$NR$_a$C(O)OR$_d$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$-carbocyclyl substituted with 0-5 $R_e$ and —(CHR)$_r$-heterocyclyl substituted with 0-5 $R_e$;

$R_2$ is selected from H and $C_{1-6}$alkyl substituted with 0-3 $R_{2a}$;

$R_{2a}$ is selected from F, Cl, and Br;

alternatively, $R_1$ and $R_2$ are taken together with the nitrogen atom to which they are attached to form a heterocyclyl substituted with 0-5 $R_{1a}$;

$R_3$ is selected from aryl substituted with 0-5 $R_{3a}$, and heteroaryl substituted with 0-5 $R_{1a}$;

$R_{3a}$, at each occurrence, is independently selected from $C_{1-6}$alkyl, $C_{2-6}$alkenyl, $C_{2-6}$alkynyl, $C_{1-6}$haloalkyl, F, Cl, Br, $NO_2$, CN, —OH, —SH, —OR$_b$, —S(O)$_p$R$_b$, C(O)R$_d$, NR$_a$R$_a$, —C(O)NR$_a$R$_a$, —NR$_a$C(O)R$_d$, —NR$_a$C(O)OR$_b$, —OC(O)NR$_a$R$_a$, —C(O)OR$_d$, —S(O)$_p$NR$_a$R$_a$, —NR$_a$S(O)$_p$R$_b$;

$R_4$ is selected from H, $C_{1-6}$alkyl, and $C_{3-6}$cycloalkyl;

$R_a$, at each occurrence, is independently selected from H, $NH_2$, $C_{1-6}$alkyl substituted with 0-3 $R_e$, $C_{2-6}$alkenyl substituted with 0-3 $R_e$, $C_{2-6}$alkynyl substituted with 0-3 $R_e$, $C_{1-6}$haloalkyl, —(CH$_2$)$_r$OH, (CH$_2$)$_r$-carbocyclyl substituted with 0-3 $R_e$, and (CH$_2$)$_r$-heterocyclyl substituted with 0-3 $R_e$, or $R_a$ and $R_a$ together with the nitrogen atom to which they are attached form a heterocyclyl substituted with 0-3 $R_e$;

$R_b$, at each occurrence, is independently selected from $C_{1-6}$alkyl substituted with 0-3 $R_e$, $C_{1-6}$haloalkyl, $C_{2-6}$alkenyl substituted with 0-3 $R_e$, $C_{2-6}$alkynyl substituted with 0-3 $R_e$, —(CH$_2$)$_r$-carbocyclyl substituted with 0-3 $R_e$, and —(CH$_2$)$_r$-heterocyclyl substituted with 0-3 $R_e$;

$R_d$, at each occurrence, is independently selected from H, $C_{1-6}$alkyl substituted with 0-3 $R_e$, $C_{1-6}$haloalkyl, $C_{2-6}$alkenyl substituted with 0-3 $R_e$, $C_{2-6}$alkynyl substituted with 0-3 $R_e$, —(CH$_2$)$_r$-carbocyclyl substituted with 0-3 $R_e$, and —(CH$_2$)$_r$-heterocyclyl substituted with 0-3 $R_e$;

$R_e$, at each occurrence, is independently selected from $C_{1-6}$alkyl, $C_{2-6}$alkenyl, $C_{2-6}$alkynyl, (CH$_2$)$_r$C$_{3-6}$cycloalkyl, F, Cl, Br, CN, $NO_2$, $CO_2H$, =O, —C(O)NR$_f$R$_f$, (CF$_2$)$_r$CF$_3$, —(CH$_2$)$_r$OC$_{1-5}$alkyl, —(CH$_2$)$_r$OH, SH, —(CH$_2$)$_r$SC$_{1-5}$alkyl, —(CH$_2$)$_r$NR$_f$R$_f$, —(CH$_2$)$_r$phenyl, and (CH$_2$)$_r$heterocyclyl;

$R_f$, at each occurrence, is independently selected from H, $C_{1-5}$alkyl, $C_{3-6}$cycloalkyl, and phenyl;

R, at each occurrence, is independently selected from H, —(CH$_2$)$_r$OH, $C_{1-6}$alkyl, $C_{1-6}$haloalkyl, and —(CH$_2$)$_r$-aryl;

p, at each occurrence, is independently selected from 0, 1, and 2; and r, at each occurrence, is independently selected from 0, 1, 2, 3, and 4.

In another aspect, there are disclosed compounds of Formula (I) including enantiomers, diastereomers, tautomers, pharmaceutically-acceptable salts, prodrugs, hydrates, or solvates thereof, wherein $R_3$ is selected from aryl substituted with 0-4 $R_{3a}$ and heteroaryl substituted with 0-4 $R_{3a}$, wherein said heteroaryl comprises carbon atoms and 1-4 heteroatoms selected from N, O, and S(O)$_p$; and $R_{3a}$, at each occurrence, is independently selected from $C_{1-6}$alkyl, $C_{2-6}$alkenyl, $C_{2-6}$alkynyl, $C_{1-6}$haloalkyl, F, Cl, Br, $NO_2$, CN, —OH, —SH, —OR$_b$, —C(O)R$_d$, —NR$_a$R$_a$, C(O)NR$_a$R$_a$, and —C(O)OR$_d$.

In another embodiment, there are disclosed compounds of Formula (I) including enantiomers, diastereomers, tautomers, pharmaceutically-acceptable salts, prodrugs, hydrates, or solvates thereof, wherein $R_3$ is heteroaryl selected from pyridyl, pyrimidinyl, pyrazinyl, pyridazinyl, triazinyl, furyl, quinolyl, isoquinolyl, thienyl, imidazolyl, thiazolyl, indolyl, pyrrolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane, each of which is substituted with 0-3 $R_{3a}$.

In another embodiment, there are disclosed compounds of Formula (I) including enantiomers, diastereomers, tautomers, pharmaceutically-acceptable salts, prodrugs, hydrates, or solvates thereof, wherein $R_1$ is selected from —(CHR)$_r$-carbocyclyl substituted with 0-4 $R_{1a}$, —(CHR)$_r$-heterocyclyl substituted with 0-4 $R_{1a}$;

$R_{1a}$, at each occurrence, is independently selected from $C_{1-4}$alkyl substituted with 0-4 $R_e$, $C_{2-6}$alkenyl substituted with 0-4 $R_e$, $C_{2-4}$alkynyl substituted with 0-4 $R_e$, $C_{1-4}$haloalkyl, F, Cl, Br, $NO_2$, CN, =O, —(CHR)$_r$OH, —(CHR)$_r$SH, (CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$NR$_a$R$_a$, —(CHR)$_r$NR$_a$C(O)R$_d$, —(CHR)$_r$NR$_a$C(O)OR$_b$, —(CHR)$_r$NR$_a$C(O)(CRR)$_r$OC(O)NR$_a$R$_a$, —(CHR)$_r$NR$_a$C(O)(CRR)$_r$NR$_a$R$_a$, —(CHR)$_r$NR$_a$C(O)(CRR)$_r$NC(O)OR$_d$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$N-

$R_aS(O)_pR_b$, —(CHR)$_r$-carbocyclyl substituted with 0-4 $R_e$ and —(CHR)$_r$-heterocyclyl substituted with 0-4 $R_e$;

$R_a$, at each occurrence, is independently selected from H, $NH_2$, $C_{1-6}$alkyl substituted with 0-3 $R_e$, $C_{2-6}$alkenyl substituted with 0-3 $R_e$, $C_{2-6}$alkynyl substituted with 0-3 $R_e$, —(CH$_2$)$_r$OH, (CH$_2$)$_r$-carbocyclyl substituted with 0-3 $R_e$, and (CH$_2$)$_r$heterocyclyl substituted with 0-3 $R_e$, or $R_a$, and $R_a$ together with the nitrogen atom to which they are attached form a heterocyclyl substituted with 0-3 $R_e$;

$R_b$, at each occurrence, is independently selected from $C_{1-6}$alkyl substituted with 0-3 $R_e$, $C_{2-6}$alkenyl substituted with 0-3 $R_e$, $C_{2-6}$alkynyl substituted with 0-3 $R_e$, —(CH$_2$)$_r$carbocyclyl substituted with 0-3 $R_e$, and —(CH$_2$)$_r$heterocyclyl substituted with 0-3 $R_e$;

$R_d$, at each occurrence, is independently selected from H, $C_{1-6}$alkyl substituted with 0-3 $R_e$, $C_{2-6}$alkenyl substituted with 0-3 $R_e$, $C_{2-6}$alkynyl substituted with 0-3 $R_e$, —(CH$_2$)$_r$-carbocyclyl substituted with 0-3 $R_e$, and —(CH$_2$)$_r$-heterocyclyl substituted with 0-3 $R_e$;

$R_e$, at each occurrence, is independently selected from $C_{1-6}$alkyl, $C_{2-6}$alkenyl, $C_{2-6}$alkynyl, (CH$_2$)$_r$$C_{3-6}$cycloalkyl, F, Cl, Br, CN, NO$_2$, CO$_2$H, =O, —C(O)NR$_f$R$_f$, —(CH$_2$)$_r$OC$_{1-5}$alkyl, —(CH$_2$)$_r$OH, SH, —(CH$_2$)$_r$SC$_{1-5}$alkyl, —(CH$_2$)$_r$NR$_f$R$_f$, —(CH$_2$)$_r$phenyl, and (CH$_2$)$_r$heterocyclyl;

$R_f$, at each occurrence, is independently selected from H, $C_{1-4}$alkyl, and phenyl;

R, at each occurrence, is independently selected from H, —(CH$_2$)$_r$OH, $C_{1-6}$alkyl, $C_{1-6}$haloalkyl, and (CH$_2$)$_r$-aryl;

p, at each occurrence, is independently selected from 0, 1, and 2; and r, at each occurrence, is independently selected from 0, 1, 2, 3, and 4.

In another embodiment, there are disclosed compounds of Formula (I) including enantiomers, diastereomers, tautomers, pharmaceutically-acceptable salts, prodrugs, hydrates, or solvates thereof, wherein $R_1$ is selected from —(CHR)$_r$-aryl substituted with 0-3 $R_{1a}$ and —(CHR)$_r$—C$_{3-7}$cycloalkyl substituted with 0-3 $R_{1a}$.

In another embodiment, there are disclosed compounds of Formula (I) including enantiomers, diastereomers, tautomers, pharmaceutically-acceptable salts, prodrugs, hydrates, or solvates thereof, wherein $R_1$ is —(CH$_2$)$_r$—C$_{3-7}$cycloalkyl substituted with 0-3 $R_{1a}$;

$R_{1a}$, at each occurrence, is independently selected from $C_{1-4}$alkyl substituted with 0-3 $R_e$, =O, —(CHR)$_r$OH, —OR$_b$, —C(O)R$_d$, —NR$_a$R$_a$, —C(O)NR$_a$R$_a$, —NHC(O)R$_d$, —NHC(O)OR$_b$, —NHC(O)(CRR)$_r$OC(O)NR$_a$R$_a$, —NHC(O)(CRR)$_r$NR$_a$R$_a$, —NHC(O)(CRR)$_r$NHC(O)OR$_d$, —C(O)OR$_d$, —S(O)$_2$NR$_a$R$_a$, —NHS(O)$_2$R$_b$, aryl substituted with 0-3 $R_e$ and heterocyclyl substituted with 0-3 $R_e$;

$R_a$, at each occurrence, is independently selected from H, $C_{1-6}$alkyl substituted with 0-3 $R_e$, —(CH$_2$)$_r$-aryl substituted with 0-3 $R_e$, —(CH$_2$)$_r$—C$_{3-6}$cycloalkyl substituted with 0-3 $R_e$, and —(CH$_2$)$_r$-heterocyclyl substituted with 0-3 $R_e$, or $R_a$ and $R_a$ together with the nitrogen atom to which they are attached form a heterocyclyl substituted with 0-3 $R_e$;

$R_b$, at each occurrence, is independently selected from $C_{1-6}$alkyl substituted with 0-3 $R_e$, —(CH$_2$)$_r$-aryl substituted with 0-3 $R_e$, —(CH$_2$)$_r$—C$_{3-6}$cycloalkyl substituted with 0-3 $R_e$, and —(CH$_2$)$_r$heterocyclyl substituted with 0-3 $R_e$;

$R_d$, at each occurrence, is independently selected from H, $C_{1-6}$alkyl substituted with 0-3 $R_e$, —(CH$_2$)$_r$-aryl substituted with 0-3 $R_e$, —(CH$_2$)$_r$—C$_{3-6}$cycloalkyl substituted with 0-3 $R_e$, and —(CH$_2$)$_r$heterocyclyl substituted with 0-3 $R_e$;

$R_e$, at each occurrence, is independently selected from $C_{1-6}$alkyl, (CH$_2$)$_r$C$_{3-6}$cycloalkyl, F, Cl, Br, CN, CO$_2$H, =O, —C(O)NR$_f$R$_f$, —(CH$_2$)$_r$OC$_{1-5}$alkyl, —(CH$_2$)$_r$OH, —(CH$_2$)$_r$NR$_f$R$_f$, —(CH$_2$)$_r$phenyl, and (CH$_2$)$_r$heterocyclyl;

$R_f$, at each occurrence, is independently selected from H and $C_{1-4}$alkyl;

R, at each occurrence, is independently selected from H and $C_{1-4}$alkyl; and r, at each occurrence, is independently selected from 0, 1, 2, and 3.

In another embodiment, there are disclosed compounds of Formula (I) including enantiomers, diastereomers, tautomers, pharmaceutically-acceptable salts, prodrugs, hydrates, or solvates thereof, wherein $R_1$ is —(CHR)$_r$-aryl substituted with 0-3 $R_{1a}$;

$R_{1a}$, at each occurrence, is independently selected from $C_{1-4}$alkyl substituted with 0-3 $R_e$, CN, —(CHR)$_r$OH, (CHR)$_r$OR$_b$, —(CHR)$_r$S(O)$_2$R$_b$, —(CHR)$_r$S(O)$_2$NR$_a$R$_a$, —(CHR)$_r$NR$_a$S(O)$_2$R$_b$, aryl substituted with 0-3 $R_e$ and —(CH$_2$)$_r$-heterocyclyl substituted with 0-3 $R_e$;

$R_a$, at each occurrence, is independently selected from H and $C_{1-6}$alkyl substituted with 0-3 $R_e$;

$R_b$, at each occurrence, is independently selected from $C_{1-6}$alkyl substituted with 0-3 $R_e$, —(CH$_2$)$_r$-aryl substituted with 0-3 $R_a$, —(CH$_2$)$_r$—C$_{3-6}$cycloalkyl substituted with 0-3 $R_e$, and —(CH$_2$)$_r$heterocyclyl substituted with 0-3 $R_e$;

$R_e$, at each occurrence, is independently selected from $C_{1-6}$alkyl, (CH$_2$)$_r$C$_{3-6}$cycloalkyl, F, Cl, Br, CN, CO$_2$H, =O, —(CH$_2$)$_r$OC$_{1-5}$alkyl, —(CH$_2$)$_r$OH, —(CH$_2$)$_r$phenyl, and (CH$_2$)$_r$heterocyclyl;

R, at each occurrence, is independently selected from H, OH, and $C_{1-4}$alkyl; and r, at each occurrence, is independently selected from 0, 1, 2, and 3.

In another embodiment, there are disclosed compounds of Formula (I) including enantiomers, diastereomers, tautomers, pharmaceutically-acceptable salts, prodrugs, hydrates, or solvates thereof, wherein $R_1$ is selected from —(CHR)$_r$-heterocyclyl substituted with 0-3 $R_{1a}$;

$R_{1a}$, at each occurrence, is independently selected from $C_{1-4}$alkyl substituted with 0-3 $R_e$, CN, =O, —(CH$_2$)$_r$OH, (CH$_2$)$_r$OR$_b$, —(CH$_2$)$_r$S(O)$_p$R$_b$, —(CH$_2$)$_r$C(O)R$_d$, —(CH$_2$)$_r$NR$_a$R$_a$, —(CH$_2$)$_r$C(O)NR$_a$R$_a$, —(CH$_2$)$_r$C(O)OR$_d$, —(CH$_2$)$_r$S(O)$_p$NR$_a$R$_a$, —(CHR)$_r$NR$_a$S(O)$_p$R$_b$, —(CHR)$_r$-aryl substituted with 0-3 $R_e$ and —(CHR)$_r$-heterocyclyl substituted with 0-3 $R_e$;

$R_a$, at each occurrence, is independently selected from H, $NH_2$, $C_{1-6}$alkyl substituted with 0-3 $R_e$, or $R_a$ and $R_a$ together with the nitrogen atom to which they are attached form a heterocyclyl substituted with 0-3 $R_e$;

$R_b$, at each occurrence, is independently selected from $C_{1-6}$alkyl substituted with 0-3 $R_e$, —(CH$_2$)$_r$carbocyclyl substituted with 0-3 $R_e$, and —(CH$_2$)$_r$heterocyclyl substituted with 0-3 $R_e$;

$R_d$, at each occurrence, is independently selected from H, $C_{1-6}$alkyl substituted with 0-3 $R_e$, —(CH$_2$)$_r$—C$_{3-6}$cycloalkyl substituted with 0-3 $R_e$, and —(CH$_2$)$_r$-heterocyclyl substituted with 0-3 $R_e$;

$R_e$, at each occurrence, is independently selected from $C_{1-6}$alkyl, CN, NO$_2$, CO$_2$H, =O, —C(O)NH$_2$, —(CH$_2$)$_r$OC$_{1-5}$alkyl, —(CH$_2$)$_r$OH, SH, —(CH$_2$)$_r$SC$_{1-5}$alkyl, —(CH$_2$)$_r$NH$_2$, —(CH$_2$)$_r$phenyl, and (CH$_2$)$_r$heterocyclyl;

R, at each occurrence, is independently selected from H, —(CH$_2$)$_r$OH, $C_{1-4}$alkyl, and —(CH$_2$)$_r$-aryl;

p, at each occurrence, is independently selected from 0, 1, and 2; and r, at each occurrence, is independently selected from 0, 1, 2, 3, and 4.

In another embodiment, there are disclosed compounds of Formula (I) including enantiomers, diastereomers, tautomers, pharmaceutically-acceptable salts, prodrugs, hydrates, or solvates thereof, wherein $R_1$ and $R_2$ are taken together with the nitrogen atom to which they are attached to form a heterocyclyl substituted with 0-3 $R_{1a}$;

$R_{1a}$, at each occurrence, is independently selected from $C_{1-4}$alkyl substituted with 0-3 $R_e$, —$(CH_2)_r$OH, —$(CH_2)_r$S$(O)_pR_b$, —$(CH_2)_rC(O)R_d$, —$(CH_2)_rNR_aR_a$, —$(CH_2)_rC(O)NR_aR_a$, —$(CH_2)_rNHC(O)R_d$, —$(CH_2)_rNHC(O)OR_b$;

$R_a$, at each occurrence, is independently selected from H and $C_{1-6}$alkyl substituted with 0-3 $R_e$;

$R_b$, at each occurrence, is independently selected from $C_{1-6}$alkyl substituted with 0-3 $R_e$, —$(CH_2)_r$-aryl substituted with 0-3 $R_e$, —$(CH_2)_r$—$C_{3-6}$cycloalkyl substituted with 0-3 $R_e$, and —$(CH_2)_r$heterocyclyl substituted with 0-3 $R_e$;

$R_d$, at each occurrence, is independently selected from H, $C_{1-6}$alkyl substituted with 0-3 $R_e$, —$(CH_2)_r$-aryl substituted with 0-3 $R_e$, —$(CH_2)_r$—$C_{3-6}$cycloalkyl substituted with 0-3 $R_e$, and —$(CH_2)_r$heterocyclyl substituted with 0-3 $R_e$;

$R_e$, at each occurrence, is independently selected from $C_{1-6}$alkyl, $(CH_2)_rC_{3-6}$cycloalkyl, F, Cl, Br, CN, $CO_2H$, =O, —$(CH_2)_rOC_{1-5}$alkyl, —$(CH_2)_r$OH, —$(CH_2)_r$phenyl, and $(CH_2)_r$heterocyclyl; and r, at each occurrence, is independently selected from 0, 1, 2, and 3.

In another embodiment, there are disclosed compounds of Formula (I) including enantiomers, diastereomers, tautomers, pharmaceutically-acceptable salts, prodrugs, hydrates, or solvates thereof, wherein $R_1$ is $C_{1-5}$alkyl substituted with 0-3 $R_{1a}$;

$R_{1a}$, at each occurrence, is independently selected from $C_{1-4}$alkyl substituted with 0-3 $R_e$, —$(CH_2)_r$OH, —$(CH_2)_rC(O)OR_d$, —$(CH_2)_rNR_aR_a$, —$(CH_2)_rC(O)NR_aR_a$, —$(CH_2)_rNHC(O)R_d$, —$(CH_2)_rNHC(O)OR_b$, and —$(CH_2)_rNHS(O)_2R_b$;

$R_a$, at each occurrence, is independently selected from H and $C_{1-6}$alkyl substituted with 0-3 $R_e$;

$R_b$, at each occurrence, is independently selected from $C_{1-6}$alkyl substituted with 0-3 $R_e$, —$(CH_2)_r$-aryl substituted with 0-3 $R_e$, —$(CH_2)_r$—$C_{3-6}$cycloalkyl substituted with 0-3 $R_e$, and —$(CH_2)_r$heterocyclyl substituted with 0-3 $R_e$;

$R_d$, at each occurrence, is independently selected from H, $C_{1-6}$alkyl substituted with 0-3 $R_e$, —$(CH_2)_r$-aryl substituted with 0-3 $R_e$, —$(CH_2)_r$—$C_{3-6}$cycloalkyl substituted with 0-3 $R_e$, and —$(CH_2)_r$heterocyclyl substituted with 0-3 $R_e$;

$R_e$, at each occurrence, is independently selected from $C_{1-6}$alkyl, $(CH_2)_rC_{3-6}$cycloalkyl, F, Cl, Br, CN, $CO_2H$, =O, —$(CH_2)_rOC_{1-5}$alkyl, —$(CH_2)_r$OH, —$(CH_2)_r$phenyl, and $(CH_2)_r$heterocyclyl; and r, at each occurrence, is independently selected from 0, 1, 2, and 3.

All aspects of the compounds, including individual variable definitions, may be combined with other aspects to form additional compounds. For example, in one embodiment of Formula (I), $R_1$ is hydrogen and $R_3$ is aryl or heteroaryl substituted with 0-3 $R_{3a}$. In another embodiment, $R_1$ is $C_{3-7}$cycloalkyl and $R_3$ is aryl or heteroaryl substituted with 0-3 $R_{3a}$. In still another embodiment, $R_1$ is aryl and $R_3$ is aryl or heteroaryl substituted with 0-3 $R_{3a}$. In still another embodiment, $R_1$ is heterocyclyl and $R_3$ is aryl or heteroaryl substituted with 0-3 $R_{3a}$. In still another embodiment, $R_1$ is $C_{1-5}$alkyl substituted with 0-3 $R_{1a}$ and $R_3$ is aryl or heteroaryl substituted with 0-3 $R_{3a}$.

Thus, in one embodiment, $R_1$ and $R_2$ can be both hydrogen.

In another embodiment, $R_1$ is hydrogen and $R_2$ is $C_{1-4}$alkyl. Non-limiting examples of the alkyl include methyl, ethyl, propyl, and butyl.

In another embodiment, $R_1$ and $R_2$ are taken together with the nitrogen atom to which they are attached to form a 4-, 5-, or 6-membered saturated heterocyclyl substituted with 1-2 $R_{1a}$ wherein said $R_{1a}$ is selected from $C_{1-4}$alkyl substituted with 0-3 $R_e$, —$(CH_2)_{0-1}$OH, —$(CH_2)_{0-1}NH_2$, and —$(CH_2)_{0-1}$NHC(O)O—$C_{1-4}$alkyl.

In another embodiment, $R_3$ is selected from aryl substituted with 0-3 $R_{3a}$ and heteroaryl substituted with 0-3 $R_{3a}$, wherein said heteroaryl comprises carbon atoms and 1-4 heteroatoms selected from N, O, and $S(O)_p$.

In another embodiment, $R_3$ is pyridyl substituted with 0-3 $R_{3a}$ wherein $R_{3a}$, at each occurrence, is independently selected from $C_{1-6}$alkyl, CN, —OH, —O—$C_{1-4}$alkyl, —$C(O)NR_aR_a$, and —C(O)OH.

In another embodiment, $R_1$ and $R_2$ are taken together with the nitrogen atom to which they are attached to form a 4-, 5-, or 6-membered saturated heterocyclyl substituted with 1-2 $R_{1a}$ wherein said $R_{1a}$ is selected from $C_{1-4}$alkyl substituted with 0-3 $R_e$, —$(CH_2)_{0-1}$OH, —$(CH_2)_{0-1}NH_2$, and —$(CH_2)_{0-1}$NHC(O)O—$C_{1-4}$alkyl, $R_3$ is pyridine optionally substituted with —$OC_{1-4}$alkyl.

In another embodiment, $R_1$ is —$(CH_2)_{0-2}$—$C_{3-7}$Cycloalkyl substituted with 0-3 $R_{1a}$, wherein said cycloalkyl is selected from cyclopropyl, cyclobutyl, cyclopentyl, cyclohexyl, and cycloheptyl.

In another embodiment, $R_1$ is —$(CH_2)_{0-2}$—$C_{3-7}$Cycloalkyl substituted with 0-3 $R_{1a}$, wherein said cycloalkyl is selected from cyclopropyl, cyclobutyl, cyclopentyl, cyclohexyl, and cycloheptyl; $R_{1a}$ is selected from —$(CH_2)_{0-1}$OH, =O, —$C(O)R_d$, —$NHC(O)R_d$, —$NHC(O)OR_b$, aryl substituted with 0-3 $R_e$, —$NR_aR_a$, —$C(O)OR_d$, —$C(O)NR_aR_a$, —$NHC(O)(CRR)_rNR_aR_a$, —$OR_b$, heterocyclyl substituted with 0-3 $R_e$, $C_{1-4}$alkyl substituted with 0-3 $R_e$, —$NHC(O)(CRR)_rOC(O)NR_aR_a$, —$NHC(O)(CRR)_rNHC(O)OR_d$, —$S(O)_2NR_aR_a$, and —$NHS(O)_2R_b$; $R_3$ is pyridine optionally substituted with —$OC_{1-4}$alkyl.

In another embodiment, $R_1$ is —$(CH_2)_{0-2}$—$C_{3-7}$Cycloalkyl, $R_3$ is aryl substituted with 0-3 $R_{3a}$, wherein $R_{3a}$, at each occurrence, is independently selected from $C_{1-6}$alkyl, CN, —OH, —O—$C_{1-4}$alkyl, —$C(O)NR_aR_a$, and —C(O)OH.

In another embodiment, $R_1$ is —$(CH_2)_{0-2}$-aryl substituted with 0-3 $R_{1a}$; $R_{1a}$ is selected from CN, —$(CH_2)_{0-1}$OH, —$C(O)R_d$, —$NHC(O)R_d$, —$NHC(O)OR_b$, aryl substituted with 0-3 $R_e$, —$NR_aR_a$, —$C(O)OR_d$, —$C(O)NR_aR_a$, —$NHC(O)(CRR)_rNR_aR_a$, —$OR_b$, heterocyclyl substituted with 0-3 $R_e$, $C_{1-4}$alkyl substituted with 0-3 $R_e$, —$NHC(O)(CRR)_rOC(O)NR_aR_a$, —$NHC(O)(CRR)NHC(O)OR_d$, —$S(O)_2NR_aR_a$, and —$NHS(O)_2R_b$; $R_3$ is pyridine optionally substituted with —$OC_{1-4}$alkyl.

In another embodiment, $R_1$ is —$(CH_2)_{0-2}$-aryl substituted with 0-3 $R_{1a}$; $R_{1a}$ is selected from —$(CH_2)_{0-1}$OH, —$OC_{1-4}$alkyl substituted with 0-3 $R_e$, heterocyclyl substituted with 0-3 $R_e$, —$S(O)_2NR_aR_a$, —$NHS(O)_2R_b$, and $S(O)_2R_b$; $R_3$ is pyridine optionally substituted with —$OC_{1-4}$alkyl. Non-limiting examples of the heterocyclyl include pyrrolidine, imidazole, pyrazole, oxazole, oxadiazole, thiazole, triazole, tetrazole, piperazine, piperidine, and morpholine.

In another embodiment, $R_1$ is —$(CH_2)_{0-2}$-heterocyclyl substituted with 0-3 $R_{1a}$. Non-limiting examples of heterocyclyl include pyridinyl, furanyl, thienyl, pyrrolyl, pyrazolyl, pyrazinyl, pyrrolidinyl, imidazolyl, imidazolinyl, oxazolidinyl, isoxazolinyl, thiazolidinyl, isothiazolidinyl, tetrahydrofuranyl, piperidyl, piperazinyl, piperidonyl, tetrahydropyranyl, morpholinyl, azepanyl, and naphthyridinyl.

In another embodiment, the present invention provides a compound selected from the group consisting of Examples 1-197 and any subset list of the compounds within the group.

The compounds of Formula (I) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for Formula (I) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

It should further be understood that solvates (e.g., hydrates) of the compounds of Formula (I) are also within the scope of the invention. Methods of solvation are generally known in the art. The inventive compounds may either be in the free or hydrate form.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The present invention is also intended to include all isotopes of atoms occurring in the present compounds. Isotopes include those having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the Formula (I) may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:
a) *Design of Prodrugs*, H. Bundgaard, ed., Elsevier (1985), and *Methods in Enzymology*, 112:309-396, K. Widder et al., eds., Academic Press (1985);
b) Bundgaard, H., Chapter 5, "Design and Application of Prodrugs," *A Textbook of Drug Design and Development*, pp. 113-191, P. Krosgaard-Larsen et al., eds., Harwood Academic Publishers (1991); and
c) Bundgaard, H., *Adv. Drug Deliv. Rev.*, 8:1-38 (1992).

DEFINITIONS

The following are definitions of terms used in this specification and appended claims. The initial definition provided for a group or term herein applies to that group or term throughout the specification and claims, individually or as part of another group, unless otherwise indicated.

In accordance with a convention used in the art,

is used in structural formulas herein to depict the bond that is the point of attachment of the moiety or substituent to the core or backbone structure.

A dash "—" that is not between two letters or symbols is used to indicate a point of attachment for a substituent. For example, —CONH$_2$ is attached through the carbon atom.

As used herein, the term "alkyl" or "alkylene" is intended to include both branched and straight-chain saturated aliphatic hydrocarbon groups having the specified number of carbon atoms. For example, "C$_{1-10}$ alkyl" (or alkylene), is intended to include C$_1$, C$_2$, C$_3$, C$_4$, C$_5$, C$_6$, C$_7$, C$_8$, C$_9$, and C$_{10}$ alkyl groups. Additionally, for example, "C$_1$-C$_6$alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "halogen" or "halo" refers to fluorine (F), chlorine (Cl), bromine (Br) and iodine.

"Haloalkoxy" or "haloalkyloxy" represents a haloalkyl group as defined above with the indicated number of carbon atoms attached through an oxygen bridge. For example, "$C_{1\text{-}6}$haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle," "carbocyclic residue," or "carbocyclyl" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0] bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge. Preferred carbocycles, unless otherwise specified, are cyclopropyl, cyclobutyl, cyclopentyl, cyclohexyl, phenyl, and indanyl. When the term "carbocycle," "carbocyclic residue," or "carbocyclyl" is used, it is intended to include "aryl".

The term "aryl" refers to monocyclic, bicyclic, tricyclic aromatic hydrocarbon groups having 6 to 15 carbon atoms in the ring portion, such as phenyl, naphthyl, biphenyl and diphenyl groups, each of which may be substituted. Aryl groups which are bicyclic or tricyclic must include at least one fully aromatic ring but the other fused ring or rings may be aromatic or non-aromatic. When an aryl is substituted with a further heterocyclic ring, said ring may be attached to the aryl through a carbon atom or a heteroatom and said ring in turn is optionally substituted with one to two substituents as valence allows.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

An "alkylidene" group refers to an alkylene group consisting of at least two carbon atoms and at least one carbon-carbon double bond. Substituents on this group include those in the definition of "substituted alkyl".

The term "cycloalkyl" refers to an optionally substituted, saturated cyclic hydrocarbon ring systems, preferably containing 1 to 3 rings and 3 to 7 carbons per ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the term "heterocycle," "heterocyclyl," "heterocyclic ring" or "heterocyclic group" is intended to mean a stable 4-, 5-, 6-, or 7-membered monocyclic or 7-, 8-, 9-, 10-, 11-, 12-, 13-, or 14-membered bicyclic heterocyclic ring which is saturated, partially unsaturated or fully unsaturated or aromatic, and which consists of carbon atoms and 1, 2, 3 or 4 heteroatoms independently selected from N, O, and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle," "heterocyclyl," "heterocyclic ring" or "heterocyclic group" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and S(O)$_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, dihydroisoquinolinyl, tetrahydroquinolinyl, isoquinolinyl, benzimidazolyl, benzopyranyl, benzoxazinyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and the like.

Exemplary tricyclic heteroaryl groups include carbazolyl, benzidolyl, phenanthrollinyl, acridinyl, phenanthridinyl, xanthenyl and the like.

The term "heteroatoms" shall include oxygen, sulfur and nitrogen.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

When any variable occurs more than one time in any constituent or formula for a compound, its definition at each occurrence is independent of its definition at every other occurrence. Thus, for example, if a group is shown to be substituted with 0-3 $R_e$, then said group may optionally be substituted with up to three $R_e$ groups and $R_e$ at each occurrence is selected independently from the definition of $R_e$. Also, combinations of substituents and/or variables are permissible only if such combinations result in stable compounds.

UTILITY

The compounds of the invention may be used to modulate kinase activities. Types of kinases include, but are not limited to, AAK1, ABL, ACK, ACTR2, ACTR2B, ADCK3, ADCK4, AKT1, AKT2, AKT3, ALK, ALK1, ALK2, ALK4, AMPKA1, AMPKA2, ARG, AURA, AURB, AURC, AXL, BCR-ABL, BIKE, BLK, BMPR1A, BMX, BRAF, BRSK2, BRK, BTK, CAMK1A, CAMK2A, CAMK2B, CAMK1D, CAMK2D, CAMKIG, CAMK2G, CAMKK1, CAMKK2, CDK1, CDK2, CDK5, CHK2, CK1A2, CK1D, CK1E, CK1G1, CK1G2, CK2A1, CK2A2, CLK1, CLK2, CLK3, CLK4, CSK, DAPK2, DAPK3, DCAMKL3, DDR2, DMPK1, DRAK1, DRAK2, DYRK1, DYRK2, EGFR, EPHA1, EPHA2, EPHA3, EPHA4, EPHA5, EPHA6, EPHA7, EPHA8, EPHB1, EPHB2, EPHB3, EPHB4, ERK1, ERK2, FAK, FER, FES, FGFR1, FGFR2, FGFR3, FGFR4, FGR, FLT1, FLT3, FLT4, FMS, FRK, FYN, FUSED, GAK, GCN2, GPRK4, GPRK5, GPRK6, GSK3A, GSK3B, HCK, HPK1, HER2/ERBB2, HER4/ERBB4, HH498, IGF1R, IKKα, IKKβ, INSR, IRR, IRAK4, ITK, JAK1, JAK2, JAK3, JNK1, JNK2, JNK3, KDR, KHS1, KHS2, KIT, LCK, LIMK1, LIMK2, LKB1, LOK, LTK, LYN, MAP3K4, MAP3K5, MAPK1, MAPKAP-K2, MARK1, MARK2, MARK4, MEK1, MER, MET, MKK4, MKK6, MLK3, MNK2, MPSK1, MRCKA, MSK1, MSK2, MST1, MST2, MST3, MST4, MUSK, MYT1, NDR2, NEK2, NEK6, NEK7, NEK9, NLK, P38A, P38B, P38G, PAK1, PAK2, PAK3, PAK-4, PAK5, PAK6, PCTAIRE1, PDGFRA, PDG-FRB, PDK1, PHKG1, PHKG2, PIM1, PIM2, PKA, PKACA, PKACB, PKCA, PKCD, PKCH, PKCI, PKCT, PKCZ, PKD2, PKG1, PKG2, PKN2, PLK1, PLK3, PLK4, PRKX, PYK2, QIK, RAF1, RET, RIPK2, ROCK-I, ROCK-II, RON, ROS, RSK1, RSK2, RSK4, SAPK2a, SAPK2b, SAPK3, SAPK4, SGK, SIK, SLK, SKMLCK, SRC, SRPK1, STK33, SYK, TESK1, TGFBR1, TIE2, TLK1, TLK2, TNK1, TRKA, TRKB, TRKC, TTK, TXK, TYK2, TYRO3, ULK3, WNK3, YANK2, YANK3, YES, YSK1, ZAP70, ZC1/HGK, ZC2/TNIK, and mutants thereof.

Applicants have discovered that compounds of Formula (I) have particular utility in treating proliferative conditions associated with the modulation of kinase activity, and particularly the inhibition of serine/threonine kinase activities. The compounds of the present invention can be used to treat proliferative disorders associated with abnormal kinase activity. As used herein, the terms "treating" and "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

Accordingly, one aspect of the invention is the use of a compound of the Formula (I), or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of Formula (I) or a pharmaceutically acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. Compounds of Formula (I) may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, ZOLADEX®; matrix metalloproteinase inhibitors; VEGF inhibitors, such as anti-VEGF antibodies (AVASTIN®) and small molecules such as ZD6474 and SU6668; Vatalanib, BAY-43-9006, SU11248, CP-547632, and CEP-7055; HER 1 and HER 2 inhibitors including anti-HER2 antibodies (HERCEPTIN®); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g., GLEEVEC® and dasatinib; CASODEX® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and anti-vascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S*,11R*, 12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]heptadecane-5,9-dione, and derivatives thereof; other CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g., 6-thioguanine and 6-mercaptopurine; glutamine antagonists, e.g., DON (AT-125; d-oxo-norleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein may be surgery, radiotherapy or chemotherapy. Such chemotherapy may cover three main categories of therapeutic agent:

(i) antiangiogenic agents that work by different mechanisms from those defined herein before (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyl-transferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as AVASTIN® (bevacizumab) and ERBITUX® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); intercalating antitumor antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide, nitrosoureas, thiotepa; antimitotic agents (for example, vinca alkaloids like vincristine, vinorelbine, vinblastine and vinflunine) and taxoids such as TAXOL® (paclitaxel), Taxotere (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as VELCADE® (bortezomib).

As stated above, the Formula (I) compounds of the invention are of interest for their antiproliferative effects. Such compounds of the invention are expected to be useful in a wide range of disease states including cancer, psoriasis, and rheumatoid arthritis.

More specifically, the compounds of Formula (I) are useful in the treatment of a variety of cancers, including (but not limited to) the following:

carcinoma, including that of the prostate, pancreatic ductal adenocarcinoma, breast, colon, lung, ovary, pancreas, and thyroid;

tumors of the central and peripheral nervous system, including neuroblastoma, glioblastoma, and medulloblastoma; and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neurofibromatosis, pulmonary fibrosis, arthritis, psoriasis, glomerulonephritis, restenosis following angioplasty or vascular surgery, hypertrophic scar formation and inflammatory bowel disease.

The compounds of Formula (I) are especially useful in treatment of tumors having a high incidence of serine/threonine kinase activity, such as prostate, colon, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of Formula (I) may also be useful in the treatment of other cancerous diseases (such as acute myelogenous leukemia) that may be associated with signal transduction pathways operating through kinases such as DYRK1a, CDK, and GSK3β. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS® Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

When a compound according to this invention is administered into a human subject, the daily dosage will normally be determined by the prescribing physician with the dosage generally varying according to the age, weight, sex and response of the individual patient, as well as the severity of the patient's symptoms. Exemplary dosage amounts for a mammal may include from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of protein kinase enzyme levels.

If formulated as a fixed dose, a combination product can, for example, utilize a dosage of the compound of Formula (I) within the dosage range described above and the dosage of another anti-cancer agent/treatment within the approved dosage range for such known anti-cancer agent/treatment. If a combination product is inappropriate, the compounds of Formula (I) and the other anti-cancer agent/treatment can, for example, be administered simultaneously or sequentially. If administered sequentially, the present invention is not limited to any particular sequence of administration. For example, compounds of Formulas (I) can be administered either prior to, or after, administration of the known anti-cancer agent or treatment.

BIOLOGICAL ASSAYS

A. CK2 Kinase Assay

The effectiveness of compounds of the present invention as inhibitors of protein kinases can be readily tested by assays known to those skilled in the art. For example, in vitro protein kinase assays may be conducted with a relevant purified protein kinase and an appropriate synthetic substrate to determine the inhibitory activity of the compounds. Assays for inhibition of CK2 by the instant compounds were performed in 384-well plates with reaction mixtures containing 10 μM of peptide substrate (RRRADDSDDDDD-NH2), [γ-$^{33}$P]ATP (10 μCi) at 25 μM (CK2A1) or 5 μM (CK2A2), 20 mM Hepes (pH 7.4), 100 mM NaCl, 10 mM $MgCl_2$, 0.25 mM dithiothreitol, Brij-35 at 0.015%, and recombinant CK2A1 (10 nM, Invitrogen) or CK2A2 (5 nM, Upstate Biotechnology). Reaction mixtures were incubated at 30° C. for 1 hour, and reaction products were captured by binding to phosphocellulose (P81)

filter plates. Incorporation of radioactive phosphate into the peptide substrate was determined by liquid scintillation counting. The potency of compounds in inhibiting CK2 is expressed as $IC_{50}$, defined as the concentrations of compounds required to inhibit the enzymatic activity by 50%.

The inhibitory activity of the instant compounds may also be measured by recombinant CK2 holoenzyme kinase assays. The assays were performed in U-bottom 384-well plates. The final assay volume was 30 µl prepared from 15 µl additions of enzyme and substrates (fluoresceinated peptide FL-RRRADDSDDDDD-NH2 and ATP) and test compounds in assay buffer (20 mM HEPES pH 7.4, 10 mM $MgCl_2$, 100 mM NaCl, 0.015% Brij35 and 0.25 mM DTT). The reaction was initiated by the combination of bacterially expressed, CK2 α/β or CK2 α'/β holoenzyme with substrates and test compounds. The reaction was incubated at room temperature for 60 minutes and terminated by adding 30 µl of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the CK2 α/β assay was 25 µM ATP, 1.5 µM FL-RRRADDSDDDDD-NH2, 50 µM CK2 α'/β holoenzyme, and 1.6% DMSO. The final concentration of reagents in the CK2 α'/β assay was 10 µM ATP, 1.5 µM FL-RRRADDSDDDDD-NH2, 100 µM CK2 α'/β holoenzyme, and 1.6% DMSO. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

B. Cell Proliferation Inhibition Assay

Compounds were evaluated for their ability to inhibit cell proliferation, using an assay that measures mitochondrial metabolic activity, that is directly correlated with cell numbers. Cells were plated at 2000 cells/well in 96-well plates and were cultured for 24 h in RPMI-1640 supplemented with 2% fetal bovine serum, before test compounds were added. Compounds were diluted in culture medium such that the final concentration of dimethyl sulfoxide never exceeded 1%. Following the addition of compounds, the cells were cultured for an additional 72 h before cell viability was determined by measuring the conversion of 3-(4,5-dimethylthiazol-2-yl)-2,5-diphenyltetrazolium bromide (MTT) dye using the CELLTITER 96® kit (Promega) or by measuring the conversion of [3-(4,5-dimethylthiazol-2-yl)-5-(3-carboxymethoxyphenyl)-2-(4-sulfophenyl)-2H-tetrazolium (MTS) dye using the CELLTITER 96® AQueous (Promega).

The following compounds were found to have the $IC_{50}$ described in Table 1 when measured in the assays described above.

TABLE 1

| Example No. | CK2A1 (CK2α/β) ($IC_{50}$, µM) | CK2A2 (CK2α'/β) ($IC_{50}$, µM) |
|---|---|---|
| 4 | 0.11 | 0.05 |
| 17 | 0.02 | 0.0028 |
| 26 | 4.4 | 0.38 |
| 28 | 0.34 | 0.06 |
| 36 | 0.17 | 0.05 |
| 38 | 0.19 | 0.07 |
| 42 | 0.29 | 0.05 |
| 50 | 0.15 | 0.05 |

TABLE 1-continued

| Example No. | CK2A1 (CK2α/β) ($IC_{50}$, µM) | CK2A2 (CK2α'/β) ($IC_{50}$, µM) |
|---|---|---|
| 51 | 0.17 | 0.06 |
| 94 | 0.06 | 0.05 |
| 111 | 0.02 | 0.0036 |
| 118 | 0.04 | 0.0025 |
| 119 | 0.01 | 0.0027 |
| 125 | 0.01 | 0.0034 |
| 126 | 0.02 | 0.0032 |
| 129 | 0.01 | 0.0036 |
| 138 | 0.03 | 0.0022 |
| 147 | 0.01 | 0.0039 |
| 152 | 0.02 | 0.0037 |
| 172 | 0.15 | 0.05 |
| 184 | 0.44 | 0.05 |
| 187 | 2.2 | 0.56 |
| 188 | 1.7 | 0.56 |
| 189 | 12 | 0.67 |
| 190 | 2.8 | 0.75 |
| 191 | 5.9 | 0.81 |
| 196 | 2.3 | 0.79 |
| 197 | 4.3 | 1.0 |
| 199 | 5.8 | 0.7 |
| 200 | 2.1 | 0.33 |

METHODS OF PREPARATION

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art. These schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). All documents cited herein are incorporated herein by reference in their entirety.

Unless otherwise specified, the various substituents of the compounds are defined in the same manner as the Formula (I) compound of the invention. Compounds of Formula (I) may be prepared according to the following schemes utilizing chemical transformations familiar to anyone of ordinary proficiency in the art of organic/medicinal chemistry. References to many of these transformations can be found in Smith, M. B. et al., *March's Advanced Organic Chemistry Reactions, Mechanisms, and Structure*, Fifth Edition, Wiley Interscience, New York (2001), or other standard texts on the topic of synthetic organic chemistry.

For ease of reference, the following abbreviations are used herein:
BOC=tert-butoxycarbonyl
BOP=(Benzotriazol-1-yloxy)tris(dimethylamino)phosphonium hexafluorophosphate
bp=boiling point
Bu=butyl
Cbz=carbonylbenzyloxy
DMAP=4-dimethylaminopyridine
DIPEA or DIEA=N,N-diisopropylethylamine
DME=1,2-dimethoxyethane
DMF=N,N-dimethyl formamide
DppF=1,1'-bis(diphenylphosphino)ferrocene
EDCI=1-(3-dimethylaminopropyl)-3-ethylcarbodiimide
Et=ethyl
$Et_2O$=diethyl ether HOBT=1-hydroxybenzotriazole
EtOAc=ethyl acetate
HOAc=acetic acid
EtOH=ethanol
g=gram(s)
H=hydrogen
l=liter
mCPBA—meta chloro perbenzoic acid
Me=methyl
MeCN=acetonitrile
MeOH=methanol
nM=nanomole or nanomolar
NMP=1-methyl-2-pyrrolidinone
NBS=N-bromosuccinimide
$Pd_2dba_3$=tris(dibenzylideneacetone)dipalladium (0)
Ph=phenyl
Pr=propyl
PS=polystyrene
TEA=triethylamine
TFA=trifluoroacetic acid
THF=tetrahydrofuran
mg=milligram(s)
ml or mL=milliliter
μl=microliter
mmol=mM=millimole or millimolar
μmol=μM=micromole or millimolar
mol=mole
mp=melting point
RT or rt=room temperature
HPLC=high pressure liquid chromatography
LC/MS=liquid chromatography/mass spectrometry
Tr=retion time (in minutes)

Compound (i) (Scheme 1, R=alkyl, e.g., an Ethyl group), prepared as described in U.S. Pat. No. 7,514,435 can be converted by the action of a halogenating agent, preferably bromine or N-bromosuccinimide and catalytic TFA, in a solvent such as dichloromethane, to the halogenopyrrolotriazines (ii) ($X_1$=halogen). Treatment with an aqueous base such as an alkali metal hydroxide furnishes carboxylic acid (iii) which can be converted to halogenopyrrolotriazine acid halides (iv) by the action of an agent such as thionyl chloride, generally with heating and addition of a catalytic amount of DMF ($X_2$=halogen). Other methods for the conversion of (ii) to (iii) could include hydrolysis with a strong acid or nucleophillic dealkylation. Treatment of (iv) with a secondary amine such as N,O-dimethylhydroxylamine, conveniently generated in situ from the HCl, or related salt with a base such as triethylamine, followed by ammonia or a primary amine, provides aminopyrrolotriazine carboxamides (v). Amides such as these are electrophillic, undergoing exchange to provide amides or hydrazides (vi) when heated with amines or hydrazines $R_1NHR_2$ either neat or in a solvent. Conversion to compounds of Formula (I) is accomplished from (vi) by cross-coupling with an appropriate boronic acid, organozinc, organostannane or the like, preferably using the conditions of Suzuki. See: Kotha, S. et al., *Tetrahedron*, 58:9633-9695 (2002).

Scheme 2 describes further methodology for the preparation of compounds of Formula (I).

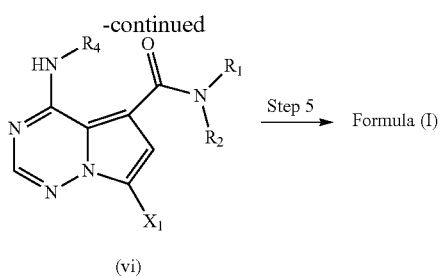

Triazinone esters (ii) (preparation shown in Scheme 1) can be converted to a halogenopyrrolotriazines (vii) by the action of an agent such as thionyl chloride, generally with heating (Y=halogen). Nucleophillic aromatic substitution occurs upon treatment with ammonia or a primary amine, providing pyrrolotriazine amino ester (viii). Transformation to the carboxylic acids (ix) is accomplished as in Scheme 1. These carboxylic acids can be converted to amides or hydrazides (vi) using amines or hydrazines $R_1NHR_2$, a coupling reagent such as BOP and a tertiary amine base in a solvent such as DMF. The use of such peptide coupling reagents has been reviewed by Han, S-Y et al., *Tetrahedron*, 60:2447-2467 (2004). Conversion to compounds of Formula (I) is accomplished as in Scheme 1.

Scheme 3 describes further methodology for the preparation of compounds of Formula (I).

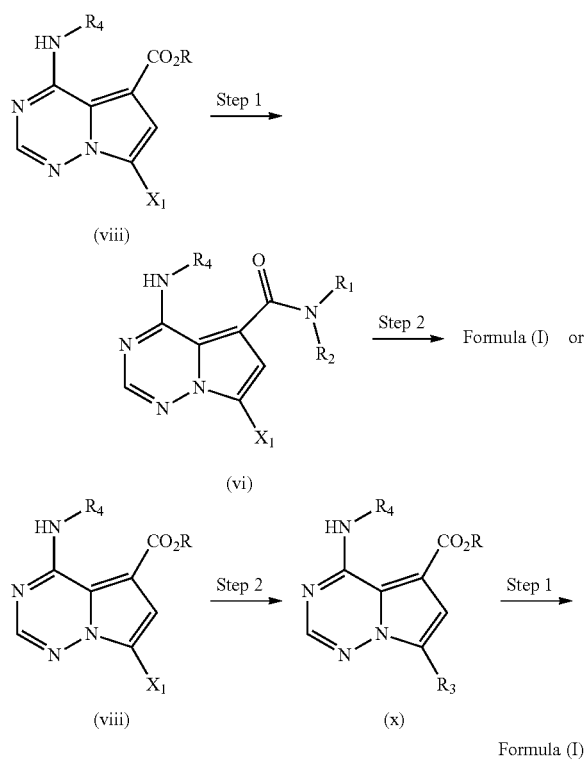

As shown in Scheme 3, triazinone esters (viii) (preparation shown in Scheme 2) or homologous esters can be converted to amides (vi) by heating with amines $R_1NHR_2$ either neat or in a solvent. Conversion to compounds of Formula (I) is accomplished as in Scheme 1. Alternatively, the order of these two steps could be reversed, with intermediate (viii) undergoing a Suzuki or related coupling to provide intermediate (x) which undergoes aminolysis with an amine of the form $R_1NHR_2$ to provide compounds of the invention.

Scheme 4 describes further methodology for the preparation of compounds of Formula I.

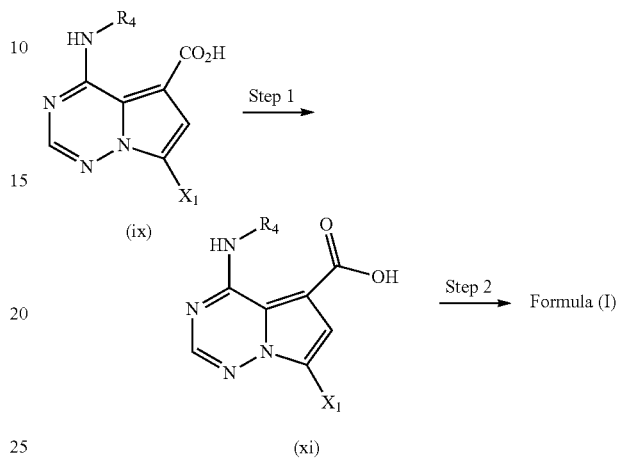

Halotriazinone acid (ix) (preparation shown in Scheme 2) can be converted to the cross-coupled product (xi) using the conditions described for conversion of (vi) to Formula (I) in Scheme 1. Conversion of (xi) to compounds of Formula (I) is accomplished using the peptide coupling conditions described for the conversion of (ix) to (vi) in Scheme 2.

Compounds of Formula (I) or suitably-protected derivatives thereof (For the use of protecting groups in organic synthesis see: Greene, T. W. et al., eds., *Protective Groups in Organic Synthesis*, Third Edition, Wiley-Interscience, New York (1999)) can be deprotected to afford further compounds of Formula (I). Additionally, these deprotected compounds may undergo further elaboration by methods familiar to those proficient in the art of organic/medicinal chemistry. Such transformations may include, but are not limited to, reaction with chloroformates, isocyanates, sulfonyl halides, acid halides or activated esters, alkyl halides/mesylates/tosylates and the like, reductive aminations, and Mitsunobu (see Hughes, D. L., *Organic Preparations and Procedures International*, 28:127-164 (1996)) reactions. Some of these transformations are illustrated in the following schemes.

Scheme 5 shows the elaboration of carboxylic acid intermediates such as (xi) by coupling with mono-protected difunctional compounds such as diamines then deprotection to afford species such as (xiii). The range of connectivity (illustrated by a circle) between the functional groups is further defined below and in the claims. The scope of the reaction should allow incorporation of symmetrical or unsymmetrical and linear or cyclic diamines. Additionally, diamines with substituents, stereogenic centers, or incorporated heteroatoms on the ring or chain could be introduced by this methodology. Alternatively, the coupling could be performed to afford (xiii) directly using an aminoalcohol or excess of an unprotected diamine. Reaction of nucleophillic species such as (xiii) with electrophiles affords additional compounds of the invention. For example, an amine (xiii) could undergo amide bond formation to provide compounds of the invention under conditions described above. The scope of the reaction could, however, include additional reactions of amines, alcohols, or other nucleophiles with electrophiles as discussed above, all of which are familiar to those proficient in the art of organic/medicinal chemistry.

Scheme 5

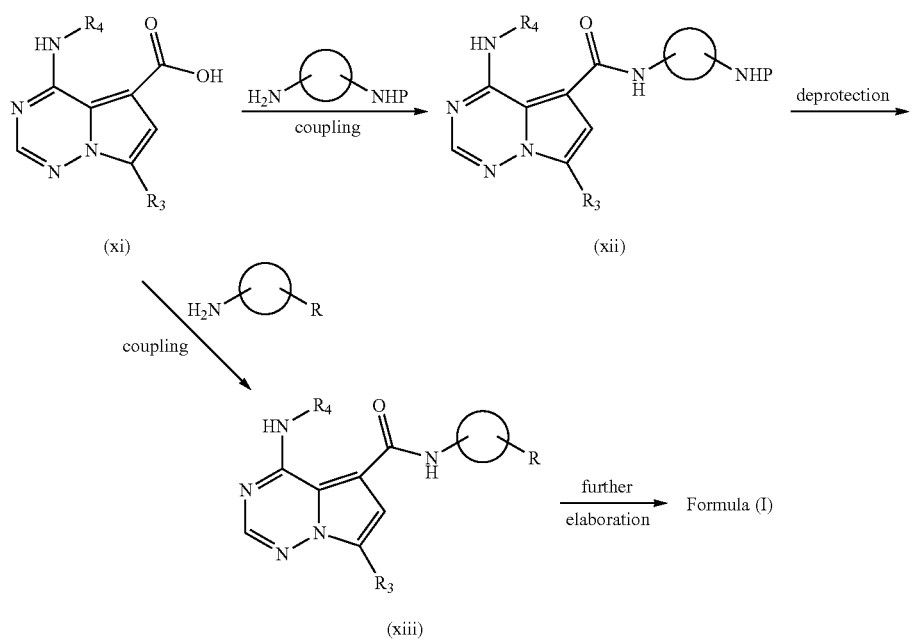

P = protecting group
R = NH₂ or OH

Carboxylic acid intermediates such as (xi) can be coupled with amines bearing functional groups which can be further derivatized such as carboxylic acids, aldehydes, ketones and the like or protected versions thereof. An example of this is provided in Scheme 6, wherein (xv) are prepared and saponified to provide carboxylic acids such as (xvi). As in Scheme 5, the range of connectivity (illustrated by a circle) between the functional groups is further defined below and exemplified in the specification. The scope of the reaction should allow incorporation of symmetrical or unsymmetrical and linear or cyclic amines. Additionally, amines with substituents, stereogenic centers, or incorporated heteroatoms on the ring or chain could be introduced by this methodology. Coupling with electrophiles such as amines affords additional compounds of the invention. Further, such esters and acids may be converted to alcohols, ketones, or aldehydes which may be compounds of the invention or which may serve as intermediates for conversion into compounds of the invention using transformations familiar to those skilled in the art of organic/medicinal chemistry. Such transformations could include, but are not limited to, alkylations, Wittig reactions, and addition of organometallic reagents or other carbon or heteroatom-based nucleophiles.

Scheme 6

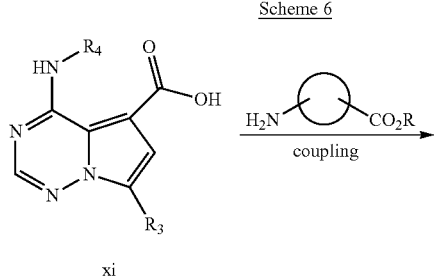

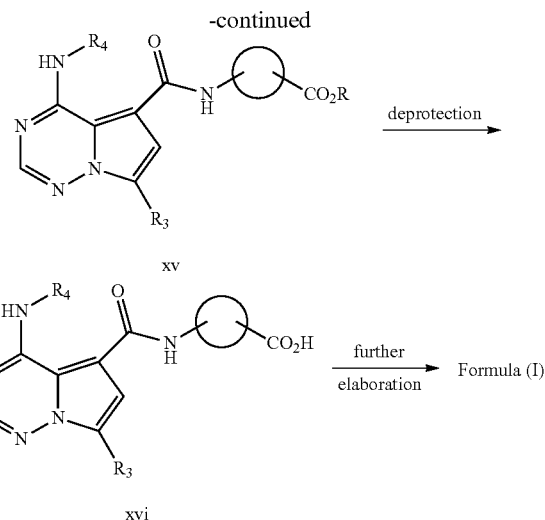

Further compounds of the invention may be prepared by the procedures outlined in Scheme 7. Incorporation of a protected amine onto the triazine core (Step 1) furnishes protected aminopyrrolotriazines xvii (R″=protecting group). It is often necessary to incorporate functional groups such as alcohols, amines, and acyl groups and the like in protected form in order to facilitate further manipulations. Conditions for incorporation of protecting groups as well as their selective removal are known to those of ordinary skill in the art of organic chemistry. Conversion of xvii (preferably X=Br or I) into carboxylic acid, ester, or related acyl intermediates xviii (Step 2) may be accomplished through metal-halogen exchange followed by quenching with an electrophile such as $CO_2$, DMF or a related carboxamide, or a chloroformate or related acyl. An alternative method for this transformation is the palladium (or related metal)-catalyzed carbonylation. Carboxylic acids xviii are useful intermediates for elaboration into compounds of the invention or advanced intermediates xix through reactions such as the coupling with a hydrazine or related protected or alkylated/acylated fragment. (Step 3) Transformation of esters xix into carboxamides xx (Step 4) is accomplished as described in the preceeding schemes, for instance by direct nucleophilic addition of amine $R_1R_2NH$ to the ester or by saponification followed by an amide coupling reaction. In Step 5 any protecting groups are removed, and the hydrazide or related group is cyclized to furnish compounds of the invention. Such cyclizations could proceed by treatment of a free hydrazide with CDI, phosgene, or a related acyl equivalent or via heating or treatment of an acylated or similarly-derivatized hydrazide with acid or base. Additional compounds of the invention may be prepared by performing further transformations on the heteroaromatic $R_3$ group. It is further understood by those skilled in the art of organic synthesis that some cases the sequence of the above steps may be altered or various transformations may be telescoped (combined into a one-pot process).

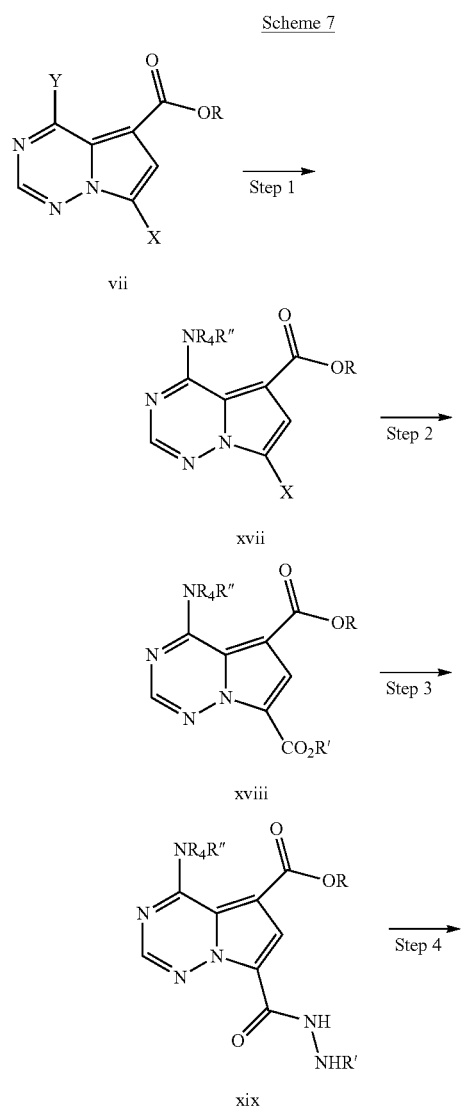

Scheme 7

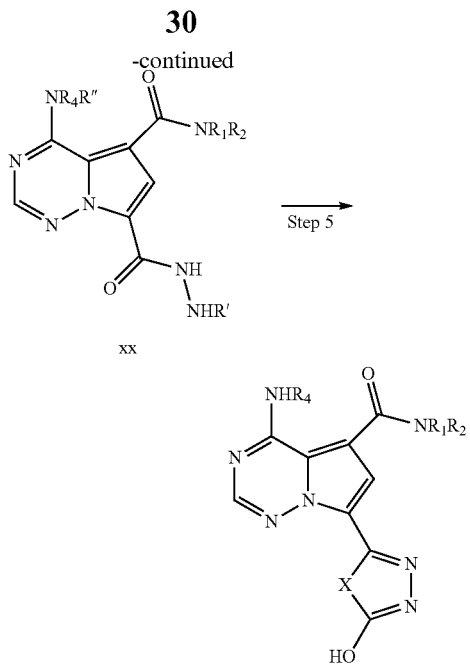

Formula (I)

EXAMPLES

The invention is now described with reference to the following examples. These examples are provided for the purpose of illustration only and the invention should in no way be construed as being limited to these examples but rather should be construed to encompass any and all variations which become evident as a result of the teaching provided herein.

Analytical Methods

Air- or moisture-sensitive reactions were performed under an atmosphere of nitrogen in anhydrous solvents (EMD DRI-SOLV®) and were monitored for completeness by thin layer chromatography (TLC) or tandem liquid chromatography-mass spectroscopy (LCMS). For TLC, 0.25 mm plates coated with Silica60/F254 were used with visualization by UV light at 254 nM, exposure to iodine vapor, or heating with PMA (phosphomolybdic acid solution), ninhydrin in ethanol, anisaldehyde solution, or eerie ammonium molybdate solution. Unless otherwise specified, "dried" refers to the addition of anhydrous $MgSO_4$ followed by filtration and rinsing the residual solids with an appropriate organic solvent. "Stripped" means concentration under reduced pressure, generally on a rotary evaporator. "Silica gel chromatography" or "chromatographed on silica gel" refers to glass column chromatography performed in a manner similar to that described by Still (J. Org. Chem., 43:2923 (1978)). Typically silica gel 60 (EMD, 230-400 mesh ASTM) is used with solvents from JT Baker or Mallinckrodt. For all chromatographic purifications the isolation of product by concentration of the appropriate fractions by evaporation at or below ambient pressure is implied. Melting points were determined on a Thomas-Hoover uni-melt apparatus and are uncorrected. Generally, mass spectral results are reported as the $(M+H)^+$ value. For halogenated compounds where two or more peaks are significant, m/z for one peak in the cluster, generally the most intense, is reported. $^1H$ NMR spectra were recorded on dilute solutions at 400 or 500 MHz on Varian or Jeol instruments in the solvents indicated. Chemical shifts are reported in parts per million (ppm) downfield from internal tetramethylsilane (TMS) or from the position of TMS inferred by the deuterated NMR solvent. Multiplicities are reported as: singlet-s, doublet-d, triplet-t, quartet-q, or multiplet-m. Peaks which exhibit broadening are further denoted as br. Integrations are approximate. It should be noted that integration intensities, peak shapes, chemical shifts and coupling constants can be dependent on solvent, concentration, temperature, pH, and other factors.

Example 1

4-Amino-N-(4-hydroxybutyl)-7-(4-pyridinyl)pyrrolo[2,1-f][1,2,4]triazine-5-carboxamide

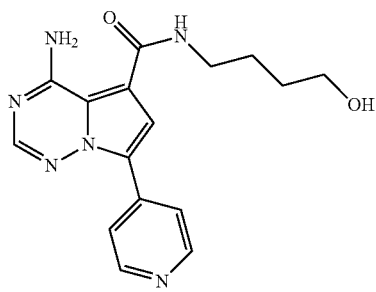

1A: Ethyl 4-hydroxypyrrolo[1,2-f][1,2,4]triazine-5-carboxylate

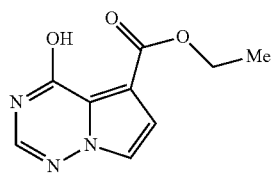

1A was synthesized according to the procedure described in U.S. Pat. No. 7,514,435.

1B: Ethyl 7-bromo-4-hydroxypyrrolo[1,2-f][1,2,4]triazine-5-carboxylate

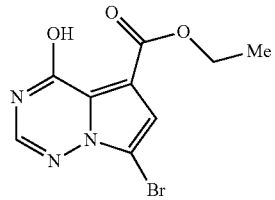

1A (2.072 g, 10 mmol) was suspended in dichloromethane (15 mL) and treated with TFA (0.3 mL). To this suspension was added NBS (1.87 g, 10.5 mmol) and the reaction mixture was stirred for 2 h at ambient temperature. The mixture was then concentrated under reduced pressure and the crude product was suspended in THF-hexanes. The reaction mixture was filtered, rinsed several times with water and once with ether, and air-dried briefly to afford a solid. Brief evacuation (high-vac. line) served to remove traces of solvent, providing 1B (2.62 g, 92% yield) as a colorless solid. MS (ES): m/z=288 [M+H]$^+$. $^1$H NMR (400 MHz, DMSO-$d_6$) δ ppm 1.28 (t, 3H, J=7.2 Hz); 4.00-4.48 (m, 2H); 7.09 (s, 1H) 8.08 (s, 1H); 12.14 (s, 1H).

1C: 7-bromo-4-hydroxypyrrolo[1,2-f][1,2,4]triazine-5-carboxylic acid

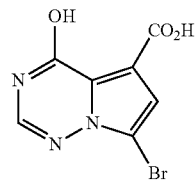

1B (2.55 g, 8.91 mmol) was suspended in THF (20 mL) and MeOH (5 mL) and treated with LiOH (0.599 g, 25 mmol) in water (20 mL). The mixture was warmed to reflux for 1 h. Most of the material was dissolved, leaving a faintly cloudy solution. The reaction was diluted with water (20 mL), filtered hot, and treated with glacial acetic acid (3 mL) with vigorous stirring. This resulted in the rapid formation of a colorless precipitate which was filtered, rinsed with water, and air-dried to provide 1C (1.86 g, 81% yield). MS (ES): m/z=258 [M+H]$^+$. $^1$H NMR (400 MHz, DMSO-$d_6$) δ ppm 7.26 (s, 1H); 8.30 (s, 1H); 13.1 (br. s, 1H); 13.9 (br. s, 1H).

1D: 7-Bromo-4-chloropyrrolo[1,2-f][1,2,4]triazine-5-carbonyl chloride

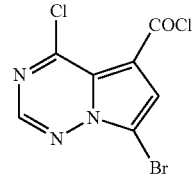

1C (6.9 g, 26.7 mmol) was suspended in thionyl chloride (50 mL) and heated to reflux. After 5 h, the reaction became homogeneous-a pale yellow solution. Thionyl chloride was removed under reduced pressure, and the residue was placed under high vacuum to provide 1D as a pale yellow solid. This material was generally used without characterization in the subsequent steps but could be stored if kept cold.

1E: 7-Bromo-4-chloro-N-methoxy-N-methylpyrrolo[1,2-f][1,2,4]triazine-5-carboxamide

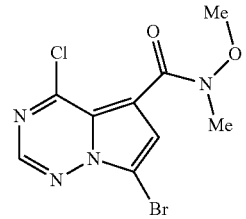

To a stirred solution of 1D (2.5 g, 8.48 mmol) in CH$_2$Cl$_2$ was added triethylamine (2.95 mL, 21.19 mmol) followed by N,O-dimethylhydroxylamine hydrochloride (0.786 g, 8.05 mmol). The mixture was stirred for 1 h at room temperature then diluted with water and extracted with EtOAc (2×). The combined organics were washed with brine, dried over anhydrous magnesium sulfate and concentrated under reduced pressure to provide 1E (2.26 g, 7.07 mmol, 83% yield). MS (ES): m/z=319 [M+H]$^+$. $^1$H NMR (400 MHz, DMSO-d$_6$) δ ppm 3.2 (s, 3H); 3.38 (s, 3H); 7.53 (s, 1H); 8.66 (s, 1H).

1F: 4-Amino-7-bromo-N-methoxy-N-methylpyrrolo[1,2-f][1,2,4]triazine-5-carboxamide

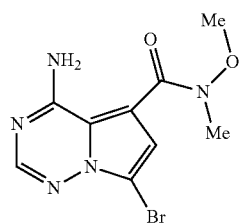

1F

To a stirred solution of 1E (1.24 g, 3.88 mmol) in dioxane (10 mL) was added conc. NH$_4$OH (10 mL). The mixture was stirred for 1 h at room temperature, concentrated to remove most of the dioxane, and diluted with water. The resulting white solid was collected by filtration and dried under high vacuum to provide 1F (1.04 g, 89% yield). $^1$H NMR (400 MHz, DMSO-d$_6$) δ ppm 3.34 (s, 3H); 3.68 (s, 3H); 7.37 (s, 1H); 8.08 (s, 1H); 8.32 (br. s, 1H); 9.34 (br. s, 1H).

1G: 4-Amino-7-bromo-N-(4-hydroxybutyl)pyrrolo[1,2-f][1,2,4]triazine-5-carboxamide

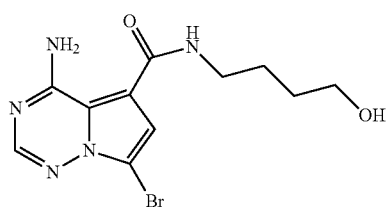

1G 1F (0.07 g, 0.233 mmol) and 4-aminobutan-1-ol (0.5 g, 5.61 mmol) were combined and heated to 110° C. with stirring for 1.5 h. The reaction was cooled and stirred overnight. The reaction mixture was poured into dilute aq. HOAc and extracted with chloroform (3×). The combined organics were washed with brine, dried, and concentrated under reduced pressure to provide 1G (0.044 g, 58% yield) as an off-white powder. MS (ES): m/z=329.9 [M+H]$^+$. $^1$H NMR (400 MHz, DMSO-d$_6$) δ ppm 1.40-1.61 (m, 4H); 3.26-3.31 (m, 2H); 3.40-3.46 (m, 2H); 4.14 (t, 1H, J=5.1 Hz); 7.51 (s, 1H); 8.02 (s, 1H); 8.30 (br. s, 1H); 8.62 (br. t, 1H, J=5.5 Hz); 10.37 (br. s, 1H).

1: 4-Amino-N-(4-hydroxybutyl)-7-(4-pyridinyl)pyrrolo[2,1-f][1,2,4]triazine-5-carboxamide

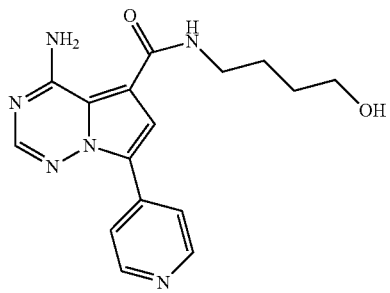

1

To a stirred suspension of 1G (0.036 g, 0.110 mmol), tetrakis(triphenylphosphine)palladium(0) (0.127 g, 0.110 mmol) and pyridin-4-ylboronic acid (0.013 g, 0.110 mmol) in DMF (2 mL) was added 2M K$_2$CO$_3$ (0.25 mL). The mixture was degassed, placed under nitrogen, and stirred at 100° C. for 2.5 h. The mixture was cooled, poured into water and extracted with 9:1 chloroform-ethanol (3×). The combined organics were washed with brine, dried, and concentrated under reduced pressure. The crude product was purified by preparative HPLC (C18 HPLC, Axia 30×100 mm column, MeOH-water-TFA gradient). Concentration of the appropriate fractions provided 1.HCl (0.019 g, 48% yield) as an off-white powder. HPLC: 8.12 min (Waters Sunfire C18 4.6×150 mm 3.5 micron. 1 mL/min, 10-90% methanol-water 0.2% H$_3$PO$_4$, gradient over 10 min.). MS (ES): m/z=327.0 [M+H]$^+$. $^1$H NMR (400 MHz, DMSO-d$_6$) δ ppm 1.46-1.67 (m, 4H); 3.31-3.37 (m, 2H); 3.42-3.47 (m, 2H); 8.26 (s, 1H); 8.53 (s, 1H); 8.66-8.74 (m, 3H); 8.94-9.00 (m, 3H); 10.71 (br. s, 1H).

Example 2

4-Amino-N-(3-hydroxypropyl)-7-(4-pyridinyl)pyrrolo[2,1-f][1,2,4]triazine-5-carboxamide

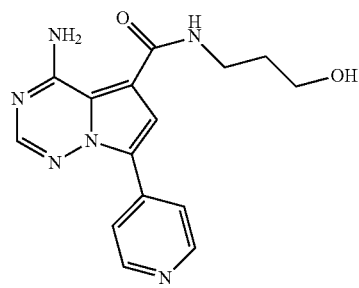

2

2A: Ethyl 7-bromo-4-chloropyrrolo[1,2-f][1,2,4]triazine-5-carboxylate

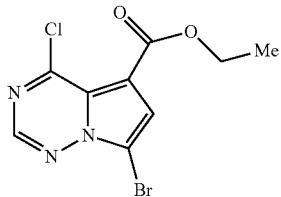

2A was prepared from 1B (1.58 g, 5.52 mmol) by the general methods shown for 1D. 2B was obtained as a pale yellow solid which was used as is in the next reaction or could be stored at −40° C.

2B: Ethyl 4-amino-7-bromopyrrolo[1,2-f][1,2,4]triazine-5-carboxylate

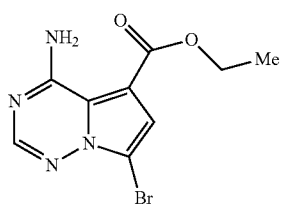

2B was prepared from 2A (1.58 g, 5.52 mmol) by the general methods shown for 1F. 2B (1.51 g, 96% yield) was obtained as white solid. MS (ES): m/z=286.9 [M+H]$^+$. $^1$H NMR (400 MHz, DMSO-d$_6$) δ ppm 1.41 (t, 3H, J=7.2 Hz); 4.40 (q, 2H, J=7.2 Hz); 7.38 (s, 1H); 8.21 (s, 1H); 8.63 (br. s, 1H); 9.15 (br. s, 1H).

2C: 4-Amino-7-bromopyrrolo[1,2-f][1,2,4]triazine-5-carboxylic acid

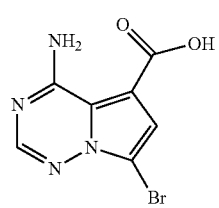

2C was prepared from 2B (0.29 g, 1.02 mmol) by the general methods shown for 1C. 2C (0.23 g, 88% yield) was obtained as off white powder. MS (ES): m/z=259.0 [M+H]$^+$. $^1$H NMR (400 MHz, DMSO-d$_6$) δ ppm 13.4 (br. s, 1H); 9.41 (br. s, 1H); 8.47 (br. s, 1H); 8.10 (s, 1H); 7.26 (s, 1H).

2D: 4-Amino-7-bromo-N-(3-hydroxypropyl)pyrrolo[1,2-f][1,2,4]triazine-5-carboxamide

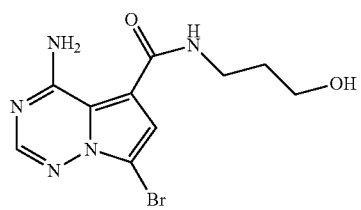

To a stirred solution of 3-aminopropan-1-ol (0.117 g, 1.556 mmol) and 2C (0.1 g, 0.389 mmol) in DMF (1 mL) was added triethylamine (0.163 mL, 1.167 mmol) followed by BOP (0.206 g, 0.467 mmol). The solution was stirred for 20 min. The crude was purified on preparative HPLC (C18 RP HPLC (Luna 100×30 mm column, MeOH-water-TFA gradient). Concentration of appropriate fractions provided 2D (0.091 g, 75% yield) as white solid. $^1$H NMR (400 MHz, DMSO-d$_6$) δ ppm 10.55 (br. s, 1H); 8.65 (br. t, 1H, J=5.6 Hz); 8.46 (br. s, 1H); 8.06 (s, 11H); 7.53 (s, 1H); 3.47 (t, 2H, J=6.3 Hz); 3.31-3.37 (m, 2H); 1.66-1.74 (m, 2H).

2: 4-Amino-N-(3-hydroxypropyl)-7-(4-pyridinyl)pyrrolo[2,1-f][1,2,4]triazine-5-carboxamide

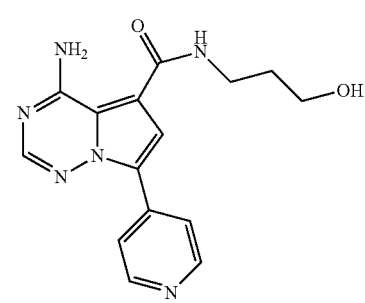

2 was prepared from 2D (0.07 g, 0.223 mmol) and pyridine-4-boronic acid by the general methods shown for 1. 2.TFA (0.029 g, 31% yield) was obtained as a pale yellow powder. HPLC: 7.27 min. (Waters Sunfire C18 4.6×150 mm 3.5 micron. 1 mL/min, 10-90% methanol-water 0.2% H$_3$PO$_4$, gradient over 10 min.). MS (ES): m/z=312.9 [M+H]$^+$. $^1$H NMR (400 MHz, DMSO-d$_6$) δ ppm 10.57 (br. s, 1H); 8.91 (d, 211, J=6.5 Hz); 8.78 (br. t, 1H, J=5.3 Hz); 8.58 (br. s, 1H);

8.56 (d, 2H, J=6.5 Hz); 8.29 (s, 1H); 8.22 (s, 1H); 3.51 (t, 2H, J=6.3 Hz); 3.35-3.42 (m, 2H); 1.69-1.77 (m, 2H).

Example 3

4-Amino-N-(trans-4-hydroxycyclohexyl)-7-(2-fluoro-4-pyridinyl)pyrrolo[2,1-f][1,2,4]triazine-5-carboxamide

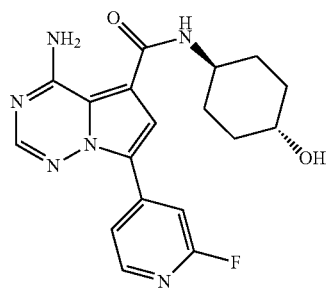

3

3A: 4-Amino-N-(trans-4-hydroxycyclohexyl)-7-bromopyrrolo[2,1-f][1,2,4]triazine-5-carboxamide

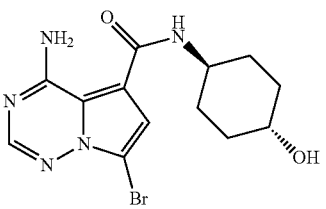

3A 3A was prepared from 2C (100 mg, 0.39 mmol) and (trans)-4-aminocyclohexanol (67 mg, 0.58 mmol) by the general methods shown for 2D. 3A (135 mg, 98% yield) was obtained as a white solid. HPLC: 3.83 min (YMC S5 ODS, 4.5×50 mm. 4 mL/min, 10-90% methanol-water 0.2% $H_3PO_4$, gradient over 12 min). MS (ES): m/z=354 [M+H]$^+$.

3: 4-Amino-N-(trans-4-hydroxycyclohexyl)-7-(2-fluoro-4-pyridinyl)pyrrolo[2,1-f][1,2,4]triazine-5-carboxamide

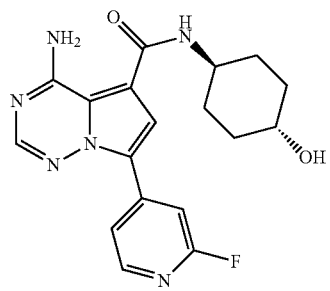

3

A suspension of 3A (39 mg, 0.11 mmol), 2-fluoropyridin-4-ylboronic acid (31 mg, 0.22 mmol) and aq. potassium carbonate (0.14 mL, 0.21 mmol) in 2 mL of degassed DMF was treated with 6 mg (0.006 mmol) of tetrakis(triphenylphosphine)palladium(0). The mixture was stirred at 100° C. for 2 h, cooled to RT, and diluted with water. The resulting mixture was extracted three times with 9:1 chloroform-ethanol, and the combined organic extracts dried and concentrated. Trituration from ether afforded 3 (8 mg, 18% yield) as a white powder. HPLC: 5.88 min (YMC S5 ODS, 4.5×50 mm. 4 mL/min, 10-90% methanol-water 0.2% $H_3PO_4$, gradient over 12 min). MS (ES): m/z=371 [M+H]$^+$. $^1$H NMR (400 MHz, DMSO-$d_6$) δ ppm 10.49 (br. s, 1H); 8.36-8.44 (m, 3H); 8.16 (s, 1H); 8.15 (s, 1H); 8.01-8.04 (m, 1H); 7.95 (s, 1H); 4.65 (d, 1H, J=4.3 Hz); 3.75-3.86 (m, 1H); 3.40-3.51 (m, 1H); 1.85-1.96 (m, 4H); 1.23-1.49 (m, 4H).

Example 4

4-Amino-N-(trans-4-hydroxycyclohexyl)-7-(2-ethoxy-4-pyridinyl)pyrrolo[2,1-f][1,2,4]triazine-5-carboxamide

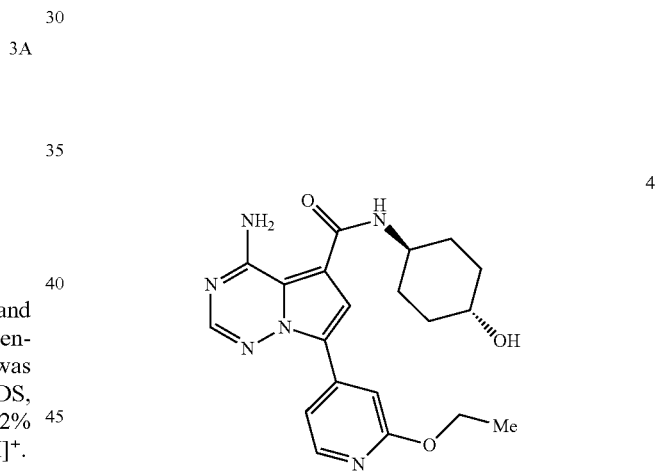

4

A solution of 0.24 M sodium ethoxide (1.0 mL) was treated with 3 (15 mg, 0.04 mmol), and the resulting suspension was stirred at 70° C. for 1.5 h. The reaction was cooled to RT, diluted with 1 mL of water, and the resulting solid was collected by filtration. This crude product was purified by prep. HPLC (gradient elution with MeOH-water-TFA) to afford, after neutralization and collection by filtration, 4 (6.0 mg, 37% yield) as a white solid. HPLC: 12.02 min (YMC S5 ODS, 4.5×50 mm. 1 mL/min, 10-90% methanol-water 0.2% $H_3PO_4$, gradient over 15 min). MS (ES): m/z=397 [M+H]$^+$. $^1$H NMR (400 MHz, DMSO-$d_6$) δ ppm 10.42 (br. s, 1H); 8.26-8.30 (m, 2H); 8.22 (d, 1H, J=5.5 Hz); 8.07 (s, 1H); 8.01 (s, 1H); 7.59 (s, 1H); 7.56 (d, 1H, J=5.5 Hz); 4.59 (d, 1H, J=4.4 Hz); 4.33 (q, 2H, J=7.2 Hz); 3.71-3.80 (m, 1H); 3.35-3.45 (m, 1H); 1.81-1.90 (m, 4H); 1.20-1.45 (m, 7H).

Example 5

4-Amino-N-(2-(1H-imidazol-4-yl)ethyl)-7-(4-pyridinyl)pyrrolo[2,1-f][1,2,4]triazine-5-carboxamide

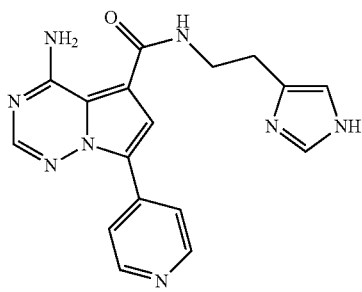

5A: Ethyl 4-amino-7-(pyridin-4-yl)pyrrolo[1,2-f][1,2,4]triazine-5-carboxylate

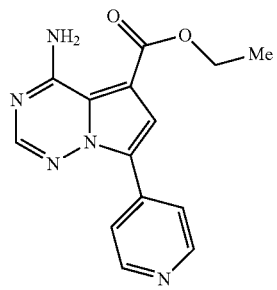

5A was prepared from 2B (0.1 g, 0.351 mmol) and pyridine-4-boronic acid by the general methods shown for 3. 5A (0.026 g, 26% yield) was obtained as an off-white powder. MS (ES): m/z=284.0 [M+H]+. $^1$H NMR (400 MHz, DMSO-$d_6$) δ ppm 9.04 (br. s, 1H); 8.46 (d, 2H, J=6.3 Hz); 8.37 (br. s, 1H); 7.99 (s, 1H); 7.94 (d, 2H, J=6.3 Hz); 7.58 (s, 1H); 4.20 (q, 2H, J=7.1 Hz); 1.19 (t, 3H, J=7.2 Hz).

5: 4-Amino-N-(2-(1H-imidazol-4-yl)ethyl)-7-(4-pyridinyl)pyrrolo[2,1-f][1,2,4]triazine-5-carboxamide

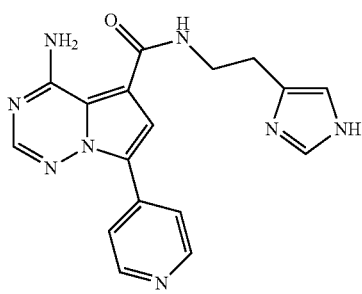

5A (13 mg, 0.046 mmol) and 2-(1H-imidazol-4-yl)ethanamine (200 mg, 1.799 mmol) were placed under nitrogen in a 1 dram vial and heated at 100° C. for 2.5 h. The reaction was cooled and treated with water (4 mL). After stirring for a few minutes at ambient temperature, a precipitate formed. The solid was filtered, rinsed with water, and air-dried to provide 5 (0.015 g, 94% yield) as an off-white papery solid. HPLC: 1.65 min. (YMC S5 ODS, 4.6×50 mm. 4 mL/min, 10-90% methanol-water 0.2% $H_3PO_4$, gradient over 12 min). MS (ES): m/z=349.0 [M+H]+. $^1$H NMR (400 MHz, DMSO-$d_6$) δ ppm (major conformational family): 11.8 (br. s, 1H); 10.44 (br. s, 1H); 8.78-8.82 (m, 1H); 8.69 (d, 2H, J=6.3 Hz); 8.33 (br. s, 1H); 8.09 (s, 1H); 8.04 (d, 2H, J=6.0 Hz); 7.95 (s, 1H); 7.57 (s, 1H); 6.93 (s, 1H); 3.51-3.58 (m, 2H); 2.75-2.81 (m, 2H).

Example 6 tert-Butyl (4-(((4-amino-7-(2-methoxy-4-pyridinyl)pyrrolo[2,1-f][1,2,4]triazin-5-yl)carbonyl)amino)cyclohexyl)carbamate

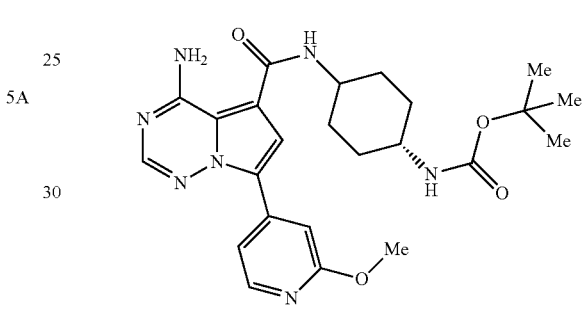

6A: 4-Amino-7-(2-methoxypyridin-4-yl)pyrrolo[1,2-f][1,2,4]triazine-5-carboxylic acid

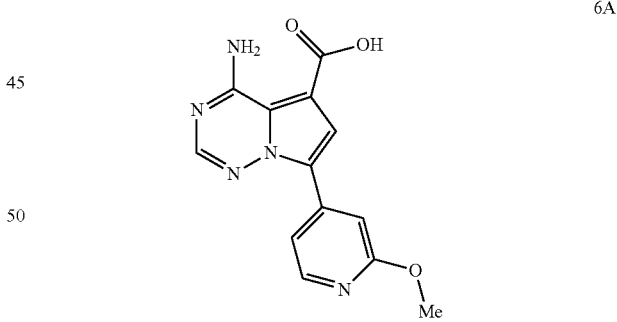

A suspension of 2C (400 mg, 1.56 mmol), 2-methoxypyridin-4-ylboronic acid (428 mg, 2.80 mmol) and aq. potassium carbonate (2.33 mL, 4.67 mmol) in DMF (10 mL) was degassed then treated with tetrakis(triphenylphosphine)palladium (0) (90 mg, 0.078 mmol). The mixture was heated at 100° C. for 1 h then cooled and diluted with water. The solution was brought to ~pH6 with glacial HOAc, and the resulting precipitate was filtered, rinsed with ether, and air-dried. The mother liquor was partially concentrated, and a second crop was collected, rinsed with ether and air-dried. Combination of the two crops afforded 6A (324 mg, 73% yield) as a cream-colored solid. MS (ES): m/z=286.3

[M+H]+. 1H NMR (400 MHz, DMSO-d6) δ ppm 13.43 (br. s, 1H); 9.65 (br. s, 1H); 8.46 (br. s, 11H); 8.22 (d, 1H, J=5.27 Hz); 8.15 (s, 1H); 7.73 (s, 1H); 7.65-7.71 (m, 2H); 3.90 (s, 3H).

6: tert-Butyl (trans)-(4-(((4-amino-7-(2-methoxy-4-pyridinyl)pyrrolo[2,1-f][1,2,4]triazin-5-yl)carbonyl)amino)cyclohexyl)carbamate

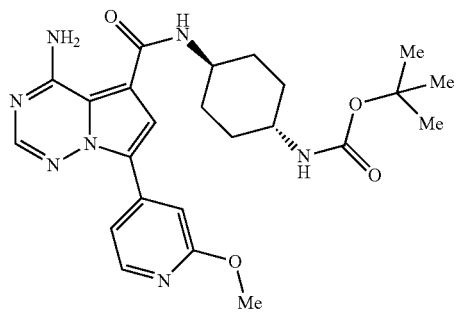

6

6 was prepared from 6A (275 mg, 0.964 mmol) and (trans)-tert-butyl 4-aminocyclohexylcarbamate (310 mg, 1.45 mmol) by the general methods shown for 2D. 6 (388 mg, 84% yield) was obtained as a white solid. HPLC: 14.97 min (YMC S5 ODS, 4.5×50 mm. 1 mL/min, 10-90% methanol-water 0.2% H3PO4, gradient over 15 min). MS (ES): m/z=482.6 [M+H]+. 1H NMR (400 MHz, DMSO-d6) δ ppm 10.43 (br. s, 1H); 8.37 (d, 1H, J=7.8 Hz); 8.31 (d, 1H, J=3.3 Hz); 8.27 (d, 1H, J=6.0 Hz); 8.08 (s, 1H); 8.02 (s, 1H); 7.63 (s, 1H); 7.60 (dd, 1H, J=5.5, 1.5 Hz); 6.79 (d, 1H, J=7.8 Hz); 3.90 (s, 3H); 3.69-3.80 (m, 1H); 3.19-3.29 (m, 1H); 1.80-1.93 (m, 4H); 1.21-1.48 (m, 13H).

Example 7

4-Amino-N-(trans-4-aminocyclohexyl)-7-(2-methoxy-4-pyridinyl)pyrrolo[2,1-f][1,2,4]triazine-5-carboxamide

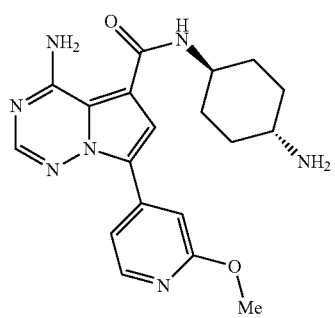

7

7 was prepared from 6A (40 mg, 0.140 mmol) and (trans)-cyclohexane-1,4-diamine (24.02 mg, 0.210 mmol) by the general methods shown for 2D. 7.2HCl (15 mg, 24% yield) was obtained as a white solid after lyopyilization from dil. aq. HCl. HPLC: 8.96 min (YMC S5 ODS, 4.5×50 mm. 1 mL/min, 10-90% methanol-water 0.2% H3PO4, gradient over 15 min). MS (ES): m/z=382.5 [M+H]+. 1H NMR (400 MHz, DMSO-d6) δ ppm 10.85 (br. s, 1H); 8.70-8.77 (m, 1H); 8.63 (d, 1H, J=7.8 Hz); 8.20-8.24 (m, 1H); 8.10-8.15 (m, 2H); 7.96-8.02 (m,3H); 7.51-7.56 (m, 2H); 3.84 (s, 3H); 3.67-3.78 (m, 1H); 2.91-3.02 (m, 1H); 1.84-2.01 (m, 4H); 1.33-1.48 (m, 4H).

Example 8

4-Amino-N-(trans-4-((3-methoxypropanoyl)amino) cyclohexyl)-7-(2-methoxy-4-pyridinyl)pyrrolo[2,1-f][1,2,4]triazine-5-carboxamide

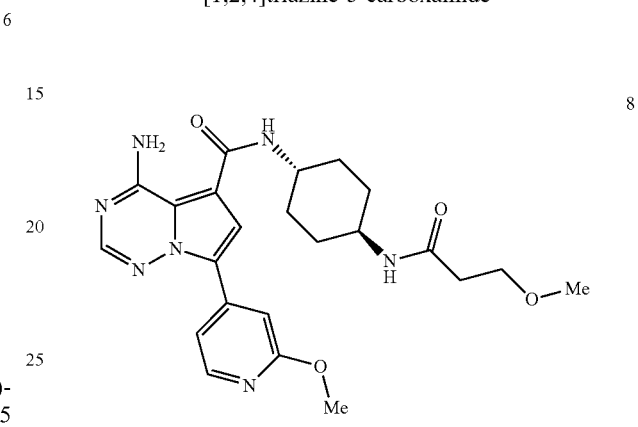

8

8 was prepared from 7 (50 mg, 0.131 mmol) and 3-methoxypropanoic acid (0.016 mL, 0.170 mmol) by the general methods shown for 2D. 6.HCl (10.8 mg, 16% yield) was obtained as a white solid after lyopyilization from dil. aq. HCL. HPLC: 5.19 min. (Sunfire C18 3.0×150 mm 3.5 micron. 0.5 mL/min, 14-95% Acetonitrile-water gradient over 12 min., 0.05% TFA). MS (ES): m/z=468.5 [M+H]+. 1H NMR (400 MHz, DMSO-d6) δ ppm 10.73 (br. s, 1H); 8.57 (br. s, 1H); 8.43 (d, 1H, J=8.0 Hz); 8.21 (d, 1H, J=5.5 Hz); 8.08 (s, 1H); 8.01 (s, 1H); 7.74 (d, 1H, J=7.5 Hz); 7.48-7.56 (m, 2H); 3.84 (s, 3H); 3.71-3.75 (m, 1H); 3.39-3.53 (m, 3H); 3.14 (s, 3H); 2.22 (t, 2H, J=6.4 Hz); 1.77-1.85 (m, 4H); 1.14-1.43 (m, 4H).

Example 9

Methyl cis-4-(((4-amino-7-(2-methoxy-4-pyridinyl)pyrrolo[2,1-f][1,2,4]triazin-5-yl)carbonyl)amino)cyclohexanecarboxylate

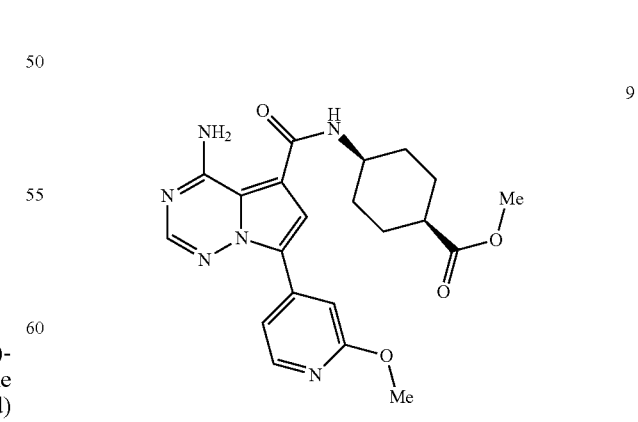

9

9 was prepared from 6A (0.12 g, 0.421 mmol) and (cis)-methyl 4-aminocyclohexanecarboxylate.HCl (0.106 g, 0.547 mmol) by the general methods shown for 2D. 9 (0.056 g, 70% yield) was obtained as a white solid. HPLC: 6.62 min (YMC S5 ODS, 4.6×50 mm. 4 mL/min, 10-90% methanol-water 0.2% H$_3$PO$_4$, gradient over 12 min). MS (ES): m/z=425.3 [M+H]$^+$. $^1$H NMR (400 MHz, DMSO-d$_6$) δ ppm 10.73 (br. s, 1H); 8.35 (br. s, 1H); 8.31 (d, 1H, J=8.0 Hz); 8.27 (d, 1H, J=5.5 Hz); 8.09 (s, 1H); 8.07 (s, 1H); 7.59-7.64 (m, 2H); 3.89-3.94 (m, 4H); 3.66 (s, 3H); 2.61-2.68 (m, 1H); 2.01-2.10 (m, 2H); 1.49-1.79 (m, 6H).

Example 10

(Cis)-4-(((4-amino-7-(2-methoxy-4-pyridinyl)pyrrolo[2,1-f][1,2,4]triazin-5-yl)carbonyl)amino)cyclohexanecarboxylic acid

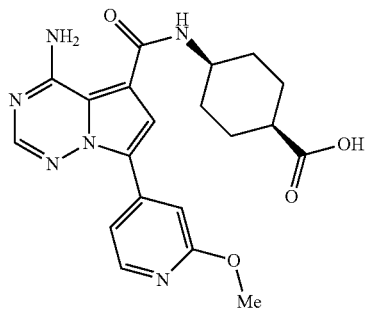

10

10 was prepared from 9 (0.11 g, 0.259 mmol) by the general methods shown for 1C at room temperature. 10 (0.093 g, 87% yield) was obtained as white powder. HPLC: 6.13 min (YMC S5 ODS, 4.6×50 mm. 4 mL/min, 10-90% methanol-water 0.2% H$_3$PO$_4$, gradient over 12 min). MS (ES): m/z=411.2 [M+H]$^+$. $^1$H NMR (400 MHz, DMSO-d$_6$) δ ppm 12.27 (br. s, 1H); 10.46 (br. s, 1H); 8.24-8.33 (m, 3H); 8.08 (s, 1H); 8.07 (s, 1H); 7.59-7.64 (m, 2H); 3.84-3.93 (m, 4H); 2.01-2.10 (m, 2H); 1.50-1.79 (m, 6H) (one proton obscured by solvent peak).

Example 11

4-Amino-N-(cis-4-((2-hydroxy-1,1-dimethylethyl)carbamoyl)cyclohexyl)-7-(2-methoxy-4-pyridinyl)pyrrolo[2,1-f][1,2,4]triazine-5-carboxamide

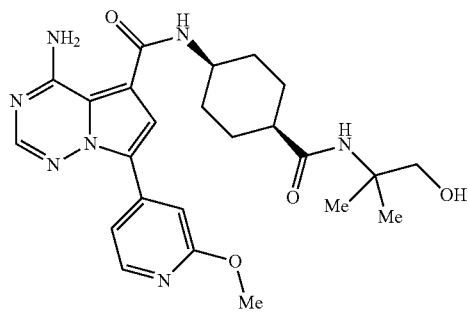

11

11 was prepared from 10 (0.01 g, 0.024 mmol) and 2-amino-2-methylpropan-1-ol (6.52 mg, 0.073 mmol) by the general methods shown for 2D. 11 (0.011 g, 86% yield) was obtained as white solid. HPLC: 10.8 min (Waters X-Bridge Phenyl 4.6×150 mm 3.5 micron, 1 mL/min, 10-90% methanol-water 0.2% H$_3$PO$_4$, gradient over 10 min). MS (ES): m/z=482.4 [M+H]$^+$. $^1$H NMR (400 MHz, DMSO-d$_6$) δ ppm 10.45 (br. s, 1H); 8.25-8.41 (m, 3H); 8.08 (s, 1H); 8.02 (s, 1H); 7.58-7.65 (m, 2H); 7.22 (s, 1H); 3.91 (s, 3H); 3.72-3.84 (m, 1H); 3.38 (d, 2H, J=5.8 Hz); 2.2.09-2.19 (m, 1H); 1.88-1.98 (m, 2H); 1.73-1.81 (m, 2H); 1.31-1.50 (m, 4H); 1.18 (s, 6H).

Example 12

4-Amino-N-(trans-4-(cyclopropylmethoxy)cyclohexyl)-7-(2-methoxy-4-pyridinyl)pyrrolo[2,1-f][1,2,4]triazine-5-carboxamide

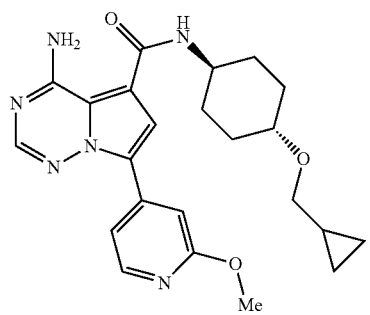

12

12A: 2-((trans)-4-Hydroxycyclohexyl)isoindoline-1,3-dione

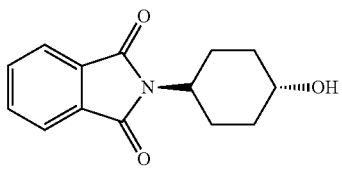

12A

A mixture of (trans)-4-aminocyclohexanol, HCl (5 g, 33.0 mmol) and ethyl 1,3-dioxoisoindoline-2-carboxylate (7.23 g, 33.0 mmol) in water (50 mL) was treated with K$_2$CO$_3$ (11.39 g, 82 mmol) and stirred at room temperature for 1 h. The mixture became very viscous, more water (50 mL) was added and it was stirred for another 2 h. The white solid was collected by filtration, washed with water, and air-dried to provide 12A (6.52 g, 81% yield). $^1$H NMR (400 MHz, DMSO-d$_6$) δ ppm 7.66-7.84 (m, 4H); 4.56 (br. s, 1H); 3.79-3.93 (m, 1H); 3.29-3.45 (m, 1H); 1.97-2.14 (m, 2H); 1.76-1.91 (m, 2H); 1.50-1.67 (m, 2H); 1.09-1.28 (m, 2H).

12B: 2-((trans)-4-(tert-Butyldimethylsilyloxy)cyclohexyl)isoindoline-1,3-dione

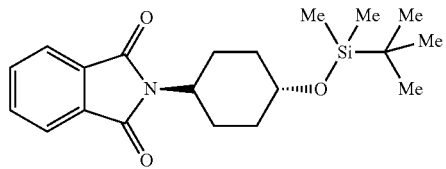

To a stirred solution of 12A (6.5 g, 26.5 mmol) in DMF (20 mL) was added imidazole (3.61 g, 53.0 mmol), followed by tert-butylchlorodimethylsilane in toluene (9.22 mL, 26.5 mmol) portionwise while cooling with an ice bath. Upon completion of the addition, the resulting mixture was stirred at 40° C. for 3 h. There was still some starting material left, so more 50% tert-butylchlorodimethylsilane in toluene (2.5 mL) was added, and the mixture was stirred briefly at room temperature. The mixture was diluted with water and extracted with hexane (3×). The combined organic extracts were washed with brine, dried over anhydrous magnesium sulfate and concentrated under reduced pressure to provide 12B (9.1 g, 96% yield) as a white solid. MS (ES): m/z=360.1 [M+H]$^+$. $^1$H NMR (400 MHz, CDCl$_3$) δ ppm 7.74 (dd, 2H, J=5.5, 3.1 Hz); 7.62 (dd, 2H, J=5.5, 3.1 Hz); 3.96-4.15 (m, 1H); 3.56-3.72 (m, 1H); 2.17-2.29 (m, 2H); 1.85-1.92 (m, 2H); 1.61-1.69 (m, 2H); 1.31-1.43 (m, 2H); 0.82 (s, 9H); 0.00 (s, 6H).

12C: 2-((trans)-4-(Cyclopropylmethoxy)cyclohexyl)isoindoline-1,3-dione

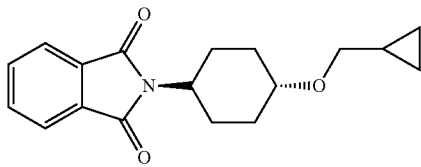

A stirred solution of 12B (750 mg, 2.086 mmol) in acetonitrile (10 mL) was treated with triethylsilane (0.432 mL, 2.71 mmol) and tribromobismuthine (94 mg, 0.209 mmol), followed by slow addition of cyclopropanecarbaldehyde (175 mg, 2.503 mmol) (dissolved in acetonitrile (0.5 mL)). The reaction mixture was stirred at room temperature overnight. The dark solid was removed by filtration, the filtrate was concentrated, and the residue was purified by ISCO silica column (24 g), gradient elution with ethyl acetate:hexane (0%-100% ethyl acetate over 15 min). Concentration of the desired fractions yielded 12C (630 mg, 2.104 mmol, >quantitative yield) as a white solid. MS (ES): m/z=322 [M+Na]$^+$. $^1$H NMR (400 MHz, CDCl$_3$) δ ppm 7.56-7.65 (m, 2H); 7.46-7.53 (m, 2H); 3.89-3.99 (m, 1H); 3.13-3.22 (m, 1H); 3.12 (d, 2H, J=6.8 Hz); 2.04-2.16 (m, 2H); 1.92-2.00 (m, 2H); 1.52-1.61 (m, 2H); 1.14-1.27 (m, 2H); 0.80-0.92 (m, 1H); 0.30-0.39 (m, 2H); −0.02-0.05 (m, 2H).

12D: (trans)-4-(Cyclopropylmethoxy)cyclohexanamine

A stirred solution of 12C (620 mg, 2.071 mmol) in EtOH (10 mL) was treated with hydrazine monohydrate (0.152 mL, 3.11 mmol) and stirred at 70° C. for 1 h. The reaction was judged complete by LCMS. Upon cooling, Et$_2$O was added, and reaction was stirred at room temperature for 1 h. The resulting white solid was removed by filtration, and the filtrate was concentrated. The residue was triturated with Et$_2$O, the small amount of white solid was filtered, and the filtrate was concentrated to provide 12D (120 mg, 34% yield) as pale brown oil. $^1$H NMR (400 MHz, CDCl$_3$) δ ppm 3.11 (d, 2H, J=6.8 Hz); 2.99-3.08 (m, 1H); 2.48-2.57 (m, 1H); 1.64-1.89 (m, 6H); 1.06-1.18 (m, 2H); 0.81-1.02 (m, 3H); 0.31-0.39 (m, 2H); −0.02-0.04 (m, 2H).

12: 4-Amino-N-(trans-4-(cyclopropylmethoxy)cyclohexyl)-7-(2-methoxy-4-pyridinyl)pyrrolo[2,1-f][1,2,4]triazine-5-carboxamide

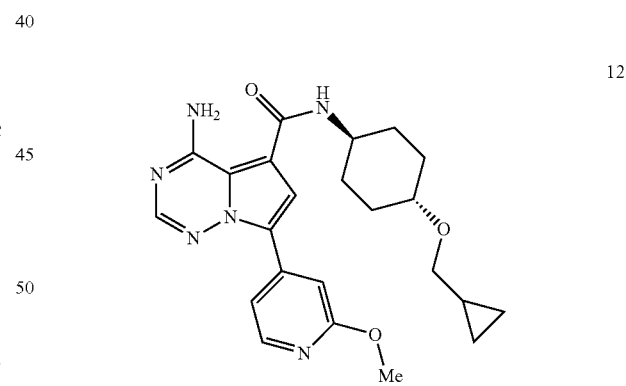

12 was prepared from 6A (35 mg, 0.123 mmol) and 12D (27.0 mg, 0.160 mmol) by the general methods shown for 2D. 12.TFA (17.8 mg, 0.032 mmol, 26% yield) was obtained as off-white solid. HPLC: 7.48 min (Sunfire C18 3.0×150 mm 3.5 micron. 0.5 mL/min, 14-95% Acetonitrile-water gradient over 12 min., 0.05% TFA). MS (ES): m/z=437.1 [M+H]$^+$. $^1$H NMR (500 MHz, DMSO-d$_6$) δ ppm 10.41 (br. s, 1H); 8.23-8.31 (m, 1H); 8.20 (d, 1H, J=7.8 Hz); 8.11 (d, 1H, J=5.3 Hz); 7.95 (s, 1H); 7.87 (s, 1H); 7.40-7.48 (m, 2H); 3.75 (s, 3H); 3.65 (dt, 1H, J=7.7, 3.8 Hz); 3.03-3.16 (m, 3H); 1.87 (br. s, 2H); 1.76 (br. s, 2H); 1.19-1.32 (m, 2H); 1.03-1.16 (m, 2H); 0.75-0.86 (m, 1H); 0.24-0.34 (m, 2H); −0.09-0.04 (m, 2H).

Example 13

4-Amino-N-(trans-4-(5-(methoxymethyl)-1H-pyrazol-3-yl)cyclohexyl)-7-(2-methoxy-4-pyridinyl)pyrrolo[2,1-f][1,2,4]triazine-5-carboxamide

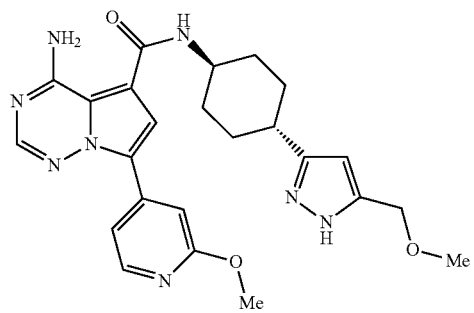

13A: (trans)-Ethyl 4-aminocyclohexanecarboxylate

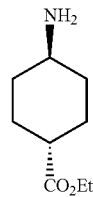

A suspension of (trans)-4-aminocyclohexanecarboxylic acid (5 g, 34.9 mmol) in EtOH (100 mL, 1713 mmol) was treated with HCl (9.09 mL, 105 mmol) and the mixture was stirred at 60° C. overnight. The reaction mixture turned to clear solution. It was concentrated under reduced pressure and the residue was triturated with Et$_2$O in CH$_3$CN (50%) and the resulting white solid was collected. There was some product left in the filtrate so it was concentrated and triturated with Et$_2$O in CH$_3$CN (50%), the white solid was collected by filtration and combined with the white solid that was collected previously to provide 13A.HCl (5.25 g, 25.3 mmol, 72.4% yield). $^1$H NMR (400 MHz, CDCl$_3$) δ ppm 4.06 (q, 2H, J=7.1 Hz); 3.01-3.15 (m, 1H); 1.34-2.31 (m, 9H); 1.18 (t, 3H, J=7.1 Hz).

13B: (trans)-Ethyl 4-(dibenzylamino)cyclohexanecarboxylate

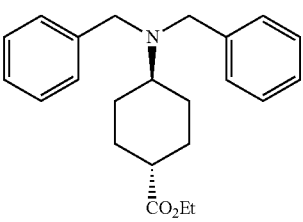

A stirred suspension of 13A.HCl (5.12 g, 24.65 mmol) in acetonitrile (75 mL) was treated with K$_2$CO$_3$ (13.63 g, 99 mmol) and (bromomethyl)benzene (7.32 mL, 61.6 mmol). The resulting suspension was stirred at 80° C. overnight. Upon cooling, the solid was filtered off and filtrate was concentrated. The residue was purified by Isco silica column (80 g) eluted with ethyl acetate-hexane: 0%-20%. Concentration of the appropriate fractions provided 13B (7.92 g, 91% yield) as a colorless oil. MS (ES): m/z=352.2 [M+H]$^+$. $^1$H NMR (400 MHz, CDCl$_3$) δ ppm 7.08-7.34 (m, 10H); 4.01 (q, 2H, J=7.1 Hz); 3.55 (s, 4H); 2.40-2.49 (m, 1H); 2.06-2.14 (m, 1H); 1.86-2.00 (m, 2H); 1.24-1.38 (m, 2H); 1.18 (t, 3H, J=7.1 Hz).

13C: (trans)-4-(Dibenzylamino)cyclohexanecarboxylic acid

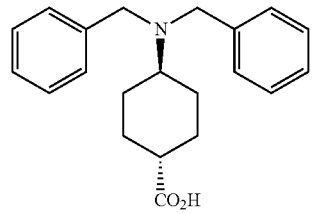

A mixture of 13B (6.8 g, 19.35 mmol) in THF (25 mL) and water (5.00 mL) was treated LiOH.H$_2$O (4.06 g, 97 mmol) and stirred at room temperature over a weekend. The reaction mixture was concentrated to halfvolume and acidified with 1.0N HCl carefully to ~pH6. The resulting white solid was collected by filtration and air dried to provide 13C (5.0 g, 80% yield). MS (ES): m/z=324.3 [M+H]$^+$. $^1$H NMR (400 MHz, CDCl$_3$) δ ppm 7.17-7.47 (m, 10H); 3.64 (s, 4H); 2.46-2.61 (m, 1H); 2.17-2.33 (m, 1H); 1.92-2.15 (m, 4H); 1.28-1.52 (m, 4H).

13D: (trans)-4-(Dibenzylamino)-N-methoxy-N-methylcyclohexanecarboxamide

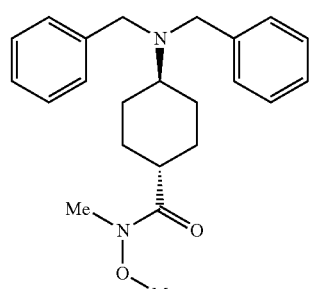

A reaction mixture of 13C (1 g, 3.09 mmol) in DMF (5 mL) was treated with N,O-dimethylhydroxylamine.HCl (0.452 g, 4.64 mmol), BOP (1.778 g, 4.02 mmol) and triethylamine (1.293 mL, 9.28 mmol). The reaction mixture was stirred at room temperature overnight. The mixture was diluted with water and the resulting white solid was collected by filtration, and rinsed with water and air dried to provide 13D (1.2 g, >quantitative yield) as a white solid. $^1$H NMR (400 MHz, CDCl$_3$) δ ppm 7.29 (d, 4H, J=7.0 Hz); 7.17-7.26 (m, 4H); 7.10-7.16 (m, 2H); 3.61 (s, 3H); 3.56 (s, 4H); 3.08 (s, 3H); 2.44-2.59 (m, 2H); 1.85-1.95 (m, 2H); 1.70-1.82 (m, 2H); 1.28-1.45 (m, 4H).

13E: 1-((trans)-4-(Dibenzylamino)cyclohexyl)-4-methoxybut-2-yn-1-one

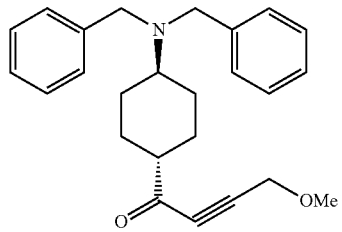

13E

A stirred solution of 3-methoxyprop-1-yne (0.207 ml, 2.456 mmol) in THF (2 mL) was treated with BuLi (1.535 ml, 2.456 mmol) dropwise at −78° C. After stirring for 15 min, 13D (300 mg, 0.819 mmol) in THF (2 mL) was added and reaction mixture was warmed to room temperature over 30 min. The reaction was quenched with aq. HOAc and extracted with ethyl acetate (3×). The combined organics were washed with brine, dried over anhydrous magnesium sulphate and concentrated under reduced pressure. The residue was purified by Isco silica column (12 g), eluted with ethyl acetate:hexane, 0-70%. Concentration of the appropriate fractions provided 13E (300 mg, 98% yield). This material was taken without characterization to the next step.

13F: (trans)-N,N-Dibenzyl-4-(5-(methoxymethyl)-1H-pyrazol-3-yl)cyclo hexanamine

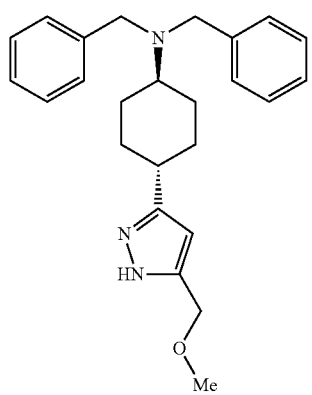

13F

A stirred solution of 13E (150 mg, 0.399 mmol) in EtOH (2 mL) was treated with hydrazine (0.116 mL, 2.397 mmol), and stirred overnight at 75° C. Upon cooling, water was added, the mixture was stirred for 1 h, the resulting white solid was collected by filtration and air dried to yield 13F (125 mg, 80% yield). MS (ES): m/z=390.3 [M+H]$^+$. $^1$H NMR (400 MHz, CDCl$_3$) δ ppm 7.31 (d, 4H, J=7.0 Hz); 7.18-7.25 (m, 4H); 7.14 (t, 2H, J=7.3 Hz); 5.92 (s, 11H); 4.35 (s, 2H); 3.58 (s, 4H); 3.30 (s, 3H); 2.44-2.55 (m, 2H); 1.89-2.01 (m, 4H); 1.23-1.50 (m, 4H).

13G: (trans)-4-(5-(Methoxymethyl)-1H-pyrazol-3-yl)cyclohexanamine

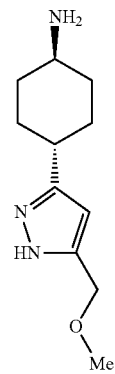

13G

To a Parr shaker bottle containing 13F (110 mg, 0.282 mmol) and EtOH (10 mL), was added palladium hydroxide on carbon (39.7 mg, 0.282 mmol). The mixture was purged with H$_2$, and the bottle was shaken overnight under H$_2$ (45 psi). The catalyst was removed by filtration and the filtrate was concentrated to provide 13G (57 mg, 96% yield) as a colorless gummy solid. MS (ES): m/z=210.2 [M+H]$^+$.

13: 4-Amino-N-(trans-4-(5-(methoxymethyl)-1H-pyrazol-3-yl)cyclohexyl)-7-(2-methoxy-4-pyridinyl)pyrrolo[2,1-f][1,2,4]triazine-5-carboxamide

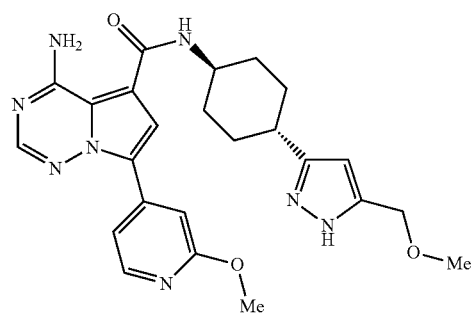

13

13 was prepared from 6A (40 mg, 0.140 mmol) and 13G (44.0 mg, 0.210 mmol) by the general methods shown for 2D. 13.TFA (51.9 mg, 63% yield) was obtained as off-white solid. HPLC: 5.53 min (Sunfire C18 3.0×150 mm 3.5 micron. 0.5 mL/min, 14-95% Acetonitrile-water gradient over 12 min., 0.05% TFA). MS (ES): m/z=477.3 [M+H]$^+$. $^1$H NMR (400 MHz, DMSO-d$_6$) δ ppm 10.60 (br. s, 1H); 8.40 (d, 2H, J=7.9 Hz); 8.21 (d, 1H, J=5.5 Hz); 8.05 (s, 1H); 7.99 (s, 1H);

7.50-7.57 (m, 2H); 5.99 (s, 1H); 4.25 (s, 2H); 3.77-3.88 (m, 4H); 3.18 (s, 3H); 2.51-2.63 (m, 2H); 1.87-2.02 (m, 4H); 1.38-1.52 (m, 4H).

Example 14

4-Amino-N-(trans-4-(4-(2-methoxyethyl)-4H-1,2,4-triazol-3-yl)cyclohexyl)-7-(2-methoxy-4-pyridinyl)pyrrolo[2,1-f][1,2,4]triazine-5-carboxamide

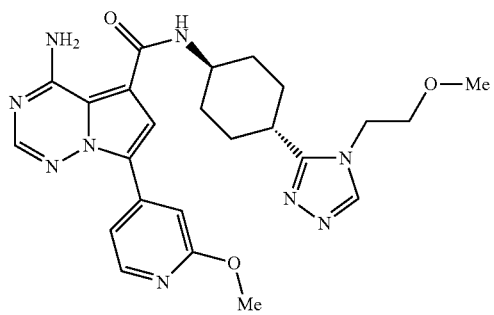

14A: (trans)-4-(Dibenzylamino)cyclohexanecarbohydrazide

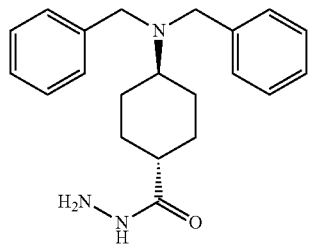

A solution of 13B (750 mg, 2.134 mmol) in ethanol (5 mL) was treated with hydrazine.H₂O (1.036 mL, 21.34 mmol), stirred at 80° C. for 2 h. No product was observed so more hydrazine.H₂O (1.036 mL, 21.34 mmol) was added, and the solution was stirred at 150° C. in sealed tube overnight. Upon cooling, water was added and the resulting white solid was collected by filtration, washed with water and air dried to provide 14A (754 mg, >quantitative yield) as a white solid. MS (ES): m/z=338.3 [M+H]⁺. ¹H NMR (400 MHz, CDCl₃) δ ppm 7.16-7.40 (m, 10H); 6.58 (br. s, 1H); 3.76 (br. s, 2H); 3.55 (s, 4H); 2.42-2.51 (m, 1H); 1.79-1.97 (m, 5H); 1.25-1.42 (m, 4H).

14B: (trans)-N,N-Dibenzyl-4-(4-(2-methoxyethyl)-4H-1,2,4-triazol-3-yl)cyclohexanamine

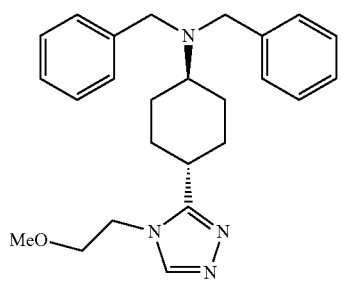

14A (300 mg, 0.889 mmol) was treated with acetonitrile (2 mL) and THF (0.5 mL). This clear solution was treated with N,N-dimethylformamide dimethylacetal (0.30 mL, 2.22 mmol) and the reaction mixture was stirred at 50° C. for 45 min. The mixture was treated with 2-methoxyethanamine (0.230 mL, 2.67 mmol) resulting in a yellow clear solution. Acetic acid (0.5 mL, 8.73 mmol) was added, and the reaction was stirred at 90° C. overnight. The reaction was diluted with water and extracted with 25% MeOH in dichloromethane (3×). The combined organic extracts were washed with brine, dried over anhydrous sodium sulphate and concentrated under reduced pressure. The residue was purified by Isco silica column (12 g), (gradient elution with methanol-dichloromethane over 12 min.) Concentration of the appropriate fractions provided 14B (300 mg, 0.742 mmol, 83% yield) as a pale yellow oil. MS (ES): m/z=405.2 [M+H]⁺.

14C: (trans)-4-(4-(2-Methoxyethyl)-4H-1,2,4-triazol-3-yl)cyclohexanamine

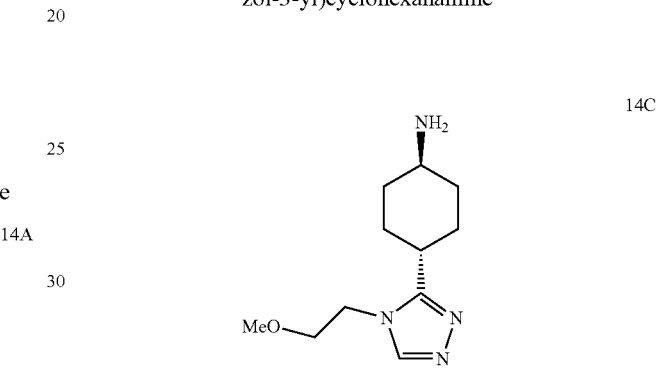

14C was prepared from 14B (300 mg, 0.742 mmol) by the general methods shown for 13G then converted to the HCl salt by treatment with 1N HCl in ether. 14C.HCl (150 mg, 77%) was obtained as a viscous oil. MS (ES): m/z=225 [M+H]⁺.

14: 4-Amino-N-(trans-4-(4-(2-methoxyethyl)-4H-1,2,4-triazol-3-yl)cyclohexyl)-7-(2-methoxy-4-pyridinyl)pyrrolo[2,1-f][1,2,4]triazine-5-carboxamide

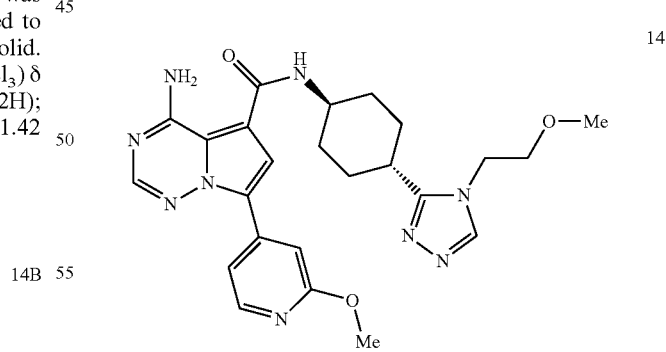

14 was prepared from 6A (30 mg, 0.105 mmol) and 14C.HCl (35.7 mg, 0.137 mmol) by the general methods shown for 2D. 14.TFA (9.2 mg, 0.015 mmol, 14% yield) was obtained as pale yellow fluffy solid. HPLC: 4.50 min (Sunfire C18 3.0×150 mm 3.5 micron. 0.5 mL/min, 14-95% Acetonitrile-water gradient over 12 min., 0.05% TFA). MS (ES): m/z=492.2 [M+H]⁺. ¹H NMR (400 MHz, DMSO-d₆) δ ppm 10.40 (br. s, 1H); 8.87 (s, 1H); 8.40 (d, 1H, J=7.7 Hz); 8.30 (br.

s, 1H); 8.20 (d, 1H, J=5.5 Hz); 8.03 (s, 1H); 7.97 (s, 1H); 7.49-7.59 (m, 2H); 4.27 (t, 2H, J=5.0 Hz); 3.84 (s, 3H); 3.60 (t, 2H, J=5.0 Hz); 3.22 (s, 3H); 2.88-3.01 (m, 1H); 1.94-1.99 (m, 4H); 1.56-1.71 (m, 2H); 1.45-1.53 (m, 2H).

Example 15

3-((trans-4-(((4-Amino-7-(2-methoxy-4-pyridinyl)pyrrolo[2,1-f][1,2,4]triazin-5-yl)carbonyl)amino)cyclohexyl)amino)-2,2-dimethyl-3-oxopropyl 4-morpholinecarboxylate

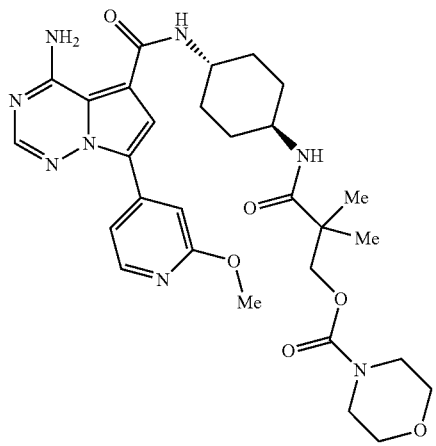

15A: tert-Butyl (trans)-4-(4-methoxybenzylamino)cyclohexylcarbamate

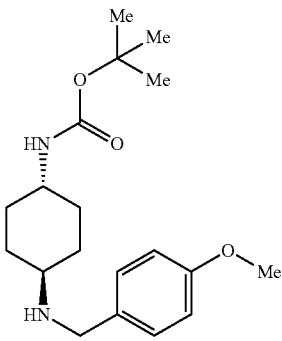

A suspension of tert-butyl (trans)-4-aminocyclohexylcarbamate (1.0 g, 4.67 mmol) in dichloromethane (30 mL) was treated with 4-methoxybenzaldehyde (0.568 mL, 4.67 mmol) and magnesium perchlorate (0.052 g, 0.233 mmol) and stirred at room temperature overnight. A large excess of solid Na$_2$SO$_4$ was added, and the reaction mixture was stirred for 1 h., filtered, and the filter cake was rinsed with MeOH. The filtrate and rinse were combined and concentrated to yield a white solid, which was dissolved in MeOH (10 mL). This solution was treated with NaBH$_4$ (0.265 g, 7.00 mmol) in a single portion. The reaction mixture became a light yellow solution which was stirred at room temperature for 1.5 h. The reaction was quenched with 1.0N NaOH, diluted with water (150 mL), and stirred for 30 min. The resulting white solid was collected by filtration, washed with water, and air dried to provide 15A (1.26 g, 81% yield). MS (ES): m/z=335 [M+H]$^+$. $^1$H NMR (400 MHz, DMSO-d$_6$) δ ppm 7.20 (d, 2H, J=8.5 Hz); 6.83 (d, 2H, J=8.5 Hz); 6.63 (d, 1H, J=8.0 Hz); 3.70 (s, 2H); 3.60 (br. s, 1H); 3.31 (s, 3H); 3.08-3.18 (m, 1H); 2.06-2.25 (m, 1H); 1.65-1.88 (m, 4H); 1.34 (s, 9H); 0.93-1.12 (m, 4H).

15B: tert-Butyl (trans)-4-(3-chloro-N-(4-methoxybenzyl)-2,2-dimethyl propanamido)cyclohexylcarbamate

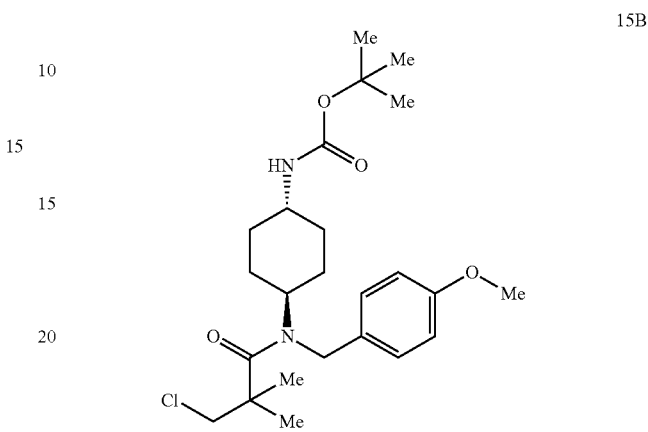

A stirred solution of 15A (200 mg, 0.598 mmol) in dichloromethane (5 mL) was treated with triethylamine (0.208 mL, 1.495 mmol), followed by slow addition of 3-chloro-2,2-dimethyl propanoyl chloride (0.155 mL, 1.196 mmol) at room temperature. After stirring for 2 h, reaction was judged complete by LCMS. It was washed with water, and the organics were dried over anhydrous sodium sulphate and concentrated under reduced pressure. The crude product was purified by Isco silica column (24 g) eluted with ethyl acetate:hexane, 0%-100%. Concentration of the appropriate fractions yielded 15B (226 mg, 83% yield) as a white foam. MS (ES): m/z=453.2 [M+H]$^+$. $^1$H NMR (400 MHz, DMSO-d$_6$) δ ppm 7.02 (d, 2H, J=8.5 Hz); 6.75 (d, 2H, J=8.5 Hz); 4.41 (s, 2H); 4.22-4.30 (m, 1H); 3.88-3.98 (m, 1H); 3.72 (s, 3H); 3.69 (s, 2H); 3.19-3.30 (m, 1H); 1.92-2.02 (m, 2H); 1.01-1.69 (m, 23H).

15C: 3-(((trans)-4-(tert-Butoxycarbonylamino)cyclohexyl)(4-methoxy benzyl)amino)-2,2-dimethyl-3-oxopropyl morpholine-4-carboxylate

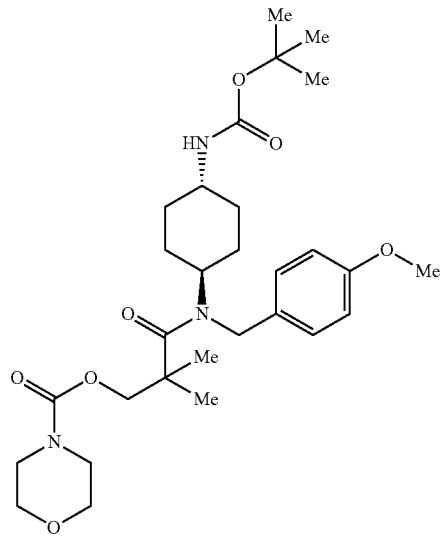

A stirred solution of 15B (75 mg, 0.166 mmol) in DMF (1 mL) was treated with K₂CO₃ (68.6 mg, 0.497 mmol), and morpholine (0.058 mL, 0.662 mmol). The reaction mixture was stirred at 90° C. overnight. The reaction mixture was concentrated and the residue was redissolved into small amount of MeOH, purified by preparative HPLC, (PHENOMENEX® Axia Luna 5 micron 30×100 mm, MeOH-water-TFA gradient). Concentration of the appropriate fractions provided 33 mg (37%) of 15C. MS (ES): m/z=548.2 [M+H]⁺.

15D: 3-((trans)-4-Aminocyclohexylamino)-2,2-dimethyl-3-oxopropyl morpholine-4-carboxylate

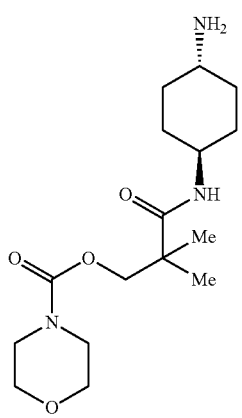

A solution of 15C (30 mg, 0.055 mmol) in dichloromethane (0.5 mL) was treated with TFA (0.5 mL), and stirred at room temperature for 1.5 h. The reaction mixture was concentrated, and the residue was triturated with Et₂O. The resulting off white solid was collected by filtration and air dried to provide 15D. This material was used without purification in the next step.

15: 3-((trans-4-(((4-Amino-7-(2-methoxy-4-pyridinyl)pyrrolo[2,1-f][1,2,4]triazin-5-yl)carbonyl)amino)cyclohexyl)amino)-2,2-dimethyl-3-oxopropyl 4-morpholinecarboxylate

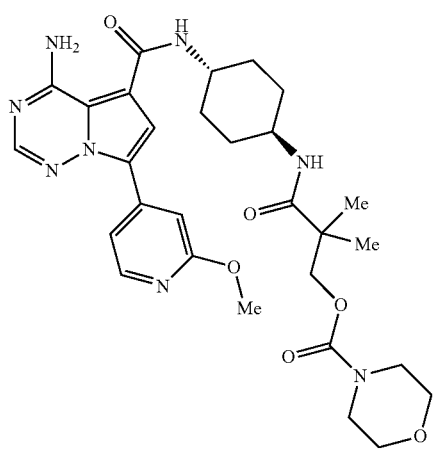

15 was prepared from 6A (17.19 mg, 0.060 mmol) and 15D by the general methods shown for 2D. 15.TFA (8.0 mg, 19% yield) was obtained as white fluffy solid. HPLC: 6.02 min (Sunfire C18 3.0×150 mm 3.5 micron. 0.5 mL/min, 14-95% Acetonitrile-water gradient over 12 min., 0.05% TFA). MS (ES): m/z=595.2 [M+H]⁺. ¹H NMR (400 MHz, DMSO-d₆) δ ppm 10.45 (br. s, 1H.); 8.31-8.45 (m, 2H); 8.20 (d, 1H, J=5.5 Hz); 7.96 (s, 1H); 8.03 (s, 1H); 7.47-7.64 (m, 2H); 7.27 (d, 1H, J=8.3 Hz); 3.92 (s, 2H); 3.84 (s, 3H); 3.62-3.78 (m, 1H); 3.44-3.57 (m, 5H); 3.21-3.30 (m, 4H); 1.64-1.89 (m, 4H); 1.23-1.44 (m, 4H); 1.04 (s, 6H).

Example 16

4-Amino-7-(2-methoxy-4-pyridinyl)-N-(trans-4-((methylsulfonyl)amino)cyclohexyl)pyrrolo[2,1-f][1,2,4]triazine-5-carboxamide

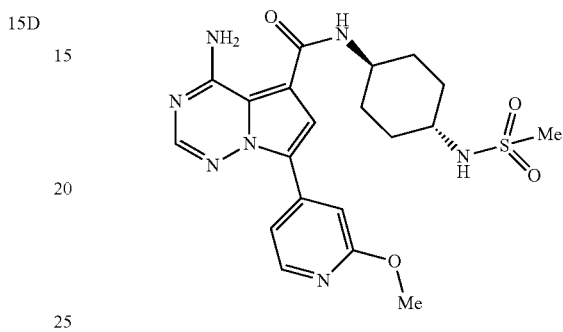

A stirred solution of 7 (20 mg, 0.052 mmol) in DMF (1 mL) was treated with TEA (8.77 µL, 0.063 mmol), followed by methanesulfonyl chloride (4.46 µL, 0.058 mmol) and stirred at room temperature for 30 min. The reaction was incomplete, so more methanesulfonyl chloride (2.0 ul) was added and the reaction was stirred for another 30 min. The reaction mixture was concentrated, and the residue was dissolved in MeOH and purified by preparative HPLC (PHENOMENEX® Axia (Luna 5 micron 30×250 mm, methanol-water-TFA gradient). Concentration of the appropriate fractions provided 16.TFA (15.7 mg, 0.027 mmol, 52% yield) as a white solid. HPLC: 5.45 min (Sunfire C18 3.0×150 mm 3.5 micron. 0.5 mL/min, 14-95% Acetonitrile-water gradient over 12 min., 0.05% TFA). MS (ES): m/z=460.0 [M+H]⁺. ¹H NMR (400 MHz, DMSO-d₆) δ ppm 10.59 (1H, br. s.), 8.42 (m, 2H); 8.27 (1H, d, J=5.5 Hz); 8.11 (s, 1H); 8.03 (s, 1H); 7.55-7.66 (2H, m); 7.06 (1H, d, J=7.28 Hz); 3.91 (s, 3H); 3.69-3.81 (1H, m); 3.07-3.21 (m, 1H); 2.94 (s, 3H); 1.86-2.04 (m, 4H); 1.26-1.54 (m, 4H).

Example 17

Ethyl (trans-4-(((4-amino-7-(2-methoxy-4-pyridinyl)pyrrolo[2,1-f][1,2,4]triazin-5-yl)carbonyl)amino)cyclohexyl)carbamate

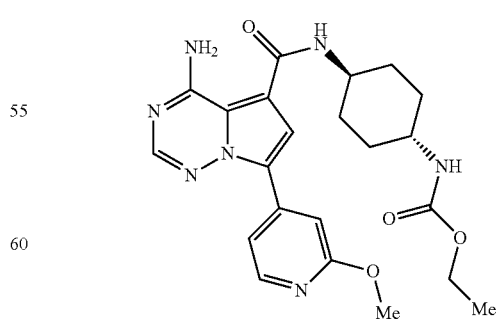

17 was prepared from 7 (20 mg, 0.052 mmol) and ethyl chloroformate by the general methods shown for 16. 17.TFA (6.3 mg, 21% yield) was obtained as a white solid. HPLC:

6.25 min (Sunfire C18 3.0×150 mm 3.5 micron. 0.5 mL/min, 14-95% Acetonitrile-water gradient over 12 min., 0.05% TFA). MS (ES): m/z=454.1 [M+H]$^+$. $^1$H NMR (400 MHz, DMSO-d$_6$) δ ppm 10.53 (br. s, 1H); 8.36-8.42 (m, 2H); 8.27 (d, 1H, J=6.0 Hz); 8.10 (s, 1H); 8.03 (s, 1H); 7.56-7.65 (m, 2H); 7.06 (s, 1H); 3.97 (q, 2H, J=7.2 Hz), 3.91 (s, 3H); 3.69-3.83 (m, 1H); 3.22-3.34 (m, 1H); 1.81-1.97 (m, 4H); 1.35-1.51 (m, 2H), 1.21-1.35 (m, 2H); 1.17 (t, 3H, J=7.2 Hz).

Example 18

4-Amino-7-(2-methoxy-4-pyridinyl)-N-(trans-4-((methylcarbamoyl)amino)cyclohexyl)pyrrolo[2,1-f][1,2,4]triazine-5-carboxamide

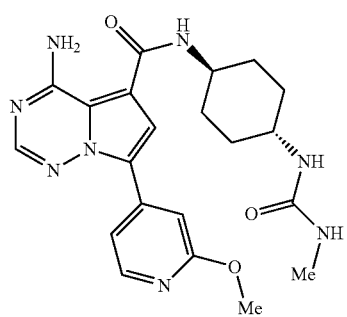

18

A suspension of 7 (20 mg, 0.052 mmol) in DMF (1 mL) was treated with isocyanatomethane (2.99 mg, 0.052 mmol) and stirred at room temperature for 1 h. Reaction was judged complete by LCMS (two peaks were detected, one desired product and the other di-substituted product as side product). The reaction mixture was concentrated and the residue was dissolved in DMSO (hot) and purified by preparative HPLC (PHENOMENEX® Axia (Luna 5 micron 30×250 mm, MeOH-water-TFA gradient) Concentration of appropriate fractions provided 18.TFA (6.3 mg, 22% yield) as a white solid. HPLC: 4.78 min (Sunfire C18 3.0×150 mm 3.5 micron. 0.5 mL/min, 14-95% Water-Acetonitrile gradient over 12 min., 0.05% TFA). MS (ES): m/z=439.1 [M+H]$^+$. $^1$H NMR (400 MHz, DMSO-d$_6$) δ ppm 10.60 (br. s, 1H); 8.43-8.47 (m, 1H); 8.41 (d, 1H, J=8.0 Hz); 8.27 (1H, d, J=4.8 Hz); 8.10-8.16 (m, 1H); 8.04 (s, 1H); 7.62 (br. s, 1H); 7.60 (dd, 1H, J=5.5, 1.5 Hz); 3.91 (s, 3H); 3.72-3.85 (m, 1H); 3.29-3.42 (m, 1H); 2.54 (s, 3H); 1.83-1.94 (m, 4H); 1.37-1.51 (m, 2H); 1.14-1.29 (m, 2H).

Example 19

4-Amino-N-(3-(tert-butoxycarbonylamino)propyl)-7-(4-pyridinyl)pyrrolo[2,1-f][1,2,4]triazine-5-carboxamide

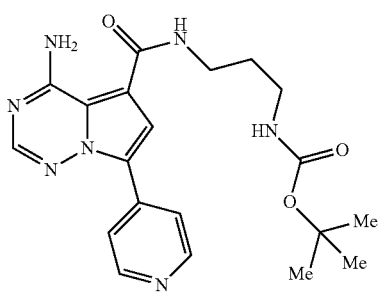

19

19A: 4-Amino-N-(3-(tert-butoxycarbonylamino)propyl)-7-bromopyrrolo[2,1-f][1,2,4]triazine-5-carboxamide

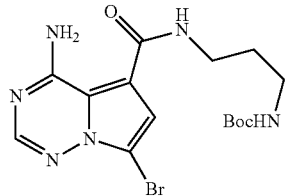

19A 19A was prepared from 2C (82 mg, 0.32 mmol) and N-Boc-1,3-diaminopropane (67 mg, 0.38 mmol) by the general methods shown for 2D. 19A (99 mg, 75% yield) was obtained as a white powder. HPLC: 6.34 min (YMC S5 ODS, 4.5×50 mm. 4 mL/min, 10-90% methanol-water 0.2% H$_3$PO$_4$, gradient over 12 min). MS (ES): m/z=413 [M+H]$^+$.

19: 4-Amino-N-(3-(tert-butoxycarbonylamino)propyl)-7-(4-pyridinyl)pyrrolo[2,1-f][1,2,4]triazine-5-carboxamide

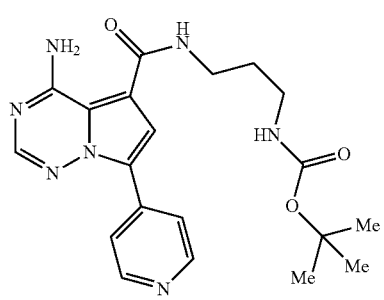

19

19 was prepared from 19A (90 mg, 0.22 mmol) and pyridine-4-boronic acid (40 mg, 0.33 mmol) by the general method shown for 3. 19-TFA (80 mg, 64% yield) was obtained as a white powder. HPLC: 10.2 min (Waters Sunfire, 4.6×150 mm. 1 mL/min, 10-90% methanol-water 0.2% H$_3$PO$_4$, gradient over 10 min). MS (ES): m/z=412 [M+H]$^+$. $^1$H NMR (400 MHz, DMSO-d$_6$) δ ppm 10.51 (br. s, 1H); 8.88 (d, 2H, J=6.8 Hz); 8.76 (br. t, 1H, J=5.5 Hz); 8.56 (br. s, 1H); 8.51 (d, 2H, J=6.8 Hz); 8.22 (s, 1H); 8.19 (s, 1H); 6.88 (br. t, 1H, J=5.6 Hz); 3.28-3.38 (m, 2H); 2.95-3.03 (m, 2H); 1.63-1.72 (m, 2H); 1.86 (s, 9H).

Example 20

4-Amino-N-(3-aminopropyl)-7-(4-pyridinyl)pyrrolo[2,1-f][1,2,4]triazine-5-carboxamide

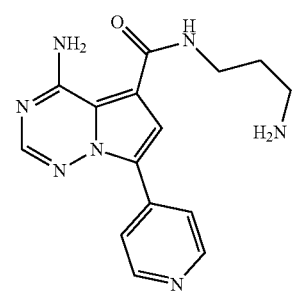

20

20 was prepared from 19 (40 mg, 0.097 mmol) by the general method shown for 15D. 20.2TFA (10 mg, 19% yield) was obtained as a sticky, off-white solid. HPLC: 0.83 min (YMC S5 ODS, 4.5×50 mm. 4 mL/min, 10-90% methanol-water 0.2% $H_3PO_4$, gradient over 12 min). MS (ES): m/z=312 [M+H]+. 1H NMR (400 MHz, DMSO-$d_6$+MeOH-$d_4$) δ ppm 8.81 (d, 2H, J=6.8 Hz); 8.41 (d, 2H, J=6.5 Hz); 8.18 (s, 1H); 8.09 (s, 1H); 3.39 (t, 2H, J=6.5 Hz); 2.87 (t, 2H, J=7.7 Hz); 1.80-1.89 (m, 2H).

Example 21

4-Amino-N-(3-(3,4-difluorobenzylamino)propyl)-7-(4-pyridinyl)pyrrolo[2,1-f][1,2,4]triazine-5-carboxamide

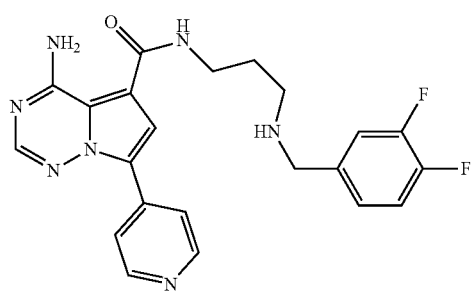

To a stirred suspension of 20 (20 mg, 0.052 mmol) and 3,4-difluorobenzaldehyde (7.4 mg, 0.052 mmol) in 2 mL of dichloromethane was added 5 mg of sodium acetate followed by 0.052 mL (0.052 mmol) of a 1M solution of (i-PrO)$_3$TiCl in hexanes. The mixture was stirred 20 min. then treated with sodium triacetoxyborohydride (20 mg, 0.1 mmol). This mixture was stirred 1 h then treated with an additional 5 mg of 3,4-difluorobenzaldehyde and 20 mg more sodium triacetoxyborohydride. The reaction was stirred an additional 1 h, diluted with aq. sodium carbonate, and ext. twice with chloroform. The chloroform extracts were combined, dried, and concentrated. The resulting crude product was purified by prep. HPLC to afford 4 mg (12%) of 21.2TFA as an off-white solid. HPLC: 7.48 min (Waters Sunfire, 4.6×150 mm. 1 mL/min, 10-90% methanol-water 0.2% $H_3PO_4$, gradient over 10 min). MS (ES): m/z=438 [M+H]+. 1H NMR (400 MHz, MeOH-$d_4$) δ ppm 8.75 (d, 2H, J=5.3 Hz); 8.67 (d, 2H, J=6.3 Hz); 8.13 (s, 1H); 8.03 (s, 1H); 7.29-7.49 (m, 3H); 4.23 (s, 2H); 3.66 (t, 2H, J=6.5 Hz); 3.16 (t, 2H, J=7.4 Hz); 2.00-2.09 (m, 2H).

Example 22

4-Amino-7-(2-methoxy-4-pyridinyl)-N-(trans-4-(pyrimidin-2-yl amino)cyclohexyl)pyrrolo[2,1-f][1,2,4]triazine-5-carboxamide

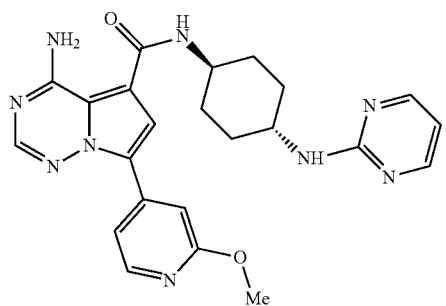

22A: (trans)-$N^1$-(Pyrimidin-2-yl)cyclohexane-1,4-diamine

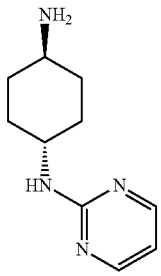

A stirred mixture of trans-1,4-cyclohexanediamine (1.50 g, 13.1 mmol) and 2-chloropyrimidine (500 mg, 4.37 mmol) was heated at 160° C. for 2 h then cooled to RT. The mixture was diluted with water, filtered, and the aqueous phase was extracted three times with ethyl acetate. The combined organic extracts were dried over sodium sulfate and concentrated to afford 22A (235 mg, 28%). MS (ES): m/z=193 [M+H]+.

22: 4-Amino-7-(2-methoxy-4-pyridinyl)-N-(trans-4-(pyrimidin-2-yl amino)cyclohexyl)pyrrolo[2,1-f][1,2,4]triazine-5-carboxamide

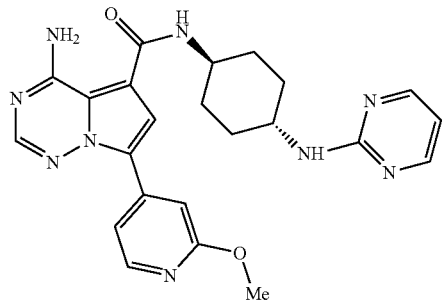

22 was prepared from 6A (50 mg, 0.175 mmol) and 22A (34 mg, 0.175 mmol) using the general method shown for 2D. 22 (19 mg, 24%) was obtained as a white solid. HPLC: 4.76 min. (Sunfire, C18 3.0×150 mm 3.5 micron. 0.5 mL/min, 14-95% Acetonitrile-water, 0.05% TFA gradient over 12 min.). MS (ES): m/z=460 [M+H]+. 1H NMR (400 MHz, MeOH-$d_4$) δ ppm 10.51 (br. s, 1H); 8.34-8.40 (m, 2H); 8.26 (d, 2H, J=4.6 Hz); 8.21 (d, 1H, J=5.5 Hz); 8.04 (s, 1H); 7.97 (s, 1H); 7.50-7.57 (m, 2H); 7.29 (br. s, 1H); 6.54 (t, 1H, J=4.8 Hz); 3.62-3.81 (m, 2H); 1.82-1.97 (m, 4H); 1.28-1.47 (m, 4H).

Example 23

(+/−)-4-Amino-N-(cis-4-hydroxycyclohepyl)-7-(2-methoxy-4-pyridinyl)pyrrolo[2,1-f][1,2,4]triazine-5-carboxamide

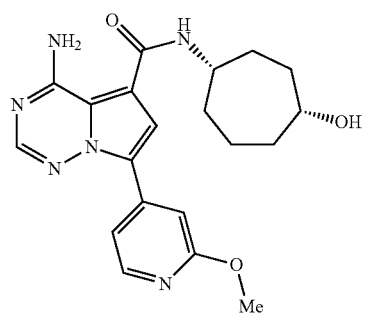

23A: (+/−)-tert-Butyl 6-oxa-7-azabicyclo[3.2.2]non-8-ene-7-carboxylate

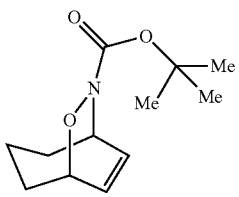

(1Z,3Z)-Cyclohepta-1,3-diene (3.54 g, 37.6 mmol) was dissolved in methylene chloride (36 mL) in a flask equipped with a dropping funnel under nitrogen. Tetrabutylammonium periodate (16.29 g, 37.6 mmol) was added and the reaction was cooled to 0° C. The dropping funnel was charged with tert-butyl hydroxycarbamate (5.01 g, 37.6 mmol) in methanol (30 mL). The contents of the funnel were added dropwise and stirring continued for 3 hours. The reaction was diluted with methylene chloride and transferred to a separatory funnel. The methylene chloride solution was washed sequentially with water and brine. The organic phase was then dried over magnesium sulfate. Filtration and evaporation provided the crude product. The material was purified on a 330 g ISCO silica gel column (0-70% ethyl acetate in hexanes). Evaporation of the product-containing fractions gave 23A (5.44 g, 64% yield) as a pale yellow solid. $^1$H NMR (400 MHz, DMSO-d$_6$) δ ppm 6.40 (ddd, 1H, J=9.2, 6.9, 0.8 Hz), 6.18 (ddd, 1H, J=9.1, 6.1, 1.1 Hz); 4.60-4.73 (m, 2H); 1.53-1.87 (m, 4H); 1.46 (dtt, 1H, J=14.1, 4.9, 4.9, 2.4, 2.4 Hz); 1.39 (s, 9H); 1.24 (qd, 1H, J=12.9, 6.0 Hz).

23B: (+/−)-tert-Butyl cis-4-hydroxycycloheptylcarbamate

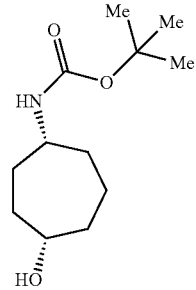

A Parr bottle was charged with Raney Nickel (ca. 1 g). The catalyst was washed with ethanol and suspended in ethanol (30 mL). The starting material, 23A (1.0 g, 4.44 mmol) was added and the reaction pressurized with hydrogen. After hours, TLC analysis suggests good conversion to desired product. The reaction was flushed with nitrogen and filtered through a pad of magnesium sulfate. The filter cake was rinsed well with ethanol. The ethanol solution was evaporated. The isolated material was dissolved in tetrahydrofuran to give a cloudy solution. The liquid was passed through a PTFE filter and then evaporated. The crude product was crystallized from ether-hexanes. The crystalline material was filtered off and rinsed with hexanes. Residual solvent was removed under vacuum to give 23B (780 mg, 3.40 mmol, 77% yield) as a colorless solid. $^1$H NMR (400 MHz, DMSO-d$_6$) δ ppm 6.76 (d, 1H, J=7.6 Hz); 4.36 (d, 1H, J=4.0 Hz); 3.51-3.73 (m, 1H); 3.37 (br. s, 1H); 1.69-1.91 (m, 2H); 1.45-1.66 (m, 5H); 1.37 (s, 9H); 1.06-1.34 (m, 3H).

23C: (+/−)—Cis-4-aminocycloheptanol

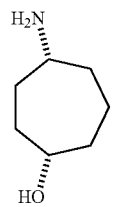

A sample of 23B (0.070 g, 0.31 mmol) was dissolved in 2 mL of 4M HCl in dioxane and stirred 1.5 h. The reaction was concentrated under reduced pressure to afford 23C.HCl (51 mg, quantitative yield) as a white solid. This material was used without characterization in the subsequent step.

23: (+/−)-4-Amino-N-(cis-4-hydroxycyclohepyl)-7-(2-methoxy-4-pyridinyl)pyrrolo[2,1-f][1,2,4]triazine-5-carboxamide

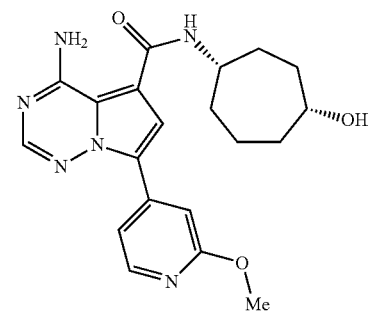

23 was prepared from 6A (15 mg, 0.053 mmol) and 23C (13 mg, 0.079 mmol) by the general methods shown for 2D. 23 (21 mg, 53% yield) was obtained as off-white solid. HPLC: 12.57 min (Sunfire C18 4.6×150 mm 3.5 micron. 1.0 mL/min, 10-90% methanol-water gradient over 10 min., 0.05% TFA). MS (ES): m/z=397 [M+H]+. 1H NMR (400 MHz, DMSO-d6) δ ppm 10.24 (br. s, 1H); 8.15 (d, 1H, J=8.0 Hz); 7.99-8.12 (m, 2H); 7.84 (s, 1H); 7.83 (s, 1H); 7.35-7.43 (m, 2H); 4.27 (d, 1H, J=3.3 Hz); 3.73-3.83 (m, 1H); 3.67 (s, 3H); 3.46-3.56 (m, 1H); 0.98-1.73 (m, 10H).

By generally following the procedures described above, the following compounds of the invention were prepared:

TABLE 2

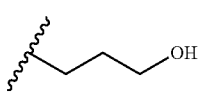 [SMILES: *CCCO]

| Ex. No. | Name | R1 | [M + H]+ | HPLC Tr |
|---|---|---|---|---|
| 24 | 4-amino-7-(4-pyridinyl)pyrrolo[2,1-f][1,2,4]triazine-5-carboxamide | H | 254.9 | 5.59a |
| 25 | 4-amino-N-(3-hydroxypropyl)-7-(4-pyridinyl)pyrrolo[2,1-f][1,2,4]triazine-5-carboxamide | 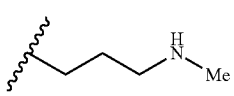 | 312.9 | 7.27a |
| 26 | 4-amino-N-(3-(methylamino)propyl)-7-(4-pyridinyl)pyrrolo[2,1-f][1,2,4]triazine-5-carboxamide | 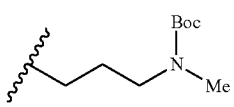 [SMILES: *CCCN(C)C(=O)OC(C)(C)C] | 326.0 | 0.95d |
| 27 | tert-butyl (3-(((4-amino-7-(4-pyridinyl)pyrrolo[2,1-f][1,2,4]triazin-5-yl)carbonyl)amino)propyl)methylcarbamate | 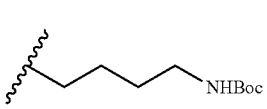 [SMILES: *CCCCNC(=O)OC(C)(C)C] | 426.0 | 4.39b |
| 28 | tert-buyl (4-(((4-amino-7-(4-pyridinyl)pyrrolo[2,1-f][1,2,4]triazin-5-yl)carbonyl)amino)butyl)carbamate | 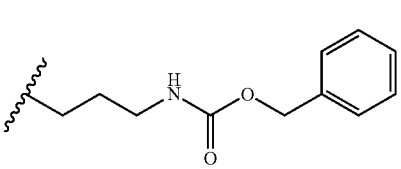 [SMILES: *CCCNC(=O)OCc1ccccc1] | 426.0 | 5.42b |
| 29 | benzyl (3-(((4-amino-7-(4-pyridinyl)pyrrolo[2,1-f][1,2,4]triazin-5-yl)carbonyl)amino)propyl)carbamate | 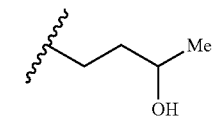 [SMILES: *CCC(C)O] | 446.0 | 5.18b |
| 30 | 4-amino-N-(3-hydroxybutyl)-7-(4-pyridinyl)pyrrolo[2,1-f][1,2,4]triazine-5-carboxamide | 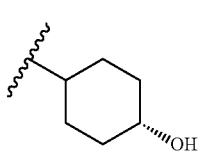 | 326.9 | 8.27a |
| 31 | 4-amino-N-(trans-4-hydroxycyclohexyl)-7-(4-pyridinyl)pyrrolo[2,1-f][1,2,4]triazine-5-carboxamide |  | 353.0 | 8.22a |
| 32 | 4-amino-N-trans-(4-aminocyclohexyl)-7-(4-pyridinyl)pyrrolo[2,1-f][1,2,4]triazine-5-carboxamide |  | 352.1 | 2.06b |
| 33 | 4-amino-N-(3-hydroxy-2,2-dimethylpropyl)-7-(4-pyridinyl)pyrrolo[2,1-f][1,2,4]triazine-5-carboxamide | | 341.1 | 9.00a |

TABLE 2-continued

| Ex. No. | Name | R₁ | [M + H]⁺ | HPLC Tr |
|---|---|---|---|---|
| 34 | 4-amino-N-(cis-4-hydroxycycloheptyl)-7-(4-pyridinyl)pyrrolo[2,1-f][1,2,4]triazine-5-carboxamide | | 367.1 | 9.40[a] |
| 35 | 4-amino-N-trans(4-((isopropylcarbamoyl)amino)cyclohexyl)-7-(4-pyridinyl)pyrrolo[2,1-f][1,2,4]triazine-5-carboxamide | | 437.1 | 9.84[a] |
| 36 | N-trans-(4-acetamidocyclohexyl)-4-amino-7-(4-pyridinyl)pyrrolo[2,1-f][1,2,4]triazine-5-carboxamide | | 394.1 | |
| 37 | tert-butyl (trans-4-(((4-amino-7-(4-pyridinyl)pyrrolo[2,1-f][1,2,4]triazin-5-yl)carbonyl)amino)cyclohexyl)carbamate | | 452.1 | 3.18[b] |
| 38 | ethyl (trans-4-(((4-amino-7-(4-pyridinyl)pyrrolo[2,1-f][1,2,4]triazin-5-yl)carbonyl)amino)cyclohexyl)carbamate | | 424.1 | 10.1[a] |
| 39 | 4-amino-N-trans-(4-((butylcarbamoyl)amino)cyclohexyl)-7-(4-pyridinyl)pyrrolo[2,1-f][1,2,4]triazine-5-carboxamide | | 451.2 | 10.6[a] |
| 40 | 4-amino-N-(4-oxocyclohexyl)-7-(4-pyridinyl)pyrrolo[2,1-f][1,2,4]triazine-5-carboxamide | | 351.0 | 8.30[a] |
| 41 | 4-amino-N-(cis-3-(hydroxymethyl)cyclobutyl)-7-(4-pyridinyl)pyrrolo[2,1-f][1,2,4]triazine-5-carboxamide | | 339.1 | 8.32[a] |
| 42 | 4-amino-N-(cis-4-hydroxycyclohexyl)-7-(4-pyridinyl)pyrrolo[2,1-f][1,2,4]triazine-5-carboxamide | | 353.0 | 8.64[a] |

TABLE 2-continued

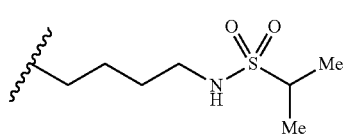 [SMILES: *CCCCNS(=O)(=O)C(C)C]

| Ex. No. | Name | R₁ | [M + H]⁺ | HPLC Tr |
|---|---|---|---|---|
| 43 | 4-amino-N-(4-((isopropylsulfonyl)amino)butyl)-7-(4-pyridinyl)pyrrolo[2,1-f][1,2,4]triazine-5-carboxamide | 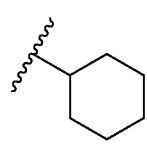 [SMILES: *C1CCCCC1] | 432.1 | |
| 44 | 4-amino-N-cyclohexyl-7-(4-pyridinyl)pyrrolo[2,1-f][1,2,4]triazine-5-carboxamide | 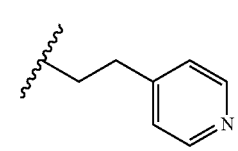 [SMILES: *CCc1ccncc1] | 337.1 | 5.29[b] |
| 45 | 4-amino-7-(4-pyridinyl)-N-(2-(4-pyridinyl)ethyl)pyrrolo[2,1-f][1,2,4]triazine-5-carboxamide | 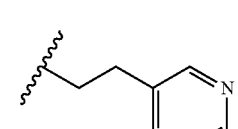 | 360.1 | 5.95[a] |
| 46 | 4-amino-7-(4-pyridinyl)-N-(2-(3-pyridinyl)ethyl)pyrrolo[2,1-f][1,2,4]triazine-5-carboxamide | 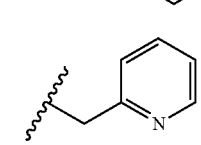 | 360.2 | 2.33[b] |
| 47 | 4-amino-7-(4-pyridinyl)-N-(2-pyridinylmethyl)pyrrolo[2,1-f][1,2,4]triazine-5-carboxamide | 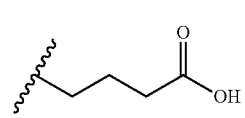 | 346.2 | 1.62[b] |
| 48 | 4-(((4-amino-7-(4-pyridinyl)pyrrolo[2,1-f][1,2,4]triazin-5-yl)carbonyl)amino)butanoic acid | 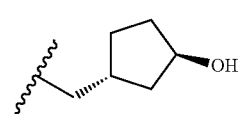 [SMILES: *C[C@@H]1CC[C@@H](O)C1] | 341.1 | 2.89[b] |
| 49 | 4-amino-N-(((1R,3R)-3-hydroxycyclopentyl)methyl)-7-(4-pyridinyl)pyrrolo[2,1-f][1,2,4]triazine-5-carboxamide | 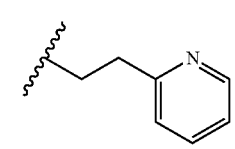 [SMILES: *CCc1ccccn1] | 353.1 | 8.49[a] |
| 50 | 4-amino-7-(4-pyridinyl)-N-(2-(2-pyidinyl)ethyl)pyrrolo[2,1-f][1,2,4]triazine-5-carboxamide | 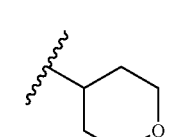 | 360.2 | 7.33[a] |
| 51 | 4-amino-7-(4-pyridinyl)-N-(tetrahydro-2H-pyran-4-yl)pyrrolo[2,1-f][1,2,4]triazine-5-carboxamide |  | 339.0 | 3.82[f] |

TABLE 2-continued

| Ex. No. | Name | R₁ | [M + H]⁺ | HPLC Tr |
|---|---|---|---|---|
| 52 | 4-amino-N-(trans-4-(2-methoxyethoxy)cyclohexyl)-7-(4-pyridinyl)pyrrolo[2,1-f][1,2,4]triazine-5-carboxamide | | 411.1 | 4.37[f] |
| 53 | 4-amino-N-(trans-4-((2-methylalanyl)amino)cyclohexyl)-7-(4-pyridinyl)pyrrolo[2,1-f][1,2,4]triazine-5-carboxamide | | 437.4 | 2.76[f] |
| 54 | 4-amino-N-(trans-4-(4-(2-methoxyethyl)-4H-1,2,4-triazol-3-yl)cyclohexyl)-7-(4-pyridinyl)pyrrolo[2,1-f][1,2,4]triazine-5-carboxamide | | 462.3 | 3.18[f] |
| 55 | 4-amino-7-(4-pyridinyl)-N-(trans-4-(tetrahydro-2H-pyran-4-yloxy)cyclohexyl)pyrrolo[2,1-f][1,2,4]triazine-5-carboxamide | | 437.2 | 4.22[f] |
| 56 | 4-amino-N-(trans-4-(cyclobutyloxy)cyclohexyl)-7-(4-pyridinyl)pyrrolo[2,1-f][1,2,4]triazine-5-carboxamide | | 407.2 | 5.24[f] |
| 57 | 4-amino-N-(trans-4-(1-hydroxy-1-methylethyl)cyclohexyl)-7-(4-pyridinyl)pyrrolo[2,1-f][1,2,4]triazine-5-carboxamide | | 395.2 | 4.21[f] |

[a]Waters Sunfire C18 4.6 × 150 mm 3.5 micron. 1 mL/min, 10-90% methanol-water 0.2% H₃PO₄, gradient over 10 min.
[b]YMC S5 ODS, 4.6 × 50 mm. 4 mL/min, 10-90% methanol-water 0.2% H₃PO₄, gradient over 12 min.
[c]Waters X-Bridge Phenyl 4.6 × 150 mm 3.5 micron, 1 mL/min, 10-90% methanol-water 0.2% H₃PO₄, gradient over 10 min.
[d]YMC S5 ODS, 4.6 × 50 mm. 4 mL/min, 10-90% methanol-water 0.2% H₃PO₄, gradient over 4 min.
[e]YMC S5 ODS, 4.6 × 50 mm. 1 mL/min, 10-90% methanol-water 0.2% H₃PO₄, gradient over 15 min.
[f]Sunfire C18 4.6 × 150 mm 3.5 micron. 0.5 mL/min, 14-95% Acetonitrile-water, 0.05% TFA, gradient over 12 min.
[g]YMC pro c18 S5 ODS, 4.6 × 50 mm. 4 mL/min, 10-90% methanol-water 0.2% H₃PO₄, gradient over 12 min.
[h]SUPELCO ® Ascentis 4.6 × 50 mm, 2.7 micron C18, 4 mL/min, 5-95% acetonitrile-water, 10 mM NH₄OAc, gradient over 4 min.

By generally following the procedures described above, the following compounds of the invention were prepared:

TABLE 3

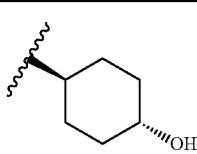

| Ex. No. | Name | $R_1$ | [M + H]$^+$ | HPLC Tr |
|---|---|---|---|---|
| 58 | 4-amino-N-(trans-4-hydroxycyclohexyl)-7-(2-methoxy-4-pyridinyl)pyrrolo[2,1-f][1,2,4]triazine-5-carboxamide | 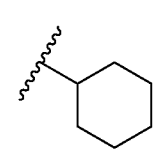 | 383.0 | 3.00[d] |
| 59 | 4-amino-N-cyclohexyl-7-(2-methoxy-4-pyridinyl)pyrrolo[2,1-f][1,2,4]triazine-5-carboxamide | 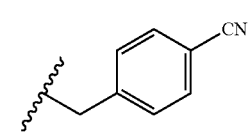 | 367.3 | 14.39[c] |
| 60 | 4-amino-N-(4-cyanobenzyl)-7-(2-methoxy-4-pyridinyl)pyrrolo-[2,1-f][1,2,4]triazine-5-carboxamide | 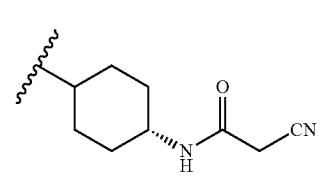 | 400.4 | 12.9[c] |
| 61 | 4-amino-N-(trans-4-((cyanoacetyl)amino)cyclohexyl)-7-(2-methoxy-4-pyridinyl)pyrrolo[2,1-f][1,2,4]triazine-5-carboxamide | | 449.6 | 11.7[e] |
| 62 | 4-amino-7-(2-methoxy-4-pyridinyl)-N-(4-(4-morpholinyl)benzyl)pyrrolo[2,1-f][1,2,4]triazine-5-carboxamide | 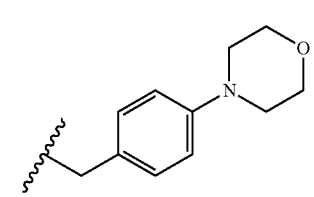 [SMILES: *Cc1ccc(N2CCOCC2)cc1] | 460.6 | 12.1[e] |
| 63 | 4-amino-7-(2-methoxy-4-pyridinyl)-N-(3-(4-morpholinylmethyl)benzyl)pyrrolo[2,1-f][1,2,4]triazine-5-carboxamide | 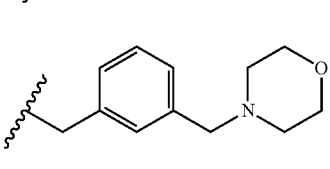 | 474.2 | 12.1[f] |
| 64 | 4-amino-7-(2-methoxy-4-pyridinyl)-N-(trans-4-((trifluoroacetyl)amino)cyclohexyl)pyrrolo[2,1-f][1,2,4]triazine-5-carboxamide | 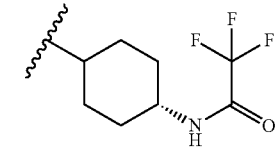 | 478.5 | 13.5[e] |

TABLE 3-continued

| Ex. No. Name | R₁ | [M + H]⁺ | HPLC Tr |
|---|---|---|---|
| 65 tert-butyl (2-((trans-4-(((4-amino-7-(2-methoxy-4-pyridinyl)pyrrolo[2,1-f][1,2,4]triazin-5-yl)carbonyl)amino)cyclohexyl)amino)-1,1-dimethyl-2-oxoethyl)carbamate | | 567.7 | 14.5[e] |
| 66 4-amino-7-(2-methoxy-4-pyridinyl)-N-(trans-4-((2-pyridinylacetyl)amino)cyclohexyl)pyrrolo[2,1-f][1,2,4]triazine-5-carboxamide | | 501.5 | 10.8[e] |
| 67 4-amino-7-(2-methoxy-4-pyridinyl)-N-(trans-4-((1,2,3-thiadiazol-4-ylcarbonyl)amino)cyclohexyl)pyrrolo[2,1-f][1,2,4]triazine-5-carboxamide | | 494.4 | 6.16[f] |
| 68 4-amino-7-(2-methoxy-4-pyridinyl)-N-(trans-4-((2-methylalanyl)amino)cyclohexyl)pyrrolo[2,1-f][1,2,4]triazine-5-carboxamide | | 467.6 | 10.3[e] |
| 69 2-methoxyethyl (trans-4-(((4-amino-7-(2-methoxy-4-pyridinyl)pyrrolo[2,1-f][1,2,4]triazin-5-yl)carbonyl)amino)cyclohexyl)carbamate | | 484.6 | 5.99[f] |
| 70 4-fluorophenyl (trans-4-(((4-amino-7-(2-methoxy-4-pyridinyl)pyrrolo[2,1-f][1,2,4]triazin-5-yl)carbonyl)amino)cyclohexyl)carbamate | | 520.6 | 7.81[f] |
| 71 tert-butyl 4-(((4-amino-7-(2-methoxy-4-pyridinyl)pyrrolo[2,1-f][1,2,4]triazin-5-yl)carbonyl)amino)-1-piperidinecarboxylate | | 468.5 | 7.85[f] |

TABLE 3-continued

| Ex. No. Name | R₁ | [M+H]⁺ | HPLC Tr |
|---|---|---|---|
| 72 4-amino-7-(2-methoxy-4-pyridinyl)-N-4-piperidinylpyrrolo[2,1-f][1,2,4]triazine-5-carboxamide | 4-piperidinyl | 368.4 | 3.79[f] |
| 73 4-amino-7-(2-methoxy-4-pyridinyl)-N-(2-(1-pyrrolidinyl)ethyl)pyrrolo[2,1-f][1,2,4]triazine-5-carboxamide | 2-(1-pyrrolidinyl)ethyl | 382.0 | 1.97[h] |
| 74 4-amino-7-(2-methoxy-4-pyridinyl)-N-(3-(4-morpholinyl)propyl)pyrrolo[2,1-f][1,2,4]triazine-5-carboxamide | 3-(4-morpholinyl)propyl | 412.0 | 1.97[h] |
| 75 4-amino-N-(1-benzyl-4-piperidinyl)-7-(2-methoxy-4-pyridinyl)pyrrolo[2,1-f][1,2,4]triazine-5-carboxamide | 1-benzyl-4-piperidinyl | 458.0 | 2.73[h] |
| 76 4-amino-N-(3-methoxybenzyl)-7-(2-methoxy-4-pyridinyl)pyrrolo[2,1-f][1,2,4]triazine-5-carboxamide | 3-methoxybenzyl | 405.0 | 2.85[h] |
| 77 4-amino-N-(4-methoxybenzyl)-7-(2-methoxy-4-pyridinyl)pyrrolo[2,1-f][1,2,4]triazine-5-carboxamide | 4-methoxybenzyl | 405.0 | 2.84[h] |
| 78 4-amino-N-(2-hydroxy-2-phenylethyl)-7-(2-methoxy-4-pyridinyl)pyrrolo[2,1-f][1,2,4]triazine-5-carboxamide | 2-hydroxy-2-phenylethyl | 405.0 | 2.43[h] |
| 79 4-amino-N-(2-(4-methoxyphenyl)ethyl)-7-(2-methoxy-4-pyridinyl)pyrrolo[2,1-f][1,2,4]triazine-5-carboxamide | 2-(4-methoxyphenyl)ethyl | 419.0 | 2.96[h] |
| 80 4-amino-N-(2-(4-hydroxyphenyl)ethyl)-7-(2-methoxy-4-pyridinyl)pyrrolo[2,1-f][1,2,4]triazine-5-carboxamide | 2-(4-hydroxyphenyl)ethyl | 405.0 | 2.40[h] |

TABLE 3-continued

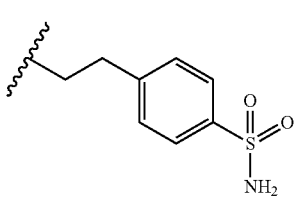 [SMILES: *CCc1ccc(S(N)(=O)=O)cc1]

| Ex. No. Name | R₁ | [M + H]⁺ | HPLC Tr |
|---|---|---|---|
| 81 4-amino-7-(2-methoxy-4-pyridinyl)-N-(2-(4-sulfamoylphenyl)ethyl)pyrrolo[2,1-f][1,2,4]triazine-5-carboxamide | 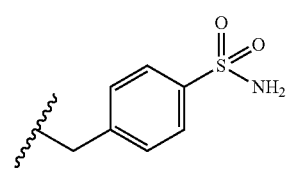 [SMILES: *Cc1ccc(S(N)(=O)=O)cc1] | 467.9 | 2.18[h] |
| 82 4-amino-7-(2-methoxy-4-pyridinyl)-N-(4-sulfamoylbenzyl)pyrrolo[2,1-f][1,2,4]triazine-5-carboxamide | 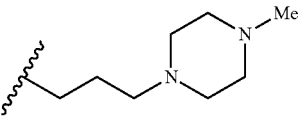 [SMILES: *CCCN1CCN(C)CC1] | 453.9 | 2.15[h] |
| 83 4-amino-7-(2-methoxy-4-pyridinyl)-N-(3-(4-methyl-1-piperazinyl)propyl)pyrrolo[2,1-f][1,2,4]triazine-5-carboxamide | 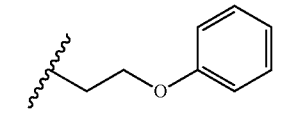 [SMILES: *CCOc1ccccc1] | 425.0 | 1.78[h] |
| 84 4-amino-7-(2-methoxy-4-pyridinyl)-N-(2-phenoxyethyl)pyrrolo[2,1-f][1,2,4]triazine-5-carboxamide | 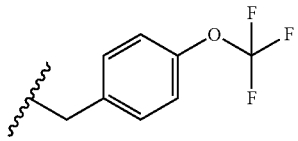 [SMILES: *Cc1ccc(OC(F)(F)F)cc1] | 405.0 | 2.97[h] |
| 85 4-amino-7-(2-methoxy-4-pyridinyl)-N-(4-(trifluoromethoxy)benzyl)pyrrolo[2,1-f][1,2,4]triazine-5-carboxamide | 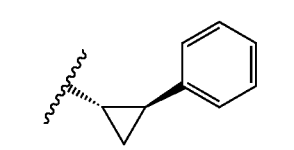 [SMILES: *[C@H]1C[C@@H]1c1ccccc1] | 458.9 | 3.39[h] |
| 86 4-amino-7-(2-methoxy-4-pyridinyl)-N-((1S,2R)-2-phenylcyclopropyl)pyrrolo[2,1-f][1,2,4]triazine-5-carboxamide | 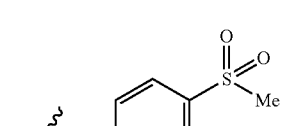 | 401.0 | 3.18[h] |
| 87 4-amino-7-(2-methoxy-4-pyridinyl)-N-(4-(methylsulfonyl)benzyl)pyrrolo[2,1-f][1,2,4]triazine-5-carboxamide | 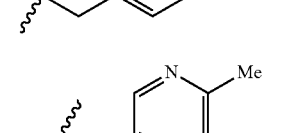 | 452.9 | 2.32[h] |
| 88 4-amino-7-(2-methoxy-4-pyridinyl)-N-((5-methyl-2-pyrazinyl)methyl)pyrrolo[2,1-f][1,2,4]triazine-5-carboxamide | | 391.0 | 2.09[h] |

TABLE 3-continued

| Ex. No. | Name | R₁ | [M + H]⁺ | HPLC Tr |
|---|---|---|---|---|
| 89 | 4-amino-7-(2-methoxy-4-pyridinyl)-N-(1-methyl-4-piperidinyl)pyrrolo[2,1-f][1,2,4]triazine-5-carboxamide | 4-(1-methylpiperidinyl) | 382.0 | 1.67[h] |
| 90 | 4-amino-N-(4-(dimethylamino)cyclohexyl)-7-(2-methoxy-4-pyidinyl)pyrrolo[2,1-f][1,2,4]triazine-5-carboxamide | 4-(dimethylamino)cyclohexyl | 410.0 | 1.76[h] |
| 91 | 4-amino-7-(2-methoxy-4-pyridinyl)-N-(1-(4-pyridinylmethyl)-4-piperidinyl)pyrrolo[2,1-f][1,2,4]triazine-5-carboxamide | 1-(4-pyridinylmethyl)piperidin-4-yl | 458.9 | 2.33[h] |
| 92 | 4-amino-7-(2-methoxy-4-pyridinyl)-N-(1-(2-hydroxyethyl)-4-piperidinyl)pyrrolo[2,1-f][1,2,4]triazine-5-carboxamide | 1-(2-hydroxyethyl)piperidin-4-yl | 412.0 | 1.64[h] |
| 93 | 4-amino-7-(2-methoxy-4-pyridinyl)-N-((3S)-3-piperidinyl)pyrrolo[2,1-f][1,2,4]triazine-5-carboxamide | (3S)-piperidin-3-yl | 368.4 | 3.91[f] |
| 94 | 4-amino-N-(trans-4-((3-hydroxy-3-methylbutanoyl)amino)cyclohexyl)-7-(2-methoxy-4-pyridinyl)pyrrolo[2,1-f][1,2,4]triazine-5-carboxamide | trans-4-((3-hydroxy-3-methylbutanoyl)amino)cyclohexyl | 482.5 | 5.66[f] |
| 95 | N-(trans-4-(beta-alanylamino)cyclohexyl)-4-amino-7-(2-methoxy-4-pyridinyl)pyrrolo[2,1-][1,2,4]triazine-5-carboxamide | trans-4-(beta-alanylamino)cyclohexyl | 453.3 | 4.15[f] |

TABLE 3-continued

| Ex. No. | Name | R₁ | [M + H]⁺ | HPLC Tr |
|---|---|---|---|---|
| 96 | 4-amino-N-(trans-4-(bis(3-azetidinylmethyl)amino)cyclohexyl)-7-(2-methoxy-4-pyridinyl)pyrrolo[2,1-f][1,2,4]triazine-5-carboxamide | | 520.6 | 5.75[e] |
| 97 | 4-amino-N-(trans-4-((3-azetidinylmethyl)amino)cyclohexyl)-7-(2-methoxy-4-pyridinyl)pyrrolo[2,1-f][1,2,4]triazine-3-carboxamide | | 451.6 | 3.64[f] |
| 98 | 4-amino-7-(2-methoxy-4-pyridinyl)-N-((3R)-3-piperidinyl)pyrrolo[2,1-f][1,2,4]triazine-5-carboxamide | | 368.5 | 8.55[f] |
| 99 | 4-amino-7-(2-methoxy-4-pyridinyl)-N-(2-(4-morpholinyl)ethyl)pyrrolo[2,1-f][1,2,4]triazine-5-carboxamide | | 398.0 | 1.97 |
| 100 | 4-amino-N-(trans-4-((3-hydroxypropanoyl)amino)cyclohexyl)-7-(2-methoxy-4-pyridinyl)pyrrolo[2,1-f][1,2,4]triazine-5-carboxamide | | 454.4 | 11.4[e] |
| 101 | 4-amino-N-(trans-4-((3-amino-3-oxopopyl)amino)cyclohexyl)-7-(2-methoxy-4-pyridinyl)pyrrolo[2,1-f][1,2,4]triazine-5-carboxamide | | 453.4 | 3.94[f] |
| 102 | 4-amino-7-(2-methoxy-4-pyridinyl)-N-(trans-4-(D-serylamino)cyclohexyl)pyrrolo[2,1-f][1,2,4]triazine-5-carboxamide | | 469.4 | 4.11[f] |

TABLE 3-continued

| Ex. No. | Name | R₁ | [M + H]⁺ | HPLC Tr |
|---|---|---|---|---|
| 103 | 4-amino-7-(2-methoxy-4-pyridinyl)-N-(trans-4-(L-serylamino)cyclohexyl)pyrrolo[2,1-f][1,2,4]triazine-5-carboxamide | | 469.4 | 4.10ᶠ |
| 104 | 4-amino-7-(2-methoxy-4-pyridinyl)-N-(trans-4-(L-prolylamino)cyclohexyl)pyrrolo[2,1-f][1,2,4]triazine-5-carboxamide | | 479.4 | 4.36ᶠ |
| 105 | 4-amino-7-(2-methoxy-4-pyridinyl)-N-(trans-4-(D-prolylamino)cyclohexyl)pyrrolo[2,1-f][1,2,4]triazine-5-carboxamide | | 479.4 | 4.35ᶠ |
| 106 | 4-amino-N-(trans-4-(((1-aminocyclopropyl)carbonyl)amino)cyclohexyl)-7-(2-methoxy-4-pyridinyl)pyrrolo[2,1-f][1,2,4]triazine-5-carboxamide | | 465.4 | 4.21ᶠ |
| 107 | 4-amino-N-(trans-4-(((1-aminocyclobutyl)carbonyl)amino)cyclohexyl)-7-(2-methoxy-4-pyidinyl)pyrrolo[2,1-f][1,2,4]triazine-5-carboxamide | | 479.4 | 4.36ᶠ |
| 108 | 4-amino-N-(trans-4-(((1-aminocyclopentyl)carbonyl)amino)cyclohexyl)-7-(2-methoxy-4-pyridinyl)pyrrolo[2,1-f][1,2,4]triazine-5-carboxamide | | 493.5 | 4.48ᶠ |

TABLE 3-continued

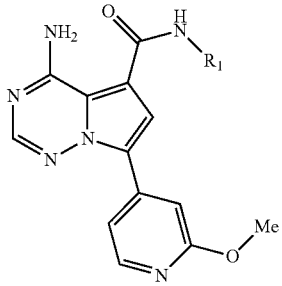

| Ex. No. Name | R₁ | [M+H]⁺ | HPLC Tr |
|---|---|---|---|
| 109 4-amino-N-(trans-4-(((4R)-4-hydroxy-L-prolyl)amino)cyclohexyl)-7-(2-methoxy-4-pyridinyl)pyrrolo[2,1-f]-[1,2,4]triazine-5-carboxamide | 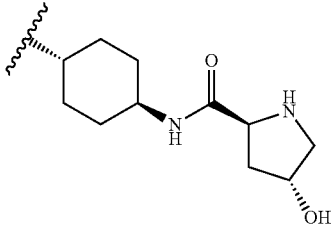 [SMILES: *[C@H]1CC[C@H](NC(=O)[C@@H]2C[C@@H](O)CN2)CC1] | 495.5 | 4.16[f] |
| 110 (+/−)-4-amino-N-(trans-4-(glyceroylamino)cyclohexyl)-7-(2-methoxy-4-pyridinyl)pyrrolo[2,1-f][1,2,4]triazine-5-carboxamide | 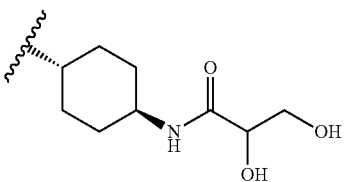 [SMILES: *[C@H]1CC[C@H](NC(=O)C(O)CO)CC1] | 470.3 | 4.71[f] |
| 111 4-amino-N-(trans-4-(((1-(aminomethyl)cyclopropyl)carbonyl)amino)cyclohexyl)-7-(2-methoxy-4-pyridinyl)pyrrolo[2,1-f][1,2,4]triazine-5-carboxamide | 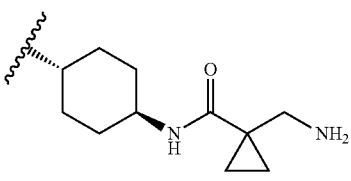 [SMILES: *[C@H]1CC[C@H](NC(=O)C2(CN)CC2)CC1] | 479.5 | 4.32[f] |
| 112 4-amino-N-(trans-4-(((4R)-4-hydroxy-D-prolyl)amino)cyclohexyl)-7-(2-methoxy-4-pyridinyl)pyrrolo[2,1-f]-[1,2,4]triazine-5-carboxamide | 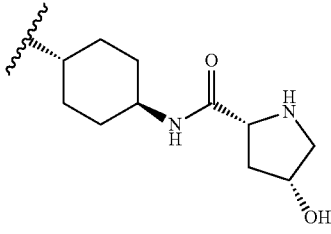 [SMILES: *[C@H]1CC[C@H](NC(=O)[C@H]2C[C@@H](O)CN2)CC1] | 495.3 | 4.31[f] |
| 113 N-(trans-4-(L-alanylamino)cyclohexyl)-4-amino-7-(2-methoxy-4-pyridinyl)pyrrolo[2,1-f][1,2,4]triazine-5-carboxamide | 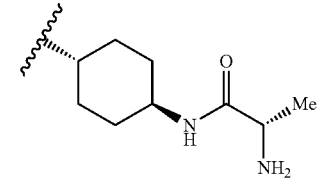 [SMILES: *[C@H]1CC[C@H](NC(=O)[C@H](C)N)CC1] | 453.5 | 4.17[f] |
| 114 N-(trans-4-(D-alanylamino)cyclohexyl)-4-amino-7-(2-methoxy-4-pyridinyl)pyrrolo[2,1-f][1,2,4]triazine-5-carboxamide | 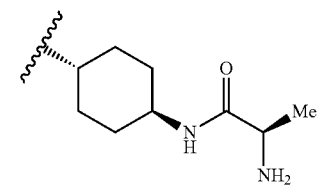 [SMILES: *[C@H]1CC[C@H](NC(=O)[C@@H](C)N)CC1] | 453.5 | 4.17[f] |

TABLE 3-continued

| Ex. No. | Name | R₁ | [M + H]⁺ | HPLC Tr |
|---|---|---|---|---|
| 115 | 4-amino-N-(trans-4-((3-hydroxy-2,2-dimethylpropanoyl)amino)cyclohexyl)-7-(2-methoxy-4-pyridinyl)pyrrolo[2,1-f][1,2,4]triazine-5-carboxamide | | 482.3 | 5.54$^f$ |
| 116 | 4-amino-N-(trans-4-(((4S)-4-hydroxy-L-propyl)amino)cyclohexyl)-7-(2-methoxy-4-pyridinyl)pyrrolo[2,1-f][1,2,4]triazine-5-carboxamide | | 495.3 | 4.32$^f$ |
| 117 | 4-amino-7-(2-methoxy-4-pyridinyl)-N-((3R)-1-(2-methylalanyl)-3-piperidinyl)pyrrolo[2,1-f][1,2,4]triazine-5-carboxamide | | 453.3 | 4.32$^f$ |
| 118 | 4-amino-N-((3R)-1-((1-aminocyclopropyl)carbonyl)-3-piperidinyl)-7-(2-methoxy-4-pyridinyl)pyrrolo[2,1-f][1,2,4]triazine-5-carboxamide | | 451.3 | 4.29$^f$ |
| 119 | 4-amino-N-(trans-4-((2-hydroxy-2-methylpropanoyl)amino)cyclohexyl)-7-(2-methoxy-4-pyridinyl)pyrrolo[2,1-f][1,2,4]triazine-5-carboxamide | | 468.4 | 5.21$^f$ |
| 120 | 4-amino-N-(trans-4-(((1-hydroxycyclopropyl)carbonyl)amino)cyclohexyl)-7-(2-methoxy-4-pyridinyl)pyrrolo[2,1-f][1,2,4]triazine-5-carboxamide | | 466.3 | 5.20$^f$ |
| 121 | 4-amino-7-(2-methoxy-4-pyridinyl)-N-(tetrahydro-2H-pyran-4-yl)pyrrolo[2,1-f][1,2,4]triazine-5-carboxamide | | 369.3 | 5.47$^f$ |

TABLE 3-continued

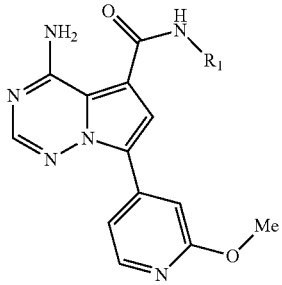

| Ex. No. | Name | R₁ | [M + H]⁺ | HPLC Tr |
|---|---|---|---|---|
| 122 | 4-amino-7-(2-methoxy-4-pyridinyl)-N-(2-(3-methyl-2-oxo-2,3-dihydro-1H-imidazol-1-yl)ethyl)pyrrolo[2,1-f][1,2,4]triazine-5-carboxamide | 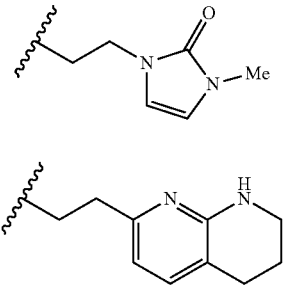 | 409.4 | 10.8ᶜ |
| 123 | 4-amino-7-(2-methoxy-4-pyridinyl)-N-(2-(1,5,6,7-tetrahydro-1,8-naphthyridin-2-yl)ethyl)pyrrolo[2,1-f][1,2,4]triazine-5-carboxamide | 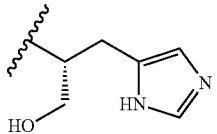 [SMILES: *[C@@H](CO)Cc1cnc[nH]1] | 445.4 | 4.42ᵍ |
| 124 | 4-amino-N-((1R)-2-hydroxy-1-(1H-imidazol-4-ylmethyl)ethyl)-7-(2-methoxy-4-pyridinyl)pyrrolo[2,1-f][1,2,4]triazine-5-carboxamide | 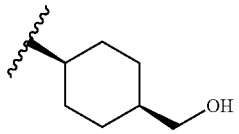 [SMILES: *[C@H]1CC[C@@H](CO)CC1] | 409.3 | 6.71ᶜ |
| 125 | 4-amino-N-(cis-4-(hydroxymethyl)cyclohexyl)-7-(2-methoxy-4-pyridinyl)pyrrolo[2,1-f][1,2,4]triazine-5-carboxamide | 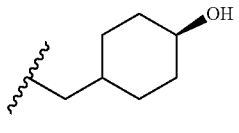 | 397.3 | 5.57 |
| 126 | 4-amino-N-((trans-4-hydroxycyclohexyl)methyl)-7-(2-methoxy-4-pyridinyl)pyrrolo[2,1-f][1,2,4]triazine-5-carboxamide |  | 397.3 | 5.26 |
| 127 | 4-amino-N-(trans-4-((3-bromo-2,2-dimethylpropanoyl)amino)cyclohexyl)-7-(2-methoxy-4-pyridinyl)pyrrolo[2,1-f][1,2,4]triazine-5-carboxamide | 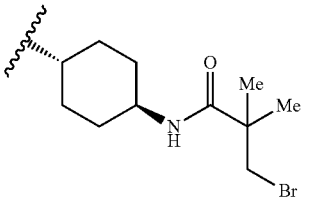 [SMILES: *[C@H]1CC[C@H](NC(=O)C(C)(C)CBr)CC1] | 546.2 | 7.19 |
| 128 | methyl trans-4-(((4-amino-7-(2-methoxy-4-pyridinyl)pyrrolo[2,1-f][1,2,4]triazin-5-yl)carbonyl)amino)cyclohexanecarboxylate | 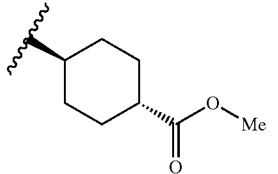 [SMILES: *[C@H]1CC[C@H](C(=O)OC)CC1] | 425.3 | 6.53ᵍ |

TABLE 3-continued

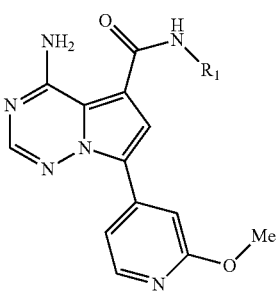

| Ex. No. Name | R₁ | [M + H]⁺ | HPLC Tr |
|---|---|---|---|
| 129 trans-4-(((4-amino-7-(2-methoxy-4-pyridinyl)pyrrolo[2,1-f][1,2,4]triazin-5-yl)carbonyl)amino)cyclohexanecarboxylic acid | 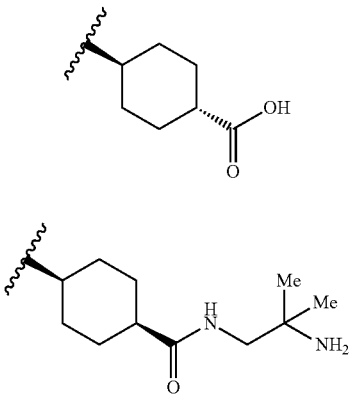 | 411.2 | 5.51[g] |
| 130 4-amino-N-(cis-4-((2-amino-2-methylpropyl)carbamoyl)cyclohexyl)-7-(2-methoxy-4-pyridinyl)pyrrolo[2,1-f][1,2,4]triazine-5-carboxamide | 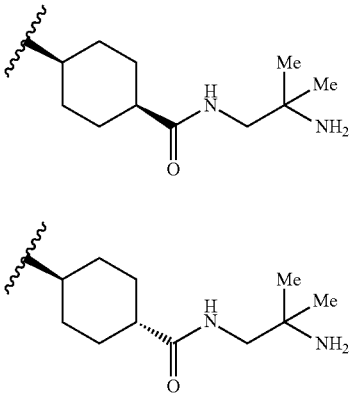 | 481.3 | 4.44[b] |
| 131 4-amino-N-(trans-4-((2-amino-2-methylpropyl)carbamoyl)cyclohexyl)-7-(2-methoxy-4-pyridinyl)pyrrolo[2,1-f][1,2,4]triazine-5-carboxamide | 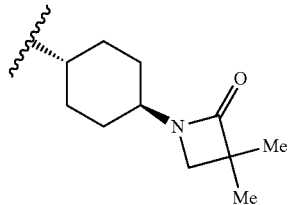 [SMILES: *[C@H]1CC[C@H](N2CC(C)(C)C2=O)CC1] | 481.3 | 8.87[c] |
| 132 4-amino-N-(trans-4-(3,3-dimethyl-2-oxo-1-azetidinyl)cyclohexyl)-7-(2-methoxy-4-pyridinyl)pyrrolo[2,1-f][1,2,4]triazine-5-carboxamide | 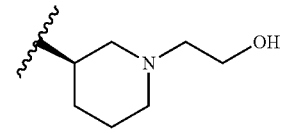 [SMILES: *[C@@H]1CCCN(CCO)C1] | 464.3 | 11.6[b] |
| 133 4-amino-N-((3R)-1-(2-hydroxyethyl)-3-piperidinyl)-7-(2-methoxy-4-pyridinyl)pyrrolo[2,1-f][1,2,4]triazine-5-carboxamide | 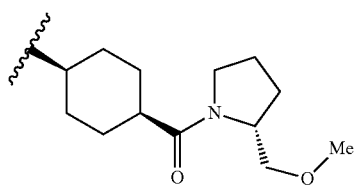 [SMILES: *[C@H]1CC[C@@H](C(=O)N2CCC[C@@H]2COC)CC1] | 412.3 | 3.83[f] |
| 134 4-amino-N-(cis-4-(((2R)-2-(methoxymethyl)-1-pyrrolidinyl)carbonyl)cyclohexyl)-7-(2-methoxy-4-pyridinyl)pyrrolo[2,1-f][1,2,4]triazine-5-carboxamide | | 508.4 | 12.0[c] |

TABLE 3-continued

| Ex. No. Name | R₁ | [M + H]⁺ | HPLC Tr |
|---|---|---|---|
| 135 4-amino-N-(cis-4-((1-(hydroxymethyl)cyclopentyl)carbamoyl)cyclohexyl)-7-(2-methoxy-4-pyridinyl)pyrrolo[2,1-f][1,2,4]triazine-5-carboxamide | cyclohexyl-C(O)NH-cyclopentyl-CH₂OH | 508.5 | 11.5$^c$ |
| 136 4-amino-N-(trans-4-((2-hydroxy-1,1-dimethylethyl)carbamoyl)cyclohexyl)-7-(2-methoxy-4-pyridinyl)pyrrolo[2,1-f][1,2,4]triazine-5-carboxamide | cyclohexyl-C(O)NH-C(Me)₂-CH₂OH | 482.4 | 10.5$^c$ |
| 137 4-amino-N-(cis-4-(((2R)-2-(methoxymethyl)-1-pyrrolidinyl)carbamoyl)cyclohexyl)-7-(2-methoxy-4-pyridinyl)pyrrolo[2,1-f][1,2,4]triazine-5-carboxamide | cyclohexyl-C(O)NH-N(pyrrolidinyl-CH₂OMe) | 523.5 | 11.0$^c$ |
| 138 4-amino-7-(2-methoxy-4-pyridinyl)-N-((3S)-tetrahydro-3-furanyl)pyrrolo[2,1-f][1,2,4]triazine-5-carboxamide | (3S)-tetrahydrofuran-3-yl | 355.2 | 5.17$^f$ |
| 139 4-amino-N-((3R)-1-(2-cyanoethyl)-3-piperidinyl)-7-(2-methoxy-4-pyridinyl)pyrrolo[2,1-f][1,2,4]triazine-5-carboxamide | (3R)-1-(CH₂CH₂CN)-piperidin-3-yl | 421.3 | 4.06$^f$ |
| 140 4-amino-N-((3R)-1-(3-amino-3-oxopropyl)-3-piperidinyl)-7-(2-methoxy-4-pyridinyl)pyrrolo[2,1-f][1,2,4]triazine-5-carboxamide | (3R)-1-(CH₂CH₂C(O)NH₂)-piperidin-3-yl | 439.4 | 3.78$^f$ |
| 141 4-amino-N-(trans-4-(((2R)-2-(methoxymethyl)-1-pyrrolidinyl)carbonyl)cyclohexyl)-7-(2-methoxy-4-pyridinyl)pyrrolo[2,1-f][1,2,4]triazine-5-carboxamide | cyclohexyl-C(O)-N(pyrrolidinyl-CH₂OMe) | 508.5 | 7.03$^b$ |

TABLE 3-continued

| Ex. No. | Name | R₁ | [M + H]⁺ | HPLC Tr |
|---|---|---|---|---|
| 142 | 4-amino-N-3-azepanyl-7-(2-methoxy-4-pyridinyl)pyrrolo[2,1-f][1,2,4]triazine-5-carboxamide | | 382.3 | 3.60[b] |
| 143 | 4-amino-7-(2-methoxy-4-pyridinyl)-N-(trans-4-(L-valylamino)cyclohexyl)pyrrolo[2,1-f][1,2,4]triazine-5-carboxamide | | 481.5 | 4.37[f] |
| 144 | 4-amino-7-(2-methoxy-4-pyridinyl)-N-(1-(methylsulfonyl)-4-piperidinyl)pyrrolo[2,1-f][1,2,4]triazine-5-carboxamide | | 446.3 | 5.62[f] |
| 145 | 4-amino-N-(trans-4-((2-hydroxy-2-methylpropyl)carbamoyl)cyclohexyl)-7-(2-methoxy-4-pyridinyl)pyrrolo[2,1-f][1,2,4]triazine-5-carboxamide | | 482.1 | 5.94[b] |
| 146 | (+/−)-4-amino-7-(2-methoxy-4-pyridinyl)-N-(trans-4-(((1-methyl-3-pyrrolidinyl)methyl)carbamoyl)cyclohexyl)pyrrolo[2,1-f][1,2,4]triazine-5-carboxamide | | 507.1 | 7.57[c] |
| 147 | (+/−)-4-amino-N-(trans-4-(((1-ethyl-2-pyrrolidinyl)methyl)carbamoyl)cyclohexyl)-7-(2-methoxy-4-pyridinyl)pyrrolo[2,1-f][1,2,4]triazine-5-carboxamide | | 521.1 | 9.28[c] |

TABLE 3-continued

| Ex. No. | Name | R₁ | [M + H]⁺ | HPLC Tr |
|---|---|---|---|---|
| 148 | 4-amino-7-(2-methoxy-4-pyridinyl)-N-(trans-4-(methyl(2-(methylamino)ethyl)carbamoyl)cyclohexyl)pyrrolo[2,1-f][1,2,4]triazine-5-carboxamide | | 481.1 | 8.81[c] |
| 149 | 4-amino-N-(trans-4-((3-(4-hydroxy-1-piperidinyl)-2,2-dimethylpropanoyl)amino)cyclohexyl)-7-(2-methoxy-4-pyridinyl)pyrrolo[2,1-f][1,2,4]triazine-5-carboxamide | | 565.6 | 4.27[f] |
| 150 | 4-amino-N-(trans-4-((2,2-dimethyl-3-(4-morpholinyl)propanoyl)amino)cyclohexyl)-7-(2-methoxy-4-pyridinyl)pyrrolo[2,1-f][1,2,4]triazine-5-carboxamide | | 551.6 | 4.35[f] |
| 151 | 4-amino-N-(trans-4-((3-(dimethylamino)-2,2-dimethylpropanoyl)amino)cyclohexyl)-7-(2-methoxy-4-pyridinyl)pyrrolo[2,1-f][1,2,4]triazine-5-carboxamide | | 509.1 | 4.23[f] |
| 152 | 4-amino-N-(trans-4-((2,2-dimethyl-3-(1-pyrrolidinyl)propanoyl)amino)cyclohexyl)-7-(2-methoxy-4-pyridinyl)pyrrolo[2,1-f][1,2,4]triazine-5-carboxamide | | 535.2 | 4.38[f] |
| 153 | 4-amino-N-(trans-4-((3-((2-hydroxyethyl)amino)-2,2-dimethylpropanoyl)amino)cyclohexyl)-7-(2-methoxy-4-pyridinyl)pyrrolo[2,1-f][1,2,4]triazine-5-carboxamide | | 525.2 | 4.14[f] |

TABLE 3-continued

| Ex. No. | Name | R₁ | [M + H]⁺ | HPLC Tr |
|---|---|---|---|---|
| 154 | 4-amino-N-(trans-4-((N,2-dimethylalanyl)amino)cyclohexyl)-7-(2-methoxy-4-pyridinyl)pyrrolo[2,1-f][1,2,4]triazine-5-carboxamide | | 481.1 | 4.24ᶠ |
| 155 | 4-amino-N-(trans-4-((3-amino-2,2-dimethylpropanoyl)amino)cyclohexyl)-7-(2-methoxy-4-pyridinyl)pyrrolo[2,1-f][1,2,4]triazine-5-carboxamide | | 481.2 | 4.14ᶠ |
| 156 | 4-amino-N-(trans-4-((3-((2-hydroxyethyl)(methyl)amino)-2,2-dimethylpropanoyl)amino)cyclohexyl)-7-(2-methoxy-4-pyridinyl)pyrrolo[2,1-f][1,2,4]triazine-5-carboxamide | | 539.2 | 4.33ᶠ |
| 157 | 2-(dimethylamino)ethyl (trans-4-(((4-amino-7-(2-methoxy-4-pyridinyl)pyrrolo[2,1-f][1,2,4]triazin-5-yl)carbonyl)amino)cyclohexyl)carbamate | | 497.4 | 4.19ᶠ |
| 158 | 4-amino-N-((3R,4R)-4-ethoxytetrahydro-3-furanyl)-7-(2-methoxy-4-pyridinyl)pyrrolo[2,1-f][1,2,4]triazine-5-carboxamide | | 399.1 | 5.78ᶠ |
| 159 | 4-amino-N-((2R)-2,3-dihydroxypropyl)-7-(2-methoxy-4-pyridinyl)pyrrolo[2,1-f][1,2,4]triazine-5-carboxamide | | 359.0 | 3.84ᶠ |
| 160 | 4-amino-N-((2S)-2,3-dihydroxypropyl)-7-(2-methoxy-4-pyridinyl)pyrrolo[2,1-f][1,2,4]triazine-5-carboxamide | | 359.0 | 3.82ᶠ |

TABLE 3-continued

| Ex. No. | Name | R₁ | [M + H]⁺ | HPLC Tr |
|---|---|---|---|---|
| 161 | 4-amino-N-((1R,2S,4R)-2-(hydroxymethyl)-4-phenylcyclohexyl)-7-(2-methoxy-4-pyridinyl)pyrrolo[2,1-f][1,2,4]triazine-5-carboxamide | | 473.1 | 7.86[f] |
| 162 | 4-amino-N-(trans-4-(cyclobutyloxy)cyclohexyl)-7-(2-methoxy-4-pyridinyl)pyrrolo[2,1-f][1,2,4]triazine-5-carboxamide | | 437.1 | 7.63[f] |
| 163 | 4-amino-7-(2-methoxy-4-pyridinyl)-N-(trans-4-phenylcyclohexyl)pyrrolo[2,1-f][1,2,4]triazine-5-carboxamide | | 443.1 | 9.06[f] |
| 164 | 4-amino-7-(2-methoxy-4-pyridinyl)-N-(cis-4-phenylcyclohexyl)pyrrolo[2,1-f][1,2,4]triazine-5-carboxamide | | 443.2 | 9.19[f] |
| 165 | 4-amino-7-(2-methoxy-4-pyridinyl)-N-(trans-4-(tetrahydro-2H-pyran-4-yloxy)cyclohexyl)pyrrolo[2,1-f][1,2,4]triazine-5-carboxamide | | 467.2 | 6.31[f] |
| 166 | 4-amino-7-(2-methoxy-4-pyridinyl)-N-((3R,4R)-4-(4-methyl-1-piperazinyl)tetrahydro-3-furanyl)pyrrolo[2,1-f][1,2,4]triazine-5-carboxamide | | 453.2 | 3.77[f] |

TABLE 3-continued

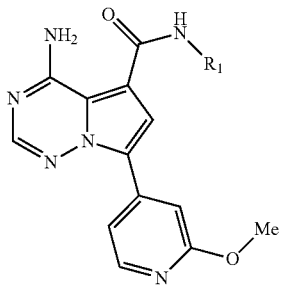

| Ex. No. | Name | R₁ | [M + H]⁺ | HPLC Tr |
|---|---|---|---|---|
| 167 | 4-amino-7-(2-methoxy-4-pyridinyl)-N-(trans-4-(4-morpholinyl)cyclohexyl)pyrrolo[2,1-f][1,2,4]triazine-5-carboxamide | 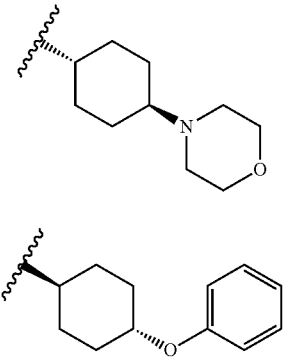 | 452.1 | 4.04[f] |
| 168 | 4-amino-7-(2-methoxy-4-pyridinyl)-N-(trans-4-phenoxycyclohexyl)pyrrolo[2,1-f][1,2,4]triazine-5-carboxamide | 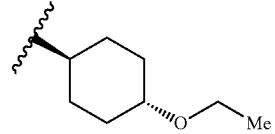 | 459.1 | 8.92[f] |
| 169 | 4-amino-N-(trans-4-ethoxycyclohexyl)-7-(2-methoxy-4-pyridinyl)pyrrolo[2,1-f][1,2,4]triazine-5-carboxamide | 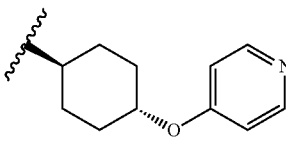 [SMILES: *[C@H]1CC[C@H](Oc2ccccc2)CC1] | 411.1 | 6.76[f] |
| 170 | 4-amino-7-(2-methoxy-4-pyridinyl)-N-(trans-4-(4-pyridinyloxy)cyclohexyl)pyrrolo[2,1-f][1,2,4]triazine-5-carboxamide | 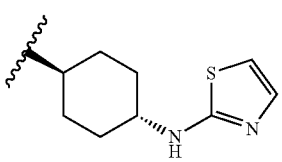 [SMILES: *[C@H]1CC[C@H](Nc2nccs2)CC1] | 460.1 | 4.67[f] |
| 171 | 4-amino-7-(2-methoxy-4-pyridinyl)-N-(trans-4-(1,3-thiazol-2-ylamino)cyclohexyl)pyrrolo[2,1-f][1,2,4]triazine-5-carboxamide | 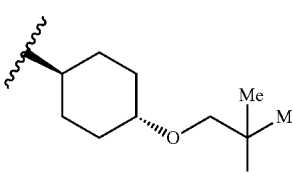 | 465.1 | 4.52[f] |
| 172 | 4-amino-N-(trans-4-(2,2-dimethylpropoxy)cyclohexyl)-7-(2-methoxy-4-pyridinyl)pyrrolo[2,1-f][1,2,4]triazine-5-carboxamide | 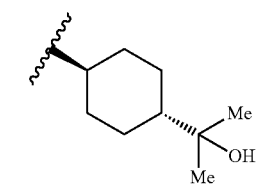 [SMILES: *[C@H]1CC[C@H](C(C)(C)O)CC1] | 453.2 | 9.87[f] |
| 173 | 4-amino-N-(trans-4-(1-hydroxy-1-methylethyl)cyclohexyl)-7-(2-methoxy-4-pyridinyl)pyrrolo[2,1-f][1,2,4]triazine-5-carboxamide | | 425.2 | 6.12[f] |

TABLE 3-continued

| Ex. No. | Name | R₁ | [M + H]⁺ | HPLC Tr |
|---|---|---|---|---|
| 174 | 4-amino-N-(trans-4-((2,6-dimethyltetrahydro-2H-pyran-4-yl)oxy)cyclohexyl)-7-(2-methoxy-4-pyidinyl)pyrrolo[2,1-f][1,2,4]triazine-5-carboxamide | (cyclohexyl-O-2,6-dimethyltetrahydropyran) | 495.3 | 7.70ᶠ |
| 175 | 4-amino-N-(trans-4-(2-methoxyethoxy)cyclohexyl)-7-(2-methoxy-4-pyridinyl)pyrrolo[2,1-f][1,2,4]triazine-5-carboxamide | (cyclohexyl-O-CH₂CH₂-OMe) | 441.2 | 6.05ᶠ |
| 176 | 4-amino-N-((1R,2S,3R,4R)-2,3-dihydroxy-4-(hydroxymethyl)cyclopentyl)-7-(2-methoxy-4-pyridinyl)pyrrolo[2,1-f][1,2,4]triazine-5-carboxamide | (cyclopentyl with 2,3-diOH and CH₂OH) | 415.1 | 3.82ᶠ |
| 177 | 4-amino-7-(2-methoxy-4-pyridinyl)-N-(trans-4-(tetrahydro-3-furanyloxy)cyclohexyl)pyrrolo[2,1-f][1,2,4]triazine-5-carboxamide | (cyclohexyl-O-tetrahydrofuran-3-yl) | 453.1 | 6.09ᶠ |
| 178 | 4-amino-N-(trans-4-((2,2-dimethyltetrahydro-2H-pyran-4-yl)oxy)cyclohexyl)-7-(2-methoxy-4-pyridinyl)pyrrolo[2,1-f][1,2,4]triazine-2-carboxamide | (cyclohexyl-O-2,2-dimethyltetrahydropyran-4-yl) | 495.2 | 7.10ᶠ |
| 179 | 4-amino-7-(2-methoxy-4-pyridinyl)pyrrolo[2,1-f][1,2,4]triazine-5-carboxamide | H | 285.2 | 4.41ᶠ |
| 180 | 4-amino-7-(2-methoxy-4-pyridinyl)-N-(trans-4-(2-(1-pyrrolidinyl)ethoxy)cyclohexyl)pyrrolo[2,1-f][1,2,4]triazine-5-carboxamide | (cyclohexyl-O-CH₂CH₂-pyrrolidinyl) | 480.2 | 4.73ᶠ |
| 181 | 4-amino-7-(2-methoxy-4-pyridinyl)-N-(trans-4-(2-(4-morpholinyl)ethoxy)cyclohexyl)pyrrolo[2,1-f][1,2,4]triazine-5-carboxamide | (cyclohexyl-O-CH₂CH₂-morpholinyl) | 496.2 | 4.65ᶠ |

By generally following the procedures described above, the following compounds of the invention were prepared:

TABLE 4

| Ex. No. | Name | R | R' | [M + H]⁺ | HPLC Tr |
|---|---|---|---|---|---|
| 182 | tert-butyl ((1-((4-amino-7-(4-pyridinyl)pyrrolo[2,1-f][1,2,4]triazin-5-yl)carbonyl)-3-azetidinyl)methyl)carbamate | azetidine with CH₂NHC(O)OC(Me)₃ | H | 424.0 | 8.75[c] |
| 183 | (1-((4-amino-7-(4-pyridinyl)pyrrolo[2,1-f][1,2,4]triazin-5-yl)carbonyl)-3-azetidinyl)methanol | azetidine-CH₂OH | H | 325.0 | 8.06[c] |
| 184 | (+/−)-(1-((4-amino-7-(4-pyridinyl)pyrrolo[2,1-f][1,2,4]triazin-5-yl)carbonyl)-4-piperidinyl)methanol | piperidine-CH₂OH | H | 352.0 | 2.61[b] |
| 185 | 4-amino-N-cyclohexyl-7-(2-methoxy-4-pyridinyl)-N-methylpyrrolo[2,1-f][1,2,4]triazine-5-carboxamide | N(Me)(cyclohexyl) | OMe | 381.5 | 8.07[f] |
| 186 | (+/−)-5-((3-amino-1-azepanyl)carbonyl)-7-(2-methoxy-4-pyridinyl)pyrrolo[2,1-f][1,2,4]triazin-4-amine | piperidine-CH₂OH | OMe | 382.1 | 2.85[b] |
| 187 | (+/−)-tert-butyl ((1-((4-amino-7-(4-pyridinyl)pyrrolo[2,1-f][1,2,4]triazin-5-yl)carbonyl)-3-pyrrolidinyl)methyl)carbamate | pyrrolidine with CH₂NHC(O)OC(Me)₃ | H | 438.1 | 9.96[a] |
| 188 | 1-((4-amino-7-(2-methoxy-4-pyridinyl)pyrrolo[2,1-f][1,2,4]triazin-5-yl)carbonyl)-4-piperidinol | piperidine-OH | OMe | 369.1 | 4.26[f] |
| 189 | (+/−)-5-((3-(aminomethyl)-1-piperidinyl)carbonyl)-7-(4-pyridinyl)pyrrolo[2,1-f][1,2,4]triazin-4-amine | piperidine-CH₂NH₂ | H | 352.2 | 2.31[a] |

TABLE 4-continued

| Ex. No. Name | R | R' | [M + H]+ | HPLC Tr |
|---|---|---|---|---|
| 190 tert-butyl ((1-((4-amino-7-(4-pyridinyl)pyrrolo[2,1-f][1,2,4]triazin-5-yl)carbonyl)-4-piperidinyl)methyl)-carbamate | piperidine-CH2-NHC(O)O-tBu | H | 452.0 | 5.07[b] |
| 191 4-amino-N-(3-aminopropyl)-N-methyl-7-(4-pyridinyl)pyrrolo[2,1-f][1,2,4]triazine-5-carboxamide | N(Me)CH2CH2CH2NH2 | H | 326 | 0.52[b] |
| 192 (+/−)-tert-butyl ((1-((4-amino-7-(4-pyridinyl)pyrrolo[2,1-f][1,2,4]triazin-5-yl)carbonyl)-3-piperidinyl)methyl)-carbamate | 3-piperidinyl-CH2-NHC(O)O-tBu | H | 452.3 | 4.92[b] |

By generally following the procedures described above, the following compounds of the invention were prepared:

TABLE 5

| Ex. No. Name | R1 | R3 | [M + H]+ | HPLC Tr |
|---|---|---|---|---|
| 193 4-amino-N-(trans-4-hydroxycyclohexyl)-7-(4-hydroxy-3-methoxyphenyl)pyrrolo-[2,1-f][1,2,4]triazine-5-carboxamide | trans-4-hydroxycyclohexyl | 4-hydroxy-3-methoxyphenyl | 398.6 | 10.27[e] |

TABLE 5-continued

| Ex. No. | Name | R₁ | R₃ | [M + H]⁺ | HPLC Tr |
|---|---|---|---|---|---|
| 194 | 4-(4-amino-5-((trans-4-hydroxycyclohexyl)carbamoyl)pyrrolo-[2,1-f][1,2,4]triazin-7-yl)-2-methoxybenzoic acid | trans-4-hydroxycyclohexyl | 4-carboxy-2-methoxyphenyl | 426.4 | 9.23[e] |
| 195 | 4-amino-N-(trans-4-hydroxycyclohexyl)-7-(3-methoxyphenyl)pyrrolo[2,1-f][1,2,4]-triazine-5-carboxamide | trans-4-hydroxycyclohexyl | 3-methoxyphenyl | 382.5 | 11.83[e] |
| 196 | 4-amino-7-(4-carbamoyl-3-methoxyphenyl)-N-(trans-4-hydroxycyclohexyl)pyrrolo[2,1-f]-[1,2,4]triazine-5-carboxamide | trans-4-hydroxycyclohexyl | 4-carbamoyl-2-methoxyphenyl | 425.3 | 8.75[e] |
| 197 | 4-amino-7-(3-carbamoylphenyl)-N-(trans-4-hydroxycyclohexyl)-pyrrolo[2,1-f][1,2,4]triazine-5-carboxamide | trans-4-hydroxycyclohexyl | 3-carbamoylphenyl | 395.6 | 9.63[e] |
| 198 | 4-amino-7-(2-methoxypyridin-4-yl)pyrrolo[2,1-f][1,2,4]triazine-5-carbohydrazide | NH₂ | 2-methoxypyridin-4-yl | 300 | |
| 199 | 4-amino-N-trans-(4-aminocyclohexyl)-7-(2-isopropoxypyridin-4-yl)pyrrolo-[2,1-f][1,2,4]triazine-5-carboxamide | trans-4-aminocyclohexyl | 2-isopropoxypyridin-4-yl | 410 | 4.42[f] |
| 200 | 4-amino-N-trans-(4-aminocyclohexyl)-7-(2-(2-hydroxyethyl)pyridin-4-yl)-pyrrolo[2,1-f][1,2,4]triazine-5-carboxamide | trans-4-aminocyclohexyl | 2-(2-hydroxyethoxy)pyridin-4-yl | 412 | 3.20[f] |
| 201 | 4-amino-N-trans-(4-aminocyclohexyl)-7-(2-ethoxypyridin-4-yl)pyrrolo[2,1-f]-[1,2,4]triazine-5-carboxamide | trans-4-aminocyclohexyl | 2-ethoxypyridin-4-yl | 396 | 4.05[f] |

TABLE 5-continued

| Ex. No. | Name | R₁ | R₃ | [M + H]⁺ | HPLC Tr |
|---|---|---|---|---|---|
| 202 | ethyl (trans-4-(((4-amino-7-(2-ethoxypyridin-4-yl)pyrrolo[2,1-f]-[1,2,4]triazin-5-yl)carbonyl)amino)-cyclohexyl)carbamate | | | 468 | 7.93ᵉ |
| 203 | 4-amino-N-(trans-4-((2-methylalanyl)amino)-cyclohexyl)-7-(2-ethoxypyridin-4-yl)pyrrolo[2,1-f][1,2,4]triazine-5-carboxamide | | | 481 | 4.32ᶠ |

Example 204

4-Amino-7-(5-hydroxy-1,3,4-oxadiazol-2-yl)-N-(tetrahydro-2H-pyran-4-yl)pyrrolo[2,1-f][1,2,4]triazine-5-carboxamide 204A: Ethyl 4-(bis(4-methoxybenzyl)amino)-7-bromopyrrolo[1,2-f][1,2,4]triazine-5-carboxylate

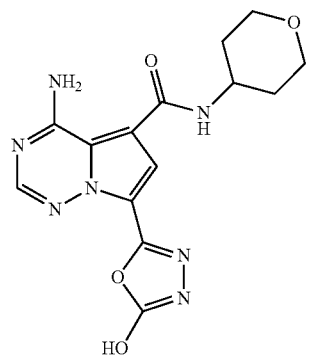 [SMILES: Nc1ncnn2c(-c3nnc(O)o3)cc(C(=O)NC3CCOCC3)c12]

To a mixture of ethyl 7-bromo-4-chloropyrrolo[1,2-f][1,2,4]triazine-5-carboxylate (2A) (2.07 g, 6.80 mmol) and bis(4-methoxybenzyl)amine (1.924 g, 7.48 mmol) in acetonitrile (30 mL) was added triethylamine (1.421 mL, 10.20 mmol). The reaction mixture was stirred at RT for 20 minutes and then concentrated to dryness. The residue was suspended in dichloromethane and the resulting white solid was collected by filtration. The filtrate was concentrated to dryness and purified by ISCO silica gel flash chromatography (EtOAc/DCM=0-50%) to give 204A (3.29 g, 92%). HPLC Rt=4.001 min (Chromolith SpeedROD 4.6×50 mm, 10-90% aqueous methanol containing 0.1% TFA, 4 min gradient, monitored at 220 nm), [M+1]⁺=525.

204B: 4-(Bis(4-methoxybenzyl)amino)-5-(ethoxycarbonyl)pyrrolo[1,2-f][1,2,4]triazine-7-carboxylic acid

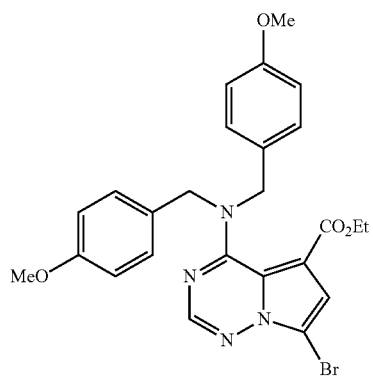 [SMILES: CCOC(=O)c1cc(Br)n2ncnc(N(Cc3ccc(OC)cc3)Cc3ccc(OC)cc3)c12]

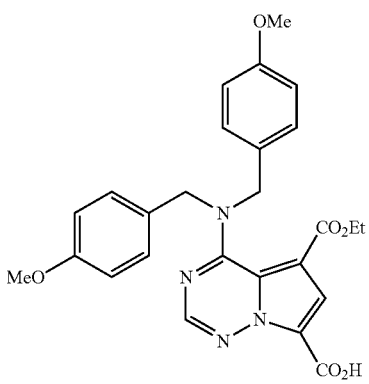 [SMILES: CCOC(=O)c1cc(C(=O)O)n2ncnc(N(Cc3ccc(OC)cc3)Cc3ccc(OC)cc3)c12]

To a solution of 204A (2.3 g, 4.38 mmol) in THF (40 mL) at −78° C. was added 2.5 M butyllithium (1.926 mL, 4.82 mmol) in hexanes dropwise. The resulting mixture was stirred at −78° C. for 10 min and then $CO_2$ was bubbled through the mixture for 40 minutes. The reaction was warmed to room temperature and the quenched with 1N HCl (5.25 mL, 5.25 mmol). The mixture was diluted with EtOAc, washed with water and brine, and then dried over MgSO$_4$. The suspension was filtered, and the filtrate was concentrated to give 204B (2.24 g, 104%). HPLC Rt=3.525 min (Chromolith SpeedROD 4.6×50 mm, 10-90% aqueous methanol containing 0.1% TFA, 4 min gradient, monitored at 220 nm), [M+1]$^+$=491.

204C: Ethyl 4-(bis(4-methoxybenzyl)amino)-7-(2-(tert-butoxycarbonyl)hydrazinecarbonyl)pyrrolo[1,2-f][1,2,4]triazine-5-carboxylate

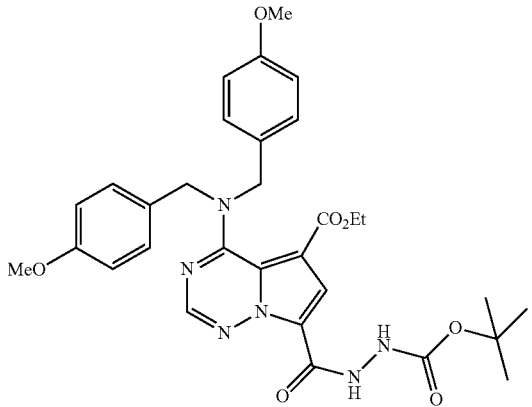 [SMILES: CCOC(=O)c1cc(C(=O)NNC(=O)OC(C)(C)C)n2ncnc(N(Cc3ccc(OC)cc3)Cc3ccc(OC)cc3)c12]

To a solution of 204B (275 mg, 0.561 mmol), tert-butyl hydrazinecarboxylate (74.1 mg, 0.561 mmol) and triethylamine (0.117 mL, 0.841 mmol) in dichloromethane (0.5 mL) was added HATU (256 mg, 0.673 mmol). The resulting mixture was stirred at room temperature for 30 minutes and then diluted with dichloromethane. The solution was washed with water and brine, dried (MgSO$_4$), filtered and concentrated to dryness. The residue was purified by ISCO silica gel chromatography (EtOAc/hexane=0-100%) to give 204C (283 mg, 83%). HPLC Rt=3.683 min (Chromolith SpeedROD 4.6×50 mm, 10-90% aqueous methanol containing 0.1% TFA, 4 min gradient, monitored at 220 nm), [M+1]$^+$=605.

204D: 4-(Bis(4-methoxybenzyl)amino)-7-(2-(tert-butoxycarbonyl)hydrazinecarbonyl)pyrrolo[1,2-f][1,2,4]triazine-5-carboxylic acid

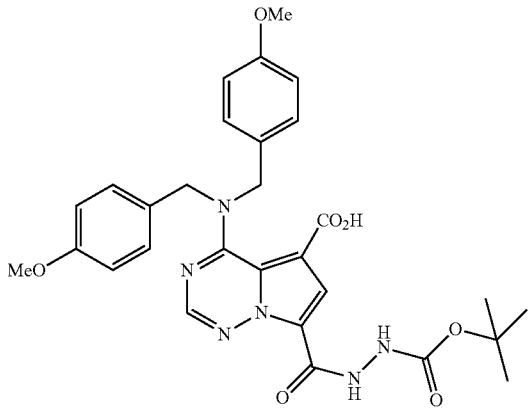 [SMILES: COc1ccc(CN(Cc2ccc(OC)cc2)c2ncnn3c(C(=O)NNC(=O)OC(C)(C)C)cc(C(=O)O)c23)cc1]

To a solution of 204C (283 mg, 0.468 mmol) in THF (2 mL) and MeOH (2 mL) was added a solution of lithium hydroxide monohydrate (79 mg, 1.872 mmol) in water (1 mL). The resulting mixture was stirred at 65° C. overnight. The reaction was cooled to room temperature, acidified with 1N HCl (2 mL), and the resulting mixture was concentrated to remove organic solvents. The aqueous residue was filtered and the solid was washed with water, and dried under vacuum to give 204D (228 mg, 84%). HPLC Rt=3.421 min (Chromolith SpeedROD 4.6×50 mm, 10-90% aqueous methanol containing 0.1% TFA, 4 min gradient, monitored at 220 nm), [M+1]$^+$=577.

204E: tert-Butyl 2-(4-(bis(4-methoxybenzyl)amino)-5-(tetrahydro-2H-pyran-4-ylcarbamoyl)pyrrolo[1,2-f][1,2,4]triazine-7-carbonyl)hydrazinecarboxylate

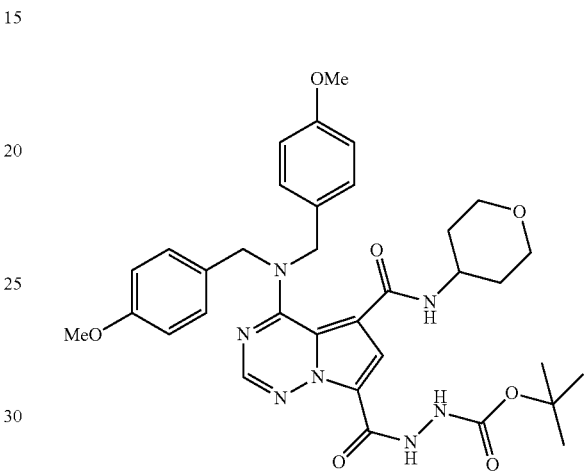

To a mixture of 204D (205 mg, 0.356 mmol) and tetrahydro-2H-pyran-4-amine (43.2 mg, 0.427 mmol) in DMF (0.4 mL) was added HATU (203 mg, 0.533 mmol) and TEA (0.099 mL, 0.711 mmol). The reaction mixture was stirred at room temperature for 30 minutes, and then poured into to water. The resulting white solid was collected by filtration and dried to give 204E (200 mg, 85%). HPLC Rt=3.358 min (Chromolith SpeedROD 4.6×50 mm, 10-90% aqueous methanol containing 0.1% TFA, 4 min gradient, monitored at 220 nm), [M+1]$^+$=660.

204F: 7-(Hydrazinecarbonyl)-4-(4-methoxybenzylamino)-N-(tetrahydro-2H-pyran-4-yl)pyrrolo[1,2-f][1,2,4]triazine-5-carboxamide

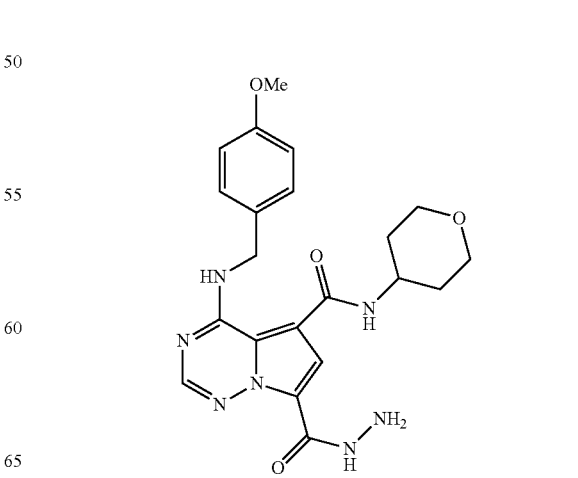

To a solution of 204E (200 mg, 0.303 mmol) in dichloromethane (2 mL) was added triethylsilane (200 μL, 1.252 mmol), followed by TFA (4 mL). The mixture was stirred at 40° C. for 30 minutes and then concentrated to dryness. The crude material was purified by reversed-phase HPLC (YMC ODS C18 5 u 20×100 mm, 10-90% aqueous methanol containing 0.1% TFA, 10 min gradient, monitored at 220 nm) and the desired fractions were combined and concentrated to remove MeOH. The resulting aqueous solution was then made basic with sat.NaHCO$_3$ and the resulting white solid was collected by filtration to afford 204F (70 mg, 53%). HPLC Rt=2.633 min (Chromolith SpeedROD 4.6×50 mm, 10-90% aqueous methanol containing 0.1% TFA, 4 min gradient, monitored at 220 nm), [M+1]$^+$=440.

204G: 4-Amino-7-(hydrazinecarbonyl)-N-(tetrahydro-2H-pyran-4-yl)pyrrolo[1,2-f][1,2,4]triazine-5-carboxamide

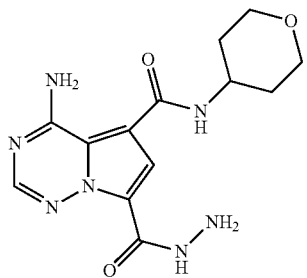 [SMILES: NNC(=O)c1cc(C(=O)NC2CCOCC2)c2c(N)ncnn12]

A mixture of 204F (70 mg, 0.159 mmol) in 98% H$_2$SO$_4$ (1.0 mL) was stirred at room temperature for 7 days. The mixture was pipetted onto a small amount of ice and the resulting mixture was then neutralized with 5N NaOH, and extracted with EtOAc. The combined extracts were concentrated to give 204G (55 mg, 108%) as a white solid. HPLC Rt=1.207 min (Chromolith SpeedROD 4.6×50 mm, 10-90% aqueous methanol containing 0.1% TFA, 4 min gradient, monitored at 220 nm), [M+1]$^+$=320.

204H: 4-Amino-7-(5-oxo-4,5-dihydro-1,3,4-oxadiazol-2-yl)-N-(tetrahydro-2H-pyran-4-yl)pyrrolo[1,2-f][1,2,4]triazine-5-carboxamide, TFA

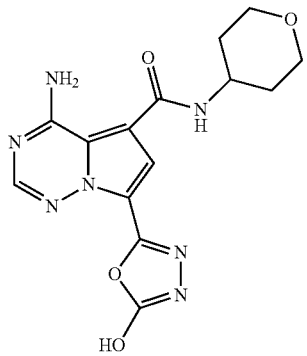 [SMILES: Nc1ncnn2c(-c3nnc(O)o3)cc(C(=O)NC3CCOCC3)c12]

To a solution of 204G (15 mg, 0.047 mmol) in DMF (0.4 mL) was added CDI (7.62 mg, 0.047 mmol). The mixture was stirred at room temperature for 3 days. Additional CDI (7.62 mg, 0.047 mmol) was added and the reaction was stirred until the starting material was consumed. The resulting suspension was dissolved in DMF and purified by reversed-phase HPLC (YMC ODS C18 5 u 20×100 mm, 10-90% aqueous methanol containing 0.1% TFA, 10 min gradient, monitored at 220 nm). The resulting solid was treated with diethyl ether and the resulting solid was collected by filtration to afford 204 as a white solid. (3.0 mg, 12.5%) HPLC Rt=1.733 min (Chromolith SpeedROD 4.6×50 mm, 10-90% aqueous methanol containing 0.1% TFA, 4 min gradient, monitored at 220 nm), [M+1]$^+$=346.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:
1. A compound of formula (I):

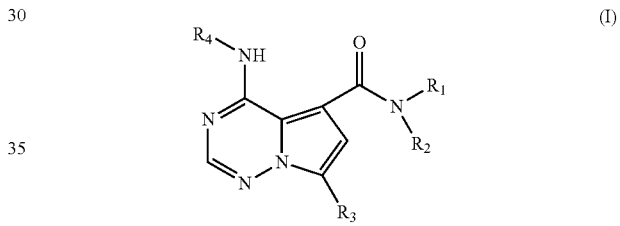

(I)

or a pharmaceutically acceptable salt thereof, wherein
R$_1$ is selected from H, NR$_a$R$_a$, C$_{1-6}$alkyl substituted with 0-5 R$_{1a}$, C$_{2-6}$alkenyl substituted with 0-5 R$_{1a}$, C$_{2-6}$alkynyl substituted with 0-5 R$_{1a}$, —(CHR)$_r$-carbocyclyl substituted with 0-5 R$_{1a}$, —(CHR)$_r$— heterocyclyl substituted with 0-5 R$_{1a}$;
R$_{1a}$, at each occurrence, is independently selected from C$_{1-6}$alkyl substituted with 0-5 R$_e$, C$_{2-6}$alkenyl substituted with 0-5 R$_e$, C$_{2-6}$alkynyl substituted with 0-5 R$_e$, C$_{1-6}$haloalkyl, F, Cl, Br, NO$_2$, CN, =O, —(CHR)$_r$OH, —(CHR)$_r$SH, —(CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$NR$_a$R$_a$, —(CHR)$_r$NR$_a$C(O)R$_d$, —(CHR)$_r$NR$_a$C(O)OR$_b$, —(CHR)$_r$NR$_a$C(O)(CRR)$_r$OC(O)NR$_a$R$_a$, —(CHR)$_r$NR$_a$C(O)(CRR)$_r$NR$_a$R$_a$, —(CHR)$_r$NR$_a$C(O)(CRR)$_r$NR$_a$C(O)OR$_d$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$-carbocyclyl substituted with 0-5 R$_e$ and —(CHR)$_r$-heterocyclyl substituted with 0-5 R$_e$;
R$_2$ is selected from H and C$_{1-6}$alkyl substituted with 0-3 R$_{2a}$;
R$_{2a}$ is selected from F, Cl, and Br;
alternatively, R$_1$ and R$_2$ are taken together with the nitrogen atom to which they are attached to form a heterocyclyl substituted with 0-5 R$_{1a}$;
R$_3$ is selected from aryl substituted with 0-5 R$_{3a}$ and heteroaryl substituted with 0-5 R$_{3a}$;

$R_{3a}$, at each occurrence, is independently selected from $C_{1-6}$alkyl, $C_{2-6}$alkenyl, $C_{2-6}$alkynyl, $C_{1-6}$haloalkyl, F, Cl, Br, NO$_2$, CN, —OH, —SH, —OR$_b$, —S(O)$_p$R$_b$, C(O)R$_d$, —NR$_a$R$_a$, —C(O)NR$_a$R$_a$, —NR$_a$C(O)R$_d$, —NR$_a$C(O)OR$_b$, —OC(O)NR$_a$R$_a$, —C(O)OR$_d$, —S(O)$_p$NR$_a$R$_a$, —NR$_a$S(O)$_p$R$_b$;

$R_4$ is selected from H, $C_{1-6}$alkyl, and $C_{3-6}$cycloalkyl;

$R_a$, at each occurrence, is independently selected from H, NH$_2$, $C_{1-6}$alkyl substituted with 0-3 R$_e$, $C_{2-6}$alkenyl substituted with 0-3 R$_e$, $C_{2-6}$alkynyl substituted with 0-3 R$_e$, $C_{1-6}$haloalkyl, —(CH$_2$)$_r$OH, (CH$_2$)$_r$carbocyclyl substituted with 0-3 R$_e$, and (CH$_2$)$_r$-heterocyclyl substituted with 0-3 R$_e$, or R$_a$ and R$_a$ together with the nitrogen atom to which they are attached form a heterocyclyl substituted with 0-3 R$_e$;

$R_b$, at each occurrence, is independently selected from $C_{1-6}$alkyl substituted with 0-3 R$_e$, $C_{1-6}$haloalkyl, $C_{2-6}$alkenyl substituted with 0-3 R$_e$, $C_{2-6}$alkynyl substituted with 0-3 R$_e$, —(CH$_2$)$_r$carbocyclyl substituted with 0-3 R$_e$, and —(CH$_2$)$_r$heterocyclyl substituted with 0-3 R$_e$;

$R_d$, at each occurrence, is independently selected from H, $C_{1-6}$alkyl substituted with 0-3 R$_e$, $C_{1-6}$haloalkyl, $C_{2-6}$alkenyl substituted with 0-3 R$_e$, $C_{2-6}$alkynyl substituted with 0-3 R$_e$, —(CH$_2$)$_r$— carbocyclyl substituted with 0-3 R$_e$, and —(CH$_2$)$_r$-heterocyclyl substituted with 0-3 R$_e$;

$R_e$, at each occurrence, is independently selected from $C_{1-6}$alkyl, $C_{2-6}$alkenyl, $C_{2-6}$alkynyl, (CH$_2$)$_r$C$_{3-6}$cycloalkyl, F, Cl, Br, CN, NO$_2$, CO$_2$H, =O, —C(O)NR$_f$R$_f$, (CF$_2$)$_r$CF$_3$, —(CH$_2$)$_r$OC$_{1-5}$alkyl, —(CH$_2$)$_r$OH, SH, —(CH$_2$)$_r$SC$_{1-5}$alkyl, —(CH$_2$)$_r$NR$_f$R$_f$, —(CH$_2$)$_r$phenyl, and (CH$_2$)$_r$heterocyclyl;

$R_f$, at each occurrence, is independently selected from H, $C_{1-5}$alkyl, $C_{3-6}$cycloalkyl, and phenyl;

R, at each occurrence, is independently selected from H, —(CH$_2$)$_r$OH, $C_{1-6}$alkyl, $C_{1-6}$haloalkyl, and —(CH$_2$)$_r$-aryl;

p, at each occurrence, is independently selected from 0, 1, and 2; and r, at each occurrence, is independently selected from 0, 1, 2, 3, and 4.

2. The compound according to claim 1, wherein $R_3$ is selected from aryl substituted with 0-4 R$_{3a}$ and heteroaryl substituted with 0-4 R$_{3a}$, wherein said heteroaryl comprises carbon atoms and 1-4 heteroatoms selected from N, 0, and S(O)$_p$; and $R_{3a}$, at each occurrence, is independently selected from $C_{1-6}$alkyl, $C_{2-6}$alkenyl, $C_{2-6}$alkynyl, $C_{1-6}$haloalkyl, F, Cl, Br, NO$_2$, CN, —OH, —SH, —OR$_b$, —C(O)R$_d$, —NR$_a$R$_a$, —C(O)NR$_a$R$_a$, and —C(O)OR$_d$.

3. The compound according to claim 2, wherein $R_3$ is heteroaryl selected from pyridyl, pyrimidinyl, pyrazinyl, pyridazinyl, triazinyl, furyl, quinolyl, isoquinolyl, thienyl, imidazolyl, thiazolyl, indolyl, pyrrolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane, each of which is substituted with 0-3 R$_{3a}$.

4. The compound according to claim 2, wherein $R_1$ is selected from —(CHR)$_r$-carbocyclyl substituted with 0-4 R$_{1a}$, —(CHR)$_r$-heterocyclyl substituted with 0-4 R$_{1a}$;

$R_{1a}$, at each occurrence, is independently selected from $C_{1-4}$alkyl substituted with 0-4 R$_e$, $C_{2-6}$alkenyl substituted with 0-4 R$_e$, $C_{2-4}$alkynyl substituted with 0-4 R$_e$, $C_{1-4}$haloalkyl, F, Cl, Br, NO$_2$, CN, =O, —(CHR)$_r$OH, —(CHR)$_r$SH, (CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$NR$_a$R$_a$, —(CHR)$_r$NR$_a$C(O)R$_d$, —(CHR)$_r$NR$_a$C(O)OR$_b$, —(CHR)$_r$NR$_a$C(O)(CRR)$_r$OC(O)NR$_a$R$_a$, —(CHR)$_r$NR$_a$C(O)(CRR)$_r$NR$_a$R$_a$, —(CHR)$_r$NR$_a$C(O)(CRR)$_r$NC(O)OR$_d$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$-carbocyclyl substituted with 0-4 R$_e$ and —(CHR)$_r$-heterocyclyl substituted with 0-4 R$_e$;

$R_a$, at each occurrence, is independently selected from H, NH$_2$, $C_{1-6}$alkyl substituted with 0-3 R$_e$, $C_{2-6}$alkenyl substituted with 0-3 R$_e$, $C_{2-6}$alkynyl substituted with 0-3 R$_e$, —(CH$_2$)$_r$OH, (CH$_2$)$_r$carbocyclyl substituted with 0-3 R$_e$, and (CH$_2$)$_r$-heterocyclyl substituted with 0-3 R$_e$, or R$_a$ and R$_a$ together with the nitrogen atom to which they are attached form a heterocyclyl substituted with 0-3 R$_e$;

$R_b$, at each occurrence, is independently selected from $C_{1-6}$alkyl substituted with 0-3 R$_e$, $C_{2-6}$alkenyl substituted with 0-3 R$_e$, $C_{2-6}$alkynyl substituted with 0-3 R$_e$, —(CH$_2$)$_r$carbocyclyl substituted with 0-3 R$_e$, and —(CH$_2$)$_r$heterocyclyl substituted with 0-3 R$_e$;

$R_d$, at each occurrence, is independently selected from H, $C_{1-6}$alkyl substituted with 0-3 R$_e$, $C_{2-6}$alkenyl substituted with 0-3 R$_e$, $C_{2-6}$alkynyl substituted with 0-3 R$_e$, —(CH$_2$)$_r$-carbocyclyl substituted with 0-3 R$_e$, and —(CH$_2$)$_r$-heterocyclyl substituted with 0-3 R$_e$;

$R_e$, at each occurrence, is independently selected from $C_{1-6}$alkyl, $C_{2-6}$alkenyl, $C_{2-6}$alkynyl, (CH$_2$)$_r$C$_{3-6}$cycloalkyl, F, Cl, Br, CN, NO$_2$, CO$_2$H, =O, —C(O)NR$_f$R$_f$, —(CH$_2$)$_r$OC$_{1-5}$alkyl, —(CH$_2$)$_r$OH, SH, —(CH$_2$)$_r$SC$_{1-5}$alkyl, —(CH$_2$)$_r$NR$_f$R$_f$, —(CH$_2$)$_r$phenyl, and (CH$_2$)$_r$heterocyclyl;

$R_f$, at each occurrence, is independently selected from H, $C_{1-4}$alkyl, and phenyl;

R, at each occurrence, is independently selected from H, —(CH$_2$)$_r$OH, $C_{1-6}$alkyl, $C_{1-6}$haloalkyl, and —(CH$_2$)$_r$-aryl;

p, at each occurrence, is independently selected from 0, 1, and 2; and r, at each occurrence, is independently selected from 0, 1, 2, 3, and 4.

5. The compound according to claim 4, wherein $R_1$ is selected from —(CHR)$_r$-aryl substituted with 0-3 R$_{1a}$ and —(CHR)$_r$—C$_{3-7}$cycloalkyl substituted with 0-3 R$_{1a}$.

6. The compound according to claim 5, wherein $R_1$ is —(CH$_2$)$_r$—C$_{3-7}$cycloalkyl substituted with 0-3 R$_{1a}$;

$R_{1a}$, at each occurrence, is independently selected from $C_{1-4}$alkyl substituted with 0-3 R$_e$, =O, —(CHR)$_r$OH, —OR$_b$, —C(O)R$_d$, —NR$_a$R$_a$, —C(O)NR$_a$R$_a$, —NHC(O)R$_d$, —NHC(O)OR$_b$, —NHC(O)(CRR)$_r$OC(O)NR$_a$R$_a$, —NHC(O)(CRR)$_r$NR$_a$R$_a$, —NHC(O)(CRR)$_r$NHC(O)OR$_d$, —C(O)OR$_d$, —S(O)$_2$NR$_a$R$_a$, —NHS(O)$_2$R$_b$, aryl substituted with 0-3 R$_e$ and heterocyclyl substituted with 0-3 R$_e$;

$R_a$, at each occurrence, is independently selected from H, $C_{1-6}$alkyl substituted with 0-3 R$_e$, —(CH$_2$)$_r$-aryl substituted with 0-3 R$_e$, —(CH$_2$)$_r$—C$_{3-6}$cycloalkyl substituted with 0-3 R$_e$, and —(CH$_2$)$_r$-heterocyclyl substituted with 0-3 R$_e$, or R$_a$ and R$_a$ together with the nitrogen atom to which they are attached form a heterocyclyl substituted with 0-3 R$_e$;

$R_b$, at each occurrence, is independently selected from $C_{1-6}$alkyl substituted with 0-3 R$_e$, —(CH$_2$)$_r$-aryl substituted with 0-3 $R_e$, —$(CH_2)_r$—$C_{3-6}$cycloalkyl substituted with 0-3 $R_e$, and —$(CH_2)_r$heterocyclyl substituted with 0-3 $R_e$;

$R_d$, at each occurrence, is independently selected from H, $C_{1-6}$alkyl substituted with 0-3 $R_e$, —$(CH_2)_r$-aryl substituted with 0-3 $R_e$, —$(CH_2)_r$—$C_{3-6}$cycloalkyl substituted with 0-3 $R_e$, and —$(CH_2)_r$-heterocyclyl substituted with 0-3 $R_e$;

$R_e$, at each occurrence, is independently selected from $C_{1-6}$alkyl, $(CH_2)_rC_{3-6}$cycloalkyl, F, Cl, Br, CN, $CO_2H$, =O, —C(O)$NR_fR_f$, —$(CH_2)_rOC_{1-5}$alkyl, —$(CH_2)_r$OH, —$(CH_2)_rNR_fR_f$, —$(CH_2)_r$phenyl, and $(CH_2)_r$heterocyclyl;

$R_f$, at each occurrence, is independently selected from H and $C_{1-4}$alkyl;

R, at each occurrence, is independently selected from H and $C_{1-4}$alkyl; and r, at each occurrence, is independently selected from 0, 1, 2, and 3.

7. The compound according to claim 5, wherein $R_1$ is —(CHR)$_r$-aryl substituted with 0-3 $R_{1a}$;

$R_{1a}$, at each occurrence, is independently selected from $C_{1-4}$alkyl substituted with 0-3 $R_e$, CN, —(CHR)$_r$OH, (CHR)$_rOR_b$, —(CHR)$_rS(O)_2R_b$—(CHR)$_rS(O)_2NR_aR_a$, —(CHR)$_rNR_aS(O)_2R_b$, aryl substituted with 0-3 $R_e$ and —$(CH_2)_r$-heterocyclyl substituted with 0-3 $R_e$;

$R_a$, at each occurrence, is independently selected from H and $C_{1-6}$alkyl substituted with 0-3 $R_e$;

$R_b$, at each occurrence, is independently selected from $C_{1-6}$alkyl substituted with 0-3 $R_e$, —$(CH_2)_r$-aryl substituted with 0-3 $R_e$, —$(CH_2)_r$—$C_{3-6}$cycloalkyl substituted with 0-3 $R_e$, and —$(CH_2)_r$heterocyclyl substituted with 0-3 $R_e$;

$R_e$, at each occurrence, is independently selected from $C_{1-6}$alkyl, $(CH_2)_rC_{3-6}$cycloalkyl, F, Cl, Br, CN, $CO_2H$, =O, —$(CH_2)_rOC_{1-5}$alkyl, —$(CH_2)_r$OH, —$(CH_2)_r$phenyl, and $(CH_2)_r$heterocyclyl;

R, at each occurrence, is independently selected from H, OH, and $C_{1-4}$alkyl; and r, at each occurrence, is independently selected from 0, 1, 2, and 3.

8. The compound according to claim 2, wherein $R_1$ is selected from —(CHR)$_r$-heterocyclyl substituted with 0-3 $R_{1a}$;

$R_{1a}$, at each occurrence, is independently selected from $C_{1-4}$alkyl substituted with 0-3 $R_e$, CN, =O, —$(CH_2)_r$OH, $(CH_2)_rOR_b$, —$(CH_2)_rS(O)_pR_b$, —$(CH_2)_rC(O)R_d$, —$(CH_2)_rNR_aR_a$, —$(CH_2)_rC(O)NR_aR_a$, —$(CH_2)_rC(O)OR_d$, —$(CH_2)_rS(O)_pNR_aR_a$, —(CHR)$_rNR_aS(O)_pR_b$, —(CHR)$_r$-aryl substituted with 0-3 $R_e$ and —(CHR)$_r$-heterocyclyl substituted with 0-3 $R_e$;

$R_a$, at each occurrence, is independently selected from H, $NH_2$, $C_{1-6}$alkyl substituted with 0-3 $R_e$, or $R_a$ and $R_a$ together with the nitrogen atom to which they are attached form a heterocyclyl substituted with 0-3 $R_e$;

$R_b$, at each occurrence, is independently selected from $C_{1-6}$alkyl substituted with 0-3 $R_e$, —$(CH_2)_r$carbocyclyl substituted with 0-3 $R_e$, and —$(CH_2)_r$heterocyclyl substituted with 0-3 $R_e$;

$R_d$, at each occurrence, is independently selected from H, $C_{1-6}$alkyl substituted with 0-3 $R_e$, —$(CH_2)_r$—$C_{3-6}$cycloalkyl substituted with 0-3 $R_e$, and —$(CH_2)_r$heterocyclyl substituted with 0-3 $R_e$;

$R_e$, at each occurrence, is independently selected from $C_{1-6}$alkyl, CN, $NO_2$, $CO_2H$, =O, —C(O)$NH_2$, —$(CH_2)_rOC_{1-5}$ alkyl, —$(CH_2)_r$OH, SH, —$(CH_2)_rSC_{1-5}$alkyl, —$(CH_2)_rNH_2$, —$(CH_2)_r$phenyl, and $(CH_2)_r$heterocyclyl;

R, at each occurrence, is independently selected from H, —$(CH_2)_r$OH, $C_{1-4}$alkyl, and —$(CH_2)_r$-aryl;

p, at each occurrence, is independently selected from 0, 1, and 2; and r, at each occurrence, is independently selected from 0, 1, 2, 3, and 4.

9. The compound according to claim 2, wherein $R_1$ and $R_2$ are taken together with the nitrogen atom to which they are attached to form a heterocyclyl substituted with 0-3 $R_{1a}$;

$R_{1a}$, at each occurrence, is independently selected from $C_{1-4}$alkyl substituted with 0-3 $R_e$, —$(CH_2)_r$OH, —$(CH_2)_rS(O)_pR_b$, —$(CH_2)_rC(O)R_d$, —$(CH_2)_rNR_aR_a$, —$(CH_2)_rC(O)NR_aR_a$, —$(CH_2)_rNHC(O)R_d$, —$(CH_2)_rNHC(O)OR_b$;

$R_a$, at each occurrence, is independently selected from H and $C_{1-6}$alkyl substituted with 0-3 $R_e$;

$R_b$, at each occurrence, is independently selected from $C_{1-6}$alkyl substituted with 0-3 $R_e$, —$(CH_2)_r$-aryl substituted with 0-3 $R_e$, —$(CH_2)_r$—$C_{3-6}$cycloalkyl substituted with 0-3 $R_e$, and —$(CH_2)_r$heterocyclyl substituted with 0-3 $R_e$;

$R_d$, at each occurrence, is independently selected from H, $C_{1-6}$alkyl substituted with 0-3 $R_e$, —$(CH_2)_r$-aryl substituted with 0-3 $R_e$, —$(CH_2)_r$—$C_{3-6}$cycloalkyl substituted with 0-3 $R_e$, and —$(CH_2)_r$heterocyclyl substituted with 0-3 $R_e$;

$R_e$, at each occurrence, is independently selected from $C_{1-6}$alkyl, $(CH_2)_rC_{3-6}$cycloalkyl, F, Cl, Br, CN, $CO_2H$, =O, —$(CH_2)_rOC_{1-5}$alkyl, —$(CH_2)_r$OH, —$(CH_2)_r$phenyl, and $(CH_2)_r$heterocyclyl; and r, at each occurrence, is independently selected from 0, 1, 2, and 3.

10. The compound according to claim 2, wherein $R_1$ is $C_{1-5}$alkyl substituted with 0-3 $R_{1a}$;

$R_{1a}$, at each occurrence, is independently selected from $C_{1-4}$alkyl substituted with 0-3 $R_e$, —$(CH_2)_r$OH, —$(CH_2)_rC(O)OR_d$, —$(CH_2)_rNR_aR_a$, —$(CH_2)_rC(O)NR_aR_a$, —$(CH_2)_rNHC(O)R_d$, —$(CH_2)_rNHC(O)OR_b$, and —$(CH_2)_rNHS(O)_2R_b$;

$R_a$, at each occurrence, is independently selected from H and $C_{1-6}$alkyl substituted with 0-3 $R_e$;

$R_b$, at each occurrence, is independently selected from $C_{1-6}$alkyl substituted with 0-3 $R_e$, —$(CH_2)_r$-aryl substituted with 0-3 $R_e$, —$(CH_2)_r$—$C_{3-6}$cycloalkyl substituted with 0-3 $R_e$, and —$(CH_2)_r$heterocyclyl substituted with 0-3 $R_e$;

$R_d$, at each occurrence, is independently selected from H, $C_{1-6}$alkyl substituted with 0-3 $R_e$, —$(CH_2)_r$-aryl substituted with 0-3 $R_e$, —$(CH_2)_r$—$C_{3-6}$cycloalkyl substituted with 0-3 $R_e$, and —$(CH_2)_r$heterocyclyl substituted with 0-3 $R_e$;

$R_e$, at each occurrence, is independently selected from $C_{1-6}$alkyl, $(CH_2)_rC_{3-6}$cycloalkyl, F, Cl, Br, CN, $CO_2H$, =O, —$(CH_2)_rOC_{1-5}$alkyl, —$(CH_2)_r$OH, —$(CH_2)_r$phenyl, and $(CH_2)_r$heterocyclyl; and r, at each occurrence, is independently selected from 0, 1, 2, and 3.

11. A pharmaceutical composition comprising one or more compounds according to claim 1 and a pharmaceutically acceptable carrier.

12. A pharmaceutical composition comprising one or more compounds according to claim 1 in combination with a pharmaceutically acceptable carrier and one or more other anti-cancer or cytotoxic agents.

13. A method for treating rheumatoid arthritis and breast cancer comprising administering to a patient in need thereof, a therapeutically effective amount of one or more compounds according to claim 1.

* * * * *